US005866601A

United States Patent [19]
Lew et al.

[11] Patent Number: 5,866,601
[45] Date of Patent: Feb. 2, 1999

[54] CARBOCYCLIC COMPOUNDS

[75] Inventors: Willard Lew, San Mateo; Choung U. Kim, San Carlos; Hongtao Liu; Matthew A. Williams, both of Foster City, all of Calif.

[73] Assignee: Gilead Sciences, Inc., Foster City, Calif.

[21] Appl. No.: 476,946

[22] Filed: Jun. 6, 1995

Related U.S. Application Data

[63] Continuation-in-part of Ser. No. 395,245, Feb. 27, 1995, abandoned.

[51] Int. Cl.⁶ .......................... A61K 31/35; A61K 31/66; A61K 31/445
[52] U.S. Cl. .......................... 514/459; 514/102; 514/315; 514/365; 514/381; 514/396; 514/401
[58] Field of Search ................................ 514/459, 102, 514/316, 365, 381, 396, 401

[56] References Cited

U.S. PATENT DOCUMENTS

| | | | |
|---|---|---|---|
| 4,968,788 | 11/1990 | Farquhar | 536/27 |
| 5,175,273 | 12/1992 | Bischofberger et al. | 536/26.13 |
| 5,206,400 | 4/1993 | Witiak et al. | 556/137 |
| 5,292,938 | 3/1994 | Mease et al. | 562/507 |
| 5,360,817 | 11/1994 | von Izstein et al. | 514/459 |
| 5,428,073 | 6/1995 | Kunisch et al. | 514/561 |
| 5,512,596 | 4/1996 | Kim et al. | 514/568 |
| 5,514,798 | 5/1996 | Bischofberger et al. | 544/243 |
| 5,536,734 | 7/1996 | Mueller et al. | 514/336 |
| 5,556,963 | 9/1996 | Liav et al. | 536/55.3 |
| 5,597,933 | 1/1997 | Searle et al. | 549/424 |
| 5,622,916 | 4/1997 | Kunisch et al. | 504/269 |
| 5,714,509 | 2/1998 | Luo et al. | 514/445 |

FOREIGN PATENT DOCUMENTS

| | | |
|---|---|---|
| PJ 9800 | 11/1991 | Australia . |
| PK 2896 | 11/1991 | Australia . |
| PK 4537 | 11/1991 | Australia . |
| 654815 | 11/1994 | Australia . |
| 0 534 216 A1 | 9/1992 | European Pat. Off. . |
| 0 539 204 A1 | 10/1992 | European Pat. Off. . |
| 9510141 | 5/1995 | United Kingdom . |
| 9516276 | 8/1995 | United Kingdom . |
| 9525389 | 12/1995 | United Kingdom . |
| WO 91/16320 | 10/1991 | WIPO . |
| WO 92/06691 | 4/1992 | WIPO . |
| WO 93/12105 | 6/1993 | WIPO . |
| WO 93/16049 | 8/1993 | WIPO . |
| WO 96/30329 | 10/1993 | WIPO . |
| WO 94/07885 | 4/1994 | WIPO . |
| WO 94/07886 | 4/1994 | WIPO . |
| WO 94/28956 | 12/1994 | WIPO . |
| WO 94/29476 | 12/1994 | WIPO . |
| WO 95/00503 | 1/1995 | WIPO . |
| WO 95/16680 | 6/1995 | WIPO . |
| WO 95/18800 | 7/1995 | WIPO . |
| WO 95/20583 | 8/1995 | WIPO . |
| WO 95/32712 | 12/1995 | WIPO . |
| WO 96/04265 | 2/1996 | WIPO . |
| WO 96/36628 | 11/1996 | WIPO . |
| WO 96/39838 | 12/1996 | WIPO . |

OTHER PUBLICATIONS

Chahoua et al., "Synthesis of (–)–Shikimate and (–)–Quinate 3–Phosphates by Differentiation of the Hydroxyl Functions of (–)–Shikimic and (–)–Quinic Acids", 57:5798–5801, J Org Chem, 1992.

Fernandez et al., "New and Efficient Enantiospecific Synthesis of (–)–Methyl 5–epi–Shikimate and Methyl 5–epi–Quinate from (–)–Quinic Acid", 38(29):5225–5228, Tet Lett, 1997.

Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti–Influenza Activity", 119:681–690, J. Am. Chem Soc, 1997.

Ulibarri et al., "Construction of the Bicyclic Core Structure of the Enediyne Antibiotic Esperamicin–A1 in Either Anantimeric Form from (–)–Quinic Acid", 60:2753–2761, J Org Chem, 1995.

Berger, Alfred, "Relation of Chemical Structure and Biological Activity", Medicinal Chemistry Third edition, part 1, pp. 73–75 (1979).

Luo et al., "Abstract of Presentation C52: Designed Non–Carbohydrate Inhibitors or Influenza Virus Neuraminidase and Accompanying Notes," International Antiviral Conference, Nice, France, Jun. 10, (1994).

Raner et al., Aust J Chem, 43:609–616 (1990).

Smith et al., "Novel Inhibitors of Influenza Sialidases Related to GG167," Bioorg Med Chem Lett 6(4):2931–2936 (1996).

Meindl et al., "2–Deoxy–2,3–dehydrosialic acids. 3. Inhibition of Vibrio cholerae[comma]neuraminidase by oxidation products of 2–deoxy–2,3–dehydro–N–acetylneuraminic acid", 73:42027b, Chem Ab, 1970.

Bamford et al., "Synthesis of 6–,7–and 8–carbon sugar analogues of potent anti–influenza 2,3–didehydro–2, 3–dideoxy–N–actylneuramine acid derivatives," J Chem Soc Perkin Trans I pp. 1181–1187 (1995).

Bamford, Mark J., "Neuraminidase inhibitors as Potential Anti–Infleunza Drugs," J Enzyme Inhibition 10:1–16 (1995).

(List continued on next page.)

Primary Examiner—Kevin Weddington
Attorney, Agent, or Firm—Mark L. Bosse

[57] ABSTRACT

Novel carbocyclic compounds are described. The compounds generally comprise an acidic group, a basic group, a substituted amino or N-acyl and a group having an optionally hydroxylated alkane moiety. Pharmaceutical compositions comprising the inhibitors of the invention are also described. Methods of inhibiting neuraminidase in samples suspected of containing neuraminidase are also described. Antigenic materials, polymers, antibodies, conjugates of the compounds of the invention with labels, and assay methods for detecting neuraminidase activity are also described.

31 Claims, No Drawings

OTHER PUBLICATIONS

Carless et al., "Synthesis of Pseudo–alpha–L–fucopyranose from Toluene," J Chem Soc (C) pp. 2447–2448 (1995).

Chandler et al., "Approaches to carbocyclic analogues of the potent neuraminidase inhibitor 4–quanidino–Neu5Ac2en. X–Ray molecular structure of N–[(1S,2S, 6R)–2–azido–6–benzyloxymethyl–4–formycyclohex–3–enyl]acteamide," J Chem Soc Perkin Trans I pp. 1189–1197 (1995).

Chandler et al., "Synthesis of the potent influenza neuraminidase inhibitor 4–guanidino Neu5Ac2en. X–Ray molecular structure of 5–acetamido–4–amino–2,6–anhydro–3,4,5–trideoxy–D–erthro–L–gluco–noninic acid," J Chem Soc Perkin Trans I pp. 1173–1180 (1995).

Ciccotosto et al., "Synthesis of Methyl 5–Actamido–3,4, 5–trideoxy–4–Gluanidinyl–D–glycero–D–galacto–2–nonulopyranosidonic acid (4–deoxy–4–guanidino–Neu5Acalpha2Me)," Tet Lett 36(30):5405–5408 (1995).

Colman, P.M., "Infleunza virus neuraminidase: Structure, antibodies, and inhibitors," Protein Science 3:1687–1696(1994).

Dernick, Rudolf, "Sterical Requirements for Inhibitors of Viral Neuraminidases," Chem Ab 96:256 (1982).

Douglas, R. Gordon, Jr., "Prophylaxis and Treatment of Infleunza," N Engl J Med 322(7):443–450 (Feb. 15, 1990).

Ganem, Bruce, "Tetrahedron Report No. 59. From Glucose to Aromatics: Recent Developments in Natural Products of the Shikimic Acid Pathway," Tetrahedron 34:3353–3383 (1978).

Grewe et al, "Abbau der Chinasaure nach Hunsdiecker," Chem Ber 98:104–110 (1965).

Grewe et al, "Darstellung und Eigenschaften des Chinaaldehyds," Liebigs Ann Chem 658:113–119 (1962).

Grewe et al, "Die Totalsythesis der Chinasaure," Chem Ber 87:793–802 (1954).

Grewe et al, "Die Uberfuhrung der Shikimisaure in Chinasaure," Chem Ber 86:928–938 (1953).

Grewe et al, "Eine einfache Synthese der Shikimisaure," Chem Ber 100:2546–2553 (1967).

Grewe et al, "Eine neue Synthese der Shikimisaure," Chem Ber 97:443–448 (1964).

Grewe et al, "Synthese der Homochinasaure und des beta–Chino–athylamins," Liebigs Ann Chem 575:1–17 (1952).

Grewe et al, "Uberfuhrung der chinasaure in ungesattigte Verbindungen vom Typ der Shikimisaure," Angew Chem Int Ed 69:61 (1957).

Hanessian et al., "Anomeric Deoxygenation of 2–Ulosonic Acids Using SmI2: Rapid Access to 2–Deoxy–KDO and 2–Deoxy–NANA," Synlett pp. 863–864 (Oct. 1994).

Hayden et al., "Safety and Efficacy of the Neuraminidase Inhibitor GG167 in Experimental Human Infleunza," JAMA 275(4):295–299 (Jan. 1996).

Janakiraman et al., "Structure of Influenza Virus Neuraminidase B/Lee/40 Complexed with Sialic Acid and a Dehydro Analog at 1.8–Angstrom Resolution: Implications for the Catalytic Mechanism," Biochem 33:8172–8179 (1994).

Kiefel et al., "Synthesis and Biological Evaluation ofN–Acetylneuraminic Acid–Based Rotavirus Inhibitors," J Med Chem 39:1314–1320 (1996).

Kong et al., "The First Synthesis of a C–7 Nitrogen–containing Sialic Acid Analogue, 5–Acetamido–7–azido–3,5, 7–trideoxy–D–glycero–D–galacto–2–nonulopyranosonic acid (7–azido–deoxy–Neu5Ac)," Tet Lett 36(6):957–960 (1995).

Kudo et al., "Synthesis of the Potent Inhibitors of Neuraminidase, N–(1,2–Dihydroxypropyl) Derivatives of Siastain B and its 4–Deoxy Analogs," J Antibiot 46(2):300–309 (Feb. 1993).

McCauley et al., "4–Guanidino–Neu5Ac2en fails to protect chickens from infection with highly pathogenic avian influenza virus," Antiviral Res 27:179–186 (1995).

McKimm–Breschkin et al., "Generation and Characterization of Variants of NWS/G70C Infleunza Virus after In Vitro Passage in 4–Amino–Neu5Ac2en and 4–Guanidino–Neu4Ac2en," Antimicro Ag & Chemo 40(1):40–46 (Jan. 1996).

Nishimura et al., "Design of Potential Neuraminidase Inhibitors By Dehydration, Deoxygenation and Epimerization of Siastatin B," Natural Product Letters 1(1):39–44 (1992).

Nishimura et al., "Synthesis of 3–Episiastatin B Analogues Having Anti–Infleunza Virus Activity," J Antibiot 46(12):1883–1889 (Dec. 1993).

Ogawa et al., "Synthesis of a Carbocyclic Analogue of N–Acetylneuraminic Acid (Pseudo–N–acteylneuraminic Acid)," J Chem Soc (C) pp. 406–408 (1992).

Ogawa et al., "Synthesis of carbocyclic analogues of 3–deoxy–D–manno–2–octulosonic acid and N–acetylneuraminic acid," Caeb Res 269:53–78 (1995).

Ryan et al., "Inhibition of Infleunza Virus in Mice by GG167 (4–Guanidino–2,4–Dideoxy–2,3–Dehydro–N–Acetylneuraminic Acid) Is Consistent with Extracellular Activity of Viral Neuraminidase (Sialidase)," Antimicro Ag & Chemo 38(10):2270–2275 (Oct. 1994).

Saito et al., "Steps in Maturation of Infleunza A Virus Neuraminidase," J Virol 69(8):5011–5017 (Aug. 1995).

Singh et al., "Structure–Based Inhibitors of Infleunza Virus Sialidase. A Benzoic Acid Lead with Novel Interaction," J Med Chem 38:3217–3225 (1995).

Smith et al., "Synthesis and infleunza virus sialidase inhibitory activity of analogues of 4–guanidino–Neu5Ac2en (GG167) with modified 5–substituents," Eur J Med Chem 31:143–150 (Jun. 22, 1995).

Sollis et al, "Novel Inhibitors of Influenza Sialidase Related to GG167," Bioorg Med Chem Lett 6(15):1805–1808, Abstract, Table of Contents (1996).

Starkey et al., "Synthesis and influenza Virus Sialidase Inhibitory of the 5–Desacetamido Analogue of 2,3–Didehydro–2,4–dideoxy–4–guanidinyl–N–acetylneutaminic acid," Tet Lett 36(2):299–302 (1995).

Staschke et al., "Molecular Basis for the Resistance of Influenza Viruses to 4–Guanidino–Neu5Ac2en," Virology 214:642–646 (1995).

Ulmer et al., "Heterologous Protection Against Influenza by Injection of DNA Encoding a Viral Protein," Science 259:1745–1749 (Mar. 19, 1993).

Wu et al., "Non–Sialate Inhibitor or Influenza A/WSN/33 Neuraminidase," Biochem 34:7154–7160 (1995).

von Itzstein et al, "Rational design of potent sialidase–based inhibitors of Influenza virus replication," Nature 363:418–423 (1993).

von Itzstein et al., "A Study of the Active Site Influenza Virus Sialidase: An approach to the Rational Design of Novel Anti–influenza Drugs," J Med Chem 39:388–391 (1996).

CARBOCYCLIC COMPOUNDS

CROSS-REFERENCE TO RELATED APPLICATIONS

This application is a continuation-in-part of U.S. patent application Ser. No. 08/395,245, filed Feb. 27, 1995, now abandoned which is incorporated by reference.

BACKGROUND OF THE INVENTION

FIELD OF THE INVENTION

Neuraminidase (also known as sialidase, acylneuraminyl hydrolase, and EC 3.2.1.18) is an enzyme common among animals and a number of microorganisms. It is a glycohydrolase that cleaves terminal alpha-ketosidically linked sialic acids from glycoproteins, glycolipids and oligiosaccharides. Many of the microorganisms containing neuraminidase are pathogenic to man and other animals including fowl, horses, swine and seals. These pathogenic organisms include influenza virus.

Neuraminidase has been implicated in the pathogenicity of influenza virus. It is thought to help the elution of newly synthesized virons from infected cells and assist in the movement of the virus (through its hydrolase activity) through the mucus of the respiratory tract.

Inhibition of glycolytic enzymes such as neuraminidase is an object of the invention.

An additional object of the invention is to provide neuraminidase inhibitors that exhibit lengthy biological half-lives compared to known compounds.

Another object is to provide improved and less costly methods for synthesis of neuraminidase inhibitors.

A further object is to provide such inhibitors having elevated potency, substantial oral bioavailability (>15%) and pharmaceutically acceptable or absent toxicity.

An additional object is to provide compositions useful in preparing polymers, surfactants, immunogens and for use in other industrial processes and articles as will be readily apparent to the ordinary artisan or as is further described herein.

BRIEF DESCRIPTION OF RELATED ART

Itzstein, M. von; et al.; *Nature* 1993, 363(6428), 418–423, discloses the rational design of sialidase-based inhibitors of influenza virus replication.

Colman, P. M.; et al.; International Patent Publication No. WO 92/06691 (Int. App. No. PCT/AU90/00501, publication date Apr. 30, 1992), Itzstein, L. M. von; et al.; European Patent Publication No. 0 539 204 A1 (EP App. No. 92309684.6, publication date Apr. 28, 1993), and Itzstein, L. M. von; et al.; International Publication No. WO 91/16320 (Int. App. No. PCT/AU91/00161, publication date Oct. 31, 1991) disclose anti-viral compounds that bind neuraminidase.

SUMMARY OF THE INVENTION

The objects of this invention are accomplished by compounds, or compositions comprising a compound of the formula (I) or (II):

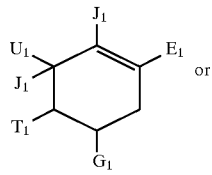

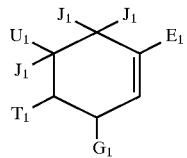

wherein $E_1$ is —$(CR_1R_1)_{m1}W_1$;

$G_1$ is $N_3$, —CN, —OH, —$OR_{6a}$, —$NO_2$, or —$(CR_1R_1)_{m1}W_2$;

$T_1$ is —$NR_1W_3$, a heterocycle, or is taken together with $U_1$ or $G_1$ to form a group having the structure

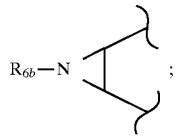

$U_1$ is H or —$X_1W_6$;

Each $J_1$ is independently H, F or Cl;

$R_1$ is H or alkyl of 1 to 6 carbon atoms;

$R_2$ is $R_3$ or $R_4$ wherein each $R_4$ is independently substituted with 0 to 3 $R_3$ groups;

$R_3$ is F, Cl, Br, I, —CN, $N_3$, —$OR_{6a}$, —$OR_1$, —$N(R_1)_2$, —$N(R_1)(R_{6b})$, —$N(R_{6b})_2$, —$SR_1$, —$SR_{6a}$, —C(O)$OR_1$, —C(O)$OR_{6a}$, —OC(O)$R_1$, —$NR_1C(O)R_1$, —$N(R_{6b})C(O)R_1$, —C(O)$N(R_1)_2$, —C(O)$N(R_{6b})(R_1)$, —C(O)$N(R_{6b})_2$, —C($NR_1$)($N(R_1)_2$), —C(N($R_{6b}$))(N($R_{6b})_2$), =O, =S, =N($R_{6b}$) or =N($R_1$);

$R_4$ is alkyl of 1 to 6 carbon atoms, alkenyl of 2 to 6 carbon atoms, or alkynyl of 2 to 6 carbon atoms, $R_5$ is $R_4$ wherein each $R_4$ is substituted with 0 to 3 $R_3$ groups;

$R_{6a}$ is H or a protecting group for hydroxyl or thio;

$R_{6b}$ is H or a protecting group for amino;

$W_1$ is a group comprising an acidic hydrogen or an $R_{6a}$-protected acidic group;

$W_2$ is a group comprising a basic heteroatom or an $R_{6b}$-protected basic heteroatom;

$W_3$ is $W_4$ or $W_5$;

$W_4$ is $R_5$ or —C(O)$R_5$, —C(O)$W_5$, —$SO_2R_5$, or —$SO_2W_5$;

$W_5$ is carbocycle or heterocycle wherein each $W_5$ is independently substituted with 0 to 3 $R_2$ groups;

$W_6$ is $R_1$, $W_5$, —C(O)$OR_{6a}$, —C(O)$NR_{6b}R_{6b}$, —C($NR_{6b}$)$NR_{6b}R_{6b}$, —C(S)$NR_{6b}R_{6b}$, —C(O)$R_1$, —$CHR_1W_7$, —CH($R_1$)$_aW_7$ or —C(O)$W_7$, where a is 0 or 1, but is 0 when $W_7$ is divalent;

$W_7$ is $R_3$ or an alkyl of 1 to 4 carbons substituted with 1 to 3 $R_3$ groups;

$X_1$ is a bond, —$CR_1R_1$—, —$(CR_1R_1)_2$—, —O—, —$NR_1$—, —$N(OR_1)$—, —$N(NR_1R_1)$—, —S—, —SO—, or —$SO_2$—; and each $m_1$ is independently an integer from 0 to 2;

and the salts, solvates, resolved enantiomers and purified diastereomers thereof.

In another embodiment of the invention a compound or composition of the invention is provided that further comprises a pharmaceutically-acceptable carrier.

In another embodiment of the invention the activity of neuraminidase is inhibited by a method comprising the step of treating a sample suspected of containing neuraminidase with a compound or composition of the invention.

In other embodiments, novel methods for synthesis of the compounds of this invention are provided.

DETAILED DESCRIPTION

Compositions of the Invention.

The compounds of this invention exclude compounds heretofore known. For purposes of the United States application, the compounds herein exclude compounds that are anticipated under 35 USC 102 or that are obvious thereover under 35 USC 103. Accordingly, the claims herein shall be construed as excluding the compounds specifically described in WO 91/16320 and in WO 92/06691, including those set forth in the background sections of these and the present applications. In one embodiment, the compounds herein exclude those in which (a) $E_1$ is —$CO_2H$, —$P(O)(OH)_2$, —$NO_2$, —$SO_2H$, —$SO_3H$, tetrazolyl, —$CH_2CHO$, —CHO, or —CH$(CHO)_2$;

(b) $G_1$ is —CN, —$NHR_{20}$, —$OR_{20}$, guanidino, —$N(R_{20})(OR_{20})$, —$N(H)(R_{20})N(R_{20})_2$, unsubstituted pyrimidinyl, or unsubstituted (pyrimidinyl)methyl;

(c) $T_1$ is —$NHR_{20}$, —$SR_{20}$, —$OR_{20}$, —$CO_2R_{20}$, —$NO_2$, —$C(R_{20})_3$, —$CH_2CO_2R_{20}$, —$CH_2NO_2$, or —$CH_2NHR_{20}$; and $R_{20}$ is H; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an $NO_2$ group, an $NH_2$ group or a COOH group;

(d) each $J_1$ is H; and (e) $X_1$ is a bond, —$CH_2$— or —$CH_2CH_2$—;

in which case $W_6$ is not H, $W_7$ or —$CH_2W_7$ wherein $W_7$ is H, —$OR_{6a}$, —$OR_1$, —$N(R_1)_2$, —$N(R_1)(R_{6b})$, —$N(R_{6b})_2$, —$SR_1$, or —$SR_{6a}$.

In another embodiment, the compounds of this invention include those in which group $U_1$ is not linked to the cyclohexene nucleus through a carbon atom. In a further embodiment, $U_1$ is not substituted with hydroxyl or hydroxyester, in particular $U_1$ is not polyhydroxyalkane, especially —CH(OH)CH(OH)$CH_2CH_2OH$.

"Heterocycle" as used herein includes by way of example and not limitation these heterocycles described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *I. Am. Chem. Soc.* 1960, 82, 5566; each of which is incorporated herein by reference.

Examples of heterocycles include by way of example and not limitation pyridyl, thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2dithiazinyl, thienyl, thianthrenyl, pyranyl, isobenzofuranyl, chromenyl, xanthenyl, phenoxathiinyl, 2H-pyrrolyl, isothiazolyl, isoxazolyl, pyrazinyl, pyridazinyl, indolizinyl, isoindolyl, 3H-indolyl, 1H-indazoly, purinyl, 4H-quinolizinyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5—pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Alkyl" as used herein typically is lower alkyl containing 1 to 6 normal, secondary, tertiary or cyclic carbon atoms such as methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), or the like.

The compositions of the invention comprise compounds of either formula:

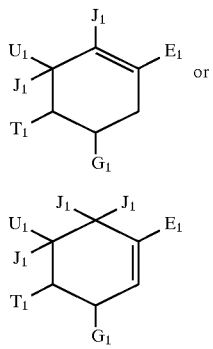

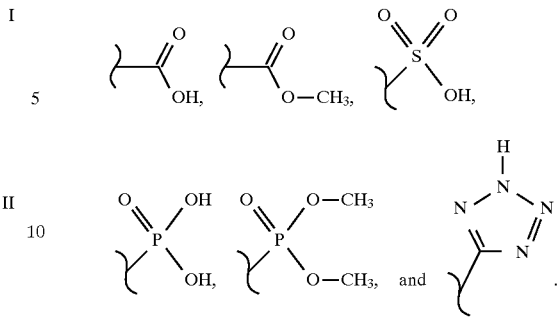

In the typical embodiment, the compounds of Formula I are chosen.

Each $J_1$ is independently H, F or Cl, typically H or F, more typically H.

$E_1$ is —$(CR_1R_1)_{m1}W_1$.

Typically, $R_1$ is H or alkyl of 1 to 6 carbon atoms, usually H or an alkyl of 1 to 4 carbon atoms, still more typically, H or an alkyl of 1 to 3 carbon atoms selected from methyl, ethyl, n-propyl, and i-propyl. Most typically $R_1$ is H.

m1 is an integer of 0 to 2, typically 0 or 1, most typically 0.

$W_1$ is a group comprising an acidic hydrogen or a protected acidic group, which, within the context of the invention, means a group having a hydrogen atom that can be removed by a base yielding an anion or its corresponding salt or solvate. The general principles of acidity and basicity of organic materials are well understood and are to be understood as defining $W_1$. They will not be detailed here. However, a description appears in Streitwieser, A.; and Heathcock, C. H.; "Introduction to Organic Chemistry, Second Edition" (Macmillan, New York, 1981), pages 60–64. Generally, acidic groups of the invention have pK values less than that of water, usually less than pK=10, typically less than pK=8, and frequently less than pK=6. They include the acids of carbon, sulfur, phosphorous and nitrogen, typically the carboxylic, sulfuric, sulfonic sulfinic, phosphoric and phosphonic acids, as well as tetrazoles.

Exemplary $E_1$ includes the organic acids, (alkCO$_2$H), carboxyl (—CO$_2$H), alkyl sulfuric (alk—O—SO$_3$H), alkyl sulfonic (alk—SO$_3$H), alkyl sulfinic (alk—SO$_2$H), alkyl phosphoric (alk—O—PO$_3$H$_2$), phosphoric (—O—PO$_3$H$_2$), alkyl phosphonic (alk—PO$_3$H$_2$), phosphonic (—PO$_3$H$_2$), and monoalkyl alkyl phosphonic acids (alk—P(O—alk)O$_2$H). Ordinarily $E_1$ is carboxy (—CO$_2$H), methylene carboxy (—CH$_2$CO$_2$H), phosphonate, methylene phosphonate (—CH$_2$PO$_3$H$_2$), sulfonate (—SO$_3$H), methylene sulfonate (—CH$_2$SO$_3$H), or tetrazole. The nomenclature of phosphorous compounds follows that of Corbridge, D. E. C. "Phosphorus. An outline of its chemistry, Biochemistry and technology." (Elsevier, New York, 1985), Appendix II, pages 731–733, and sections cited therein. $W_1$ may also be a protected acidic group, which, within the context of the invention means an acidic group as described above that has been protected by one of the groups commonly used in the art for such groups and are described below under $R_{6a}$. More typically, $W_1$ is —CO$_2$R$_1$, —SO$_3$R$_1$, —S(O)OR$_1$, —P(O)(OR$_1$)$_2$, —C(O)NHSO$_2$R$_4$, —SO$_2$NHC(O)—R$_4$ or tetrazolyl, wherein $R_1$ is defined above.

Most typically, $E_1$ is selected from the group consisting of:

Exemplary $E_1$ groups are listed in Tables 3a through 3b.

$G_1$ is $N_3$, —CN, —OH, —NO$_2$, or —$(CR_1R_1)_{m1}W_2$, wherein $R_1$ and m1 are defined above. Ordinarily, $G_1$ is —$(CR_1R_1)_{m1}W_2$.

$W_2$ is a group comprising a basic heteroatom or a protected basic heteroatom. $W_2$ generally comprises a basic heteroatom, which, within the context of the invention means an atom other than carbon which is capable of protonation, typically by an acidic hydrogen having an acidity in the range described above for $W_1$. The basic principles of basicity are described in Streitwieser and Heathcock (op. cit.) and provide meaning for the term basic heteroatom as will be understood by those ordinarily skilled in the art. Generally, the basic heteroatoms employed in the compounds of the invention have pK values for the corresponding protonated form that are in the range of values described above for $W_1$. Basic heteroatoms include the heteroatoms common in organic compounds which have an un-shared, non-bonding, n-type, or the like, electron pair. By way of example and not limitation, typical basic heteroatoms include the oxygen, nitrogen, and sulfur atoms of groups such as alcohols, amines, amidines, guanidines, sulfides, and the like, frequently, amines, amidines and guanidines. Ordinarily, $W_2$ is amino or an amino alkyl (generally lower alkyl) group such as aminomethyl, aminoethyl or aminopropyl; an amidinyl, or an amidinoalkyl group such as amidinomethyl, amidinoethyl, or amidinopropyl; or guanidinyl, or a guanidinoalkyl group such as guanidinomethyl, guanidinoethyl, or guanidinopropyl (in each instance wherein the alkyl group serves to bridge the basic substituent to the carbocyclic ring). More typically, $W_2$ is amino, amidino, guanidino, heterocycle, heterocycle substituted with 1 or 2 amino or guanidino groups (usually 1), or an alkyl of 2 to 3 carbon atoms substituted with amino or guanidino, or such alkyl substituted with an amino and a second group selected from the group consisting of hydroxy and amino. The heterocycles useful as $W_2$ include typically N or S-containing 5 or 6 membered rings, wherein the ring contains 1 or 2 heteroatoms. Such heterocycles generally are substituted at ring carbon atoms. They may be saturated or unsaturated and may be linked to the core cyclohexene by lower alkyl (m1=1 or 2) or by —NR$_1$—. Still more typically, $W_2$ is —NHR$_1$, —C(NH) (NH$_2$), —NR1—C(NR$_1$)(NR$_1$R$_3$), —NH—C(NH)(NHR$_3$), —NH—C(NH)(NHR$_1$), —NH—C(NH)NH$_2$, —CH(CH$_2$NHR$_1$)(CH$_2$OH), —CH(CH$_2$NHR$_1$)(CH$_2$NHR$_1$), —CH(NHR$_1$)—(CR$_1$R$_1$)$_{m2}$—CH(NHR$_1$)R$_1$, —CH(OH)—(CR$_1$R$_1$)$_{m2}$—CH(NHR$_1$)R$_1$, or —CH(NHR$_1$)—(CR$_1$R$_1$)$_{m2}$—CH(OH)R$_1$, —(CR$_1$R$_1$)$_{m2}$—S—C(NH)NH$_2$, —N=C(NHR$_1$)(R$_3$), —N=C(SR$_1$)N(R$_1$)$_2$, —N(R$_1$)C(NH)N(R$_1$)C=N, or —N=C(NHR$_1$)(R$_1$); wherein each m2 is independently an integer from 0 to 1, and ordinarily $R_1$ is H and $R_3$ is C(O)N(R$_1$)$_2$.

W₂ optionally is a protected basic heteroatom which within the context of the invention means a basic heteroatom as described above that has been protected by $R_{6b}$ such as one of the groups common in the art. Such groups are described in detail in Greene (op. cit.) as set forth below. Such groups include by way of example and not limitation, amides, carbamates, amino acetals, imines, enamines, N-alkyl or N-aryl phosphinyls, N-alkyl or N-aryl sulfenyls or sulfonyls, N-alkyl or N-aryl silyls, thioethers, thioesters, disulfides, sulfenyls, and the like. In some embodiments, the protecting group $R_{6b}$ will be cleavable under physiological conditions, typically it will be cleavable in vivo where, for example, the basic heteroatom forms an amide with an organic acid or an amino acid such as a naturally occurring amino acid or a polypeptide as described below for the $R_{6a}$ group. Alternatively, the acid or a polypeptide as described below for the $R_{6a}$ group. Alternatively, the $R_1COOH$.

Typically $G_1$ is selected from the group consisting of:

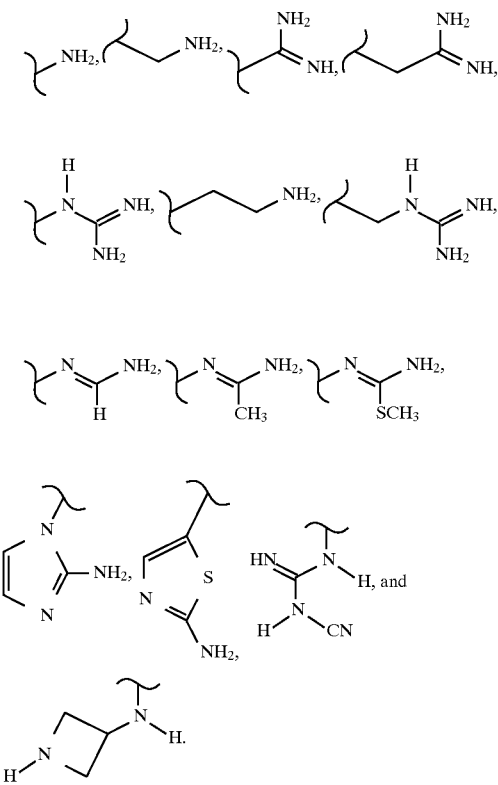

Further exemplary $G_1$ groups are listed in Tables 4a–4c.

$T_1$ is —NR₁W₃ or heterocycle, wherein $R_1$ and $W_3$ are defined above. As noted, $W_3$ is $W_4$ or $W_5$, wherein $W_4$ is $R_1$ or —C(O)R₅, —C(O)W₅, —SO₂R₅, or —SO₂W₅. Typically, $W_3$ is —C(O)R₅ or $W_5$.

$R_5$ is $R_4$, as defined below, or $R_4$ substituted with 0 to 3 $R_3$ groups. Typically $R_5$ is an alkyl of 1 to 4 carbon atoms substituted with 0 to 3 fluorine atoms.

$R_3$ is F, Cl, Br, I, —CN, N₃, —OR₆ₐ, —OR₁, —N(R₁)₂, —N(R₁)(R₆ᵦ), —N(R₆ᵦ)₂, —SR₁, —SR₆ₐ, —C(O)OR₁, —C(O)OR₆ₐ, —OC(O)R₁, —NR₁C(O)R₁, —N(R₆ᵦ)C(O)R₁, —C(O)N(R₁)₂, —C(O)N(R₆ᵦ)(R₁), —C(O)N(R₆ᵦ)₂, —C(NR₁)(N(R₁)₂), —C(N(R₆ᵦ))(N(R₆ᵦ)₂), =O, =S, =N(R₆ᵦ) or =N(R₁). Typically $R_3$ is F, Cl, —CN, N₃, —OR₁, —N(R₁)₂, —SR₁, —C(O)OR₁, —OC(O)R₁, or =O. More typically, $R_3$ is F, —OR₁, —N(R₁)₂, or =O. In the context of the present application, "=O" denotes a double bonded oxygen atom (oxo), and "=S" =N(R₆ᵦ) and "=N(R₁)" denote the sulfur and nitrogen analogs.

$R_4$ is alkyl, alkynyl or alkenyl of 2 to 6 carbon atoms. $R_4$ ordinarily is alkyl (as defined above). When $R_4$ is alkenyl it is typically ethenyl (—CH=CH₂), 1-prop-1-enyl (—CH=CHCH₃), 1-prop-2-enyl (—CH₂CH=CH₂), 2-prop-1-enyl (—C(=CH₂)(CH₃)), 1-but-1-enyl (—CH=CHCH₂CH₃), 1-but-2-enyl (—CH₂CH=CHCH₃), 1-but-3-enyl (—CH₂CH₂CH=CH₂), 2-methyl-1-prop-1-enyl (—CH=C(CH₃)₂), 2-methyl-1-prop-2-enyl (—CH₂C(=CH₂)(CH₃)), 2-but-1-enyl (—C(=CH₂)CH₂CH₃), 2-but-2-enyl (—C(CH₃)=CHCH₃), 2-but-3-enyl (—CH(CH₃)CH=CH₂), 1-pent-1-enyl (—C=CHCH₂CH₂CH₃), 1-pent-2-enyl (—CHCH=CHCH₂CH₃), 1-pent-3-enyl (—CHCH₂CH=CHCH₃), 1-pent-4-enyl (—CHCH₂CH₂CH=CH₂), 2-pent-1-enyl (—C(=CH₂)CH₂CH₂CH₃), 2-pent-2-enyl (—C(CH₃)=CH₂CH₂CH₃), 2-pent-3-enyl (—CH(CH₃)CH=CHCH₃), 2-pent-4-enyl (—CH(CH₃)CH₂CH=CH₂) or 3-methyl-1-but-2-enyl (—CH₂CH=C(CH₃)₂). More typically, $R_4$ alkenyl groups are of 2, 3 or 4 carbon atoms. When $R_4$ is alkynyl it is typically ethynyl (—CCH), 1-prop-1-ynyl (—CCCH₃), 1-prop-2-ynyl (—CH₂CCH), 1-but-1-ynyl (—CCCH₂CH₃), 1-but-2-ynyl (—CH₂CCCH₃), 1-but-3-ynyl (—CH₂CH₂CCH), 2-but-3-ynyl (CH(CH₃)CCH), 1-pent-1-ynyl (—CCCH₂CH₂CH₃), 1-pent-2-ynyl (—CH₂CCCH₂CH₃), 1-pent-3-ynyl (—CH₂CH₂CCCH₃) or 1-pent-4-ynyl (—CH₂CH₂CH₂CCH). More typically, $R_4$ alkynyl groups are of 2, 3 or 4 carbon atoms.

$W_5$ is a carbocycle or heterocycle, with the proviso that each $W_5$ is independently substituted with 0 to 3 $R_2$ groups, wherein $R_2$ is $R_3$ or $R_4$, with the proviso that each $R_4$ is independently substituted with 0 to 3 $R_3$ groups;

$W_5$ carbocycles and $T_1$ and $W_5$ heterocycles are stable chemical structures. Such structures are isolatable in measurable yield, with measurable purity, from reaction mixtures at temperatures from —78° C. to 200° C. Each $W_5$ is independently substituted with 0 to 3 $R_2$ groups. Typically, $T_1$ and $W_5$ are a saturated, unsaturated or aromatic ring comprising a mono- or bicyclic carbocycle or heterocycle. More typically, $T_1$ or $W_5$ has 3 to 10 ring atoms, still more typically, 3 to 7 ring atoms, and ordinarily 3 to 6 ring atoms. The $T_1$ and $W_5$ rings are saturated when containing 3 ring atoms, saturated or monounsaturated when containing 4 ring atoms, saturated, or mono- or diunsaturated when containing 5 ring atoms, and saturated, mono- or diunsaturated, or aromatic when containing 6 ring atoms.

When $W_5$ is carbocyclic, it is typically a 3 to 7 carbon monocycle or a 7 to 10 carbon atom bicycle. More typically, $W_5$ monocyclic carbocycles have 3 to 6 ring atoms, still more typically 5 or 6 ring atoms. $W_5$ bicyclic carbocycles have 7 to 10 ring atoms arranged as a bicyclo [4,5], [5,5], [5,6] or [6,6] system, still more typically, 9 or 10 ring atoms arranged as a bicyclo [5,6] or [6,6] system. Examples include cyclopropyl, cyclobutyl, cyclopentyl, 1-cyclopent-1-enyl, 1cyclopent-2-enyl, 1-cyclopent-3-enyl, cyclohexyl, 1-cyclohex-1-enyl, 1-cyclohex-2-enyl, 1-cyclohex-3-enyl, phenyl, and naphthyl.

A $T_1$ or $W_5$ heterocycle is typically a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S). More typically, $T_1$ and $W_5$ heterocyclic monocycles have 3 to 6 ring atoms (2 to 5 carbon atoms and 1 to 2 heteroatoms selected from N, O, and S), still more typically, 5 or 6 ring atoms (3 to 5 carbon atoms and 1 to 2 heteroatoms selected from N and S). $T_1$ and $W_5$ heterocyclic bicycles have 7 to 10 ring atoms (6 to 9 carbon atoms and 1 to 2 heteroatoms selected from N, O, and S) arranged as a bicyclo [4,5], [5,5], [5,6], or [6,6]

system, still more typically, 9 to 10 ring atoms (8 to 9 carbon atoms and 1 to 2 hetero atoms selected from N and S) arranged as a bicyclo [5,6] or [6,6] system.

Typically $T_1$ and $W_5$ heterocycles are selected from pyridyl, pyridazinyl, pyrimidinyl, pyrazinyl, s-triazinyl, oxazolyl, imidazolyl, thiazolyl, isoxazolyl, pyrazolyl, isothiazolyl, furanyl, thiofuranyl, thienyl, or pyrrolyl.

More typically, the heterocycle of $T_1$ and $W_5$ is bonded through a carbon atom or nitrogen atom thereof. Still more typically $T_5$ heterocycles are bonded by a stable covalent bond through a nitrogen atom thereof to the cyclohexene ring of the compositions of the invention and $W_5$ heterocycles are bonded by a stable covalent bond through a carbon or nitrogen atom thereof to the cyclohexene ring of the compositions of the invention. Stable covalent bonds are chemically stable structures as described above.

Typically $W_5$ is selected from the group consisting of:

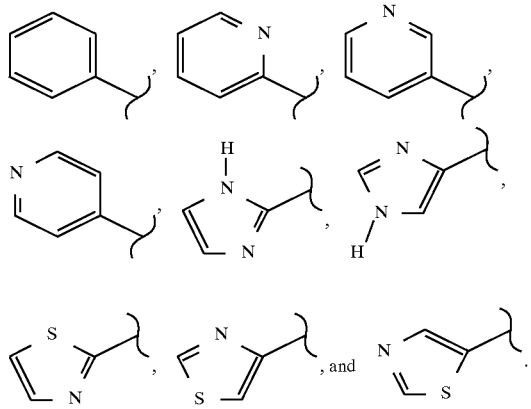

Generally $T_1$ is selected from the group consisting of:

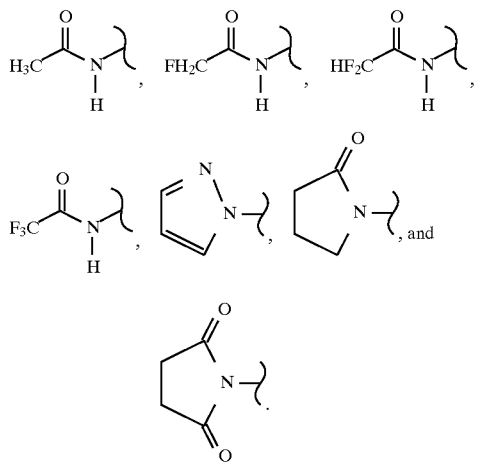

Exemplary $T_5$ groups are listed in Tables 5a–5d.

$U_1$ is H or —$X_1W_6$, but typically the latter. $X_1$ is a bond, —$CR_1R_1$—, —$(CR_1R_1)_2$—, —O—, —$NR_1$—, —$N(OR_1)$—, —$N(NR_1R_1)$—, —S—, —SO—, or —$SO_2$—while $W_6$ is $R_1$, $W_5$, —$CO_2R_{6a}$, —$C(O)NR_{6b}R_{6b}$, —$C(NR_{6b})NR_{6b}R_{6b}$, —$C(S)NR_{6b}R_{6b}$, —$C(O)R_1$, —$CHR_1W_7$, —$CH(R_1)_aW_7$ (where a is 0 or 1, but is 0 when $W_7$ is divalent) or —$C(O)W_7$, wherein $W_7$ is $R_3$ or an alkyl of 1 to 4 carbons substituted with 1 to 3 $R_3$ groups, typically selected from the group consisting of —$NR_1(R_{6b})$, —$N(R_{6b})_2$, —$OR_{6a}$, or $SR_{6a}$. More typically, $U_1$ is —O—$CHR_1W_7$.

Ordinarily $X_1$ is —O—, —NH—, —S—, —SO—, or —$SO_2$—, and $W_6$ is —$CHR_1W_7$ or —$C(O)W_7$. More typically, $W_7$ is —$OR_1$ or an alkyl of 1 to 2 carbon atoms and is substituted with 1 to 2 hydroxy groups.

In general, $U_1$ is selected from $R_1O$— and $R_1OR_1O$— (where only the terminal $R_1$ can be H) and the group consisting of:

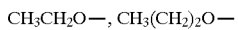

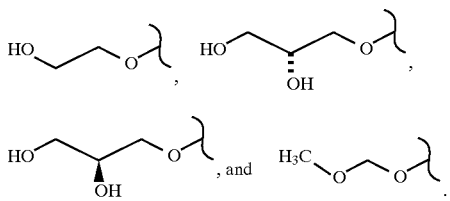

Exemplary $U_1$ groups are listed in Tables 2a–2h.

An embodiment of the invention comprises a compound of the formula:

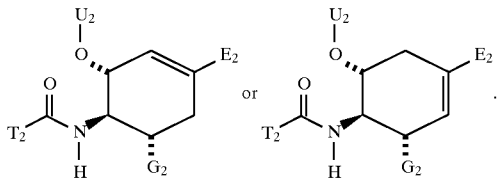

wherein $E_2$ is $E_1$, but is typically selected from the group consisting of:

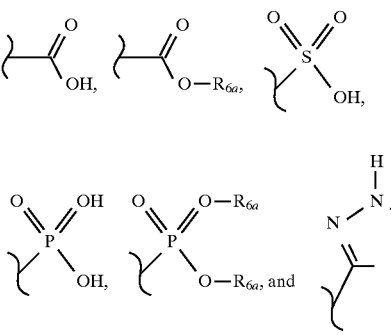

and wherein $G_2$ is $G_1$, but is typically selected from the group consisting of:

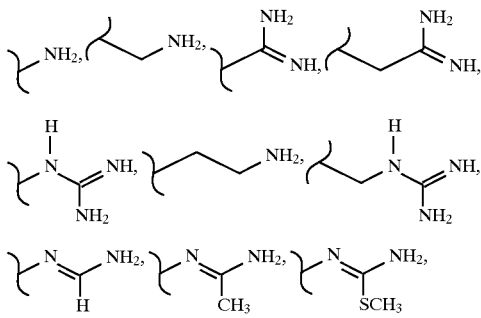

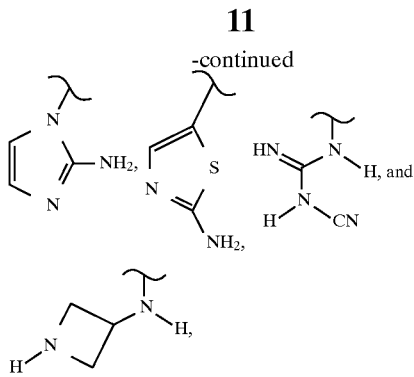

and wherein $T_2$ is $R_4$ or $R_5$. Generally, $T_2$ is alkyl of 1 to 2 carbon atoms substituted with 0 to 3 fluorine atoms.

$U_2$ is one of:

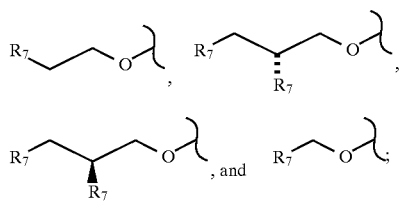

wherein $R_7$ is H, —OCH$_3$, —OAc (—O—C(O)CH$_3$), —OH, —NH$_2$, or —SH.

Groups $R_{6a}$ and $R_{6b}$ are not critical functionalities and may vary widely. $R_{6a}$ when other than H, typically is bound to any acidic group such as, by way of example and not limitation, a —CO$_2$H or —C(S)OH group, thereby functioning as an ester-, thioester, thioamide-, or amide-forming group as in a —CO$_2R_{6a}$, —C(O)N($R_{6a}$)$_2$, —C(O)N($R_{6a}$)(R$_1$), —C(S)OR$_{6a}$, —C(S)N($R_{6a}$)$_2$, or —C(S)N($R_{6a}$)(R$_1$) group. $R_{6a}$ for example includes the ester or amide forming groups of WO 95/07920. Examples of $R_{6a}$ include $C_3$–$C_6$ aryl (including phenyl, 2- and 3-pyrrolyl, 2- and 3-thienyl, 2- and 4-imidazolyl, 2-, 4- and 5-oxazoly, 3- and 4-isoxazolyl, 2-, 4- and 5-thiazolyl, 3-, 4- and 5-isothiazolyl, 3- and 4-pyrazolyl, 1-, 2-, 3- and 4-pyridinyl, and 1-, 2-, 4- and 5-pyrimidinyl), $C_3$–$C_6$ aryl substituted with halo, alkyl $C_1$–$C_{12}$ alkoxy, CN, NO$_2$, OH, carboxy, carboxyester, thiol, thiolester, $C_1$–$C_{12}$ haloalkyl (1–6 halogen atoms), $C_2$–$C_{12}$ alkenyl or $C_2$–$C_{12}$ alkynyl [including 2-, 3- and 4-alkoxyphenyl ($C_1$–$C_{12}$ alkyl), 2, -3-and 4-methoxyphenyl, 2-, 3- and 4-ethoxyphenyl, 2,3-, 2,4-, 2,5-, 2,6-, 3,4- and 3,5-diethoxyphenyl, 2- and 3-carboethoxy-4-hydroxyphenyl, 2- and 3-ethoxy-4-hydroxyphenyl, 2- and 3-ethoxy-5-hydroxyphenyl, 2- and 3-ethoxy-6-hydroxyphenyl, 2-, 3- and 4-O-acetylphenyl, 2-, 3- and 4dimethylaminophenyl, 2-, 3- and 4-methylmercaptophenyl, 2-, 3- and 4halophenyl (including 2-, 3- and 4-fluorophenyl and 2-, 3- and 4chlorophenyl], 2,3-, 2,4-, 2,5-, 2,6-, 3,4- and 3,5-dimethylphenyl, 2,3-, 2,4-, 2,5-, 2,6-, 3,4- and 3,5-biscarboxyethylphenyl, 2,3-, 2,4-, 2,5-, 2,6-, 3,4- and 3,5-dimethoxyphenyl, 2,3-, 2,4-, 2,5-, 2,6-, 3,4- and 3,5-dihalophenyl (including 2,4difluorophenyl and 3,5-difluorophenyl), 2-, 3- and 4-haloalkylphenyl (1 to 5 halogen atoms, $C_1$–$C_{12}$ alkyl including 4-trifluoromethylphenyl), 2-, 3- and 4-cyanophenyl, 2-, 3- and 4-nitrophenyl, 2-, 3- and 4-haloalkylbenzyl (1 to 5 halogen atoms, $C_1$–$C_{12}$ alkyl including 4-trifluoromethylbenzyl and 2-, 3- and 4-trichloromethylphenyl and 2-, 3- and 4-trichloromethylphenyl), 4-N-methylpiperidinyl, 3-N-methylpiperidinyl, 1-ethylpiperazinyl, benzyl, alkylsalicylphenyl ($C_{1-C4}$ alkyl, including 2-, 3- and 4-ethylsalicylphenyl), 2-,3and 4-acetylphenyl, 1,8-dihydroxynaphthyl (—O—$C_{10}H_6$—OH) and aryloxy ethyl [$C_6$–$C_9$ aryl (including phenoxy ethyl)], 2,2'-dihydroxybiphenyl, alkoxy ethyl [$C_1$–$C_6$ alkyl including —CH$_2$—CH$_2$—O—CH$_3$ (methoxy ethyl)], alkyl substituted by OH or by 1 to 3 halo atoms (including —CH$_3$, —CH(CH$_3$)$_2$, —C(CH$_3$)$_3$, —CH$_2$CH$_3$, —(CH$_2$)$_2$CH$_3$, —(CH$_2$)$_3$CH$_3$, —(CH$_2$)$_4$CH$_3$, —(CH$_2$)$_5$CH$_3$, —CH$_2$CH$_2$F, —CH$_2$CH$_2$Cl, —CH$_2$CF$_3$, and —CH$_2$CCl$_3$), 2-, 3- and 4-N,N-dialkylaminophenol, —C$_6$H$_4$CH$_2$—N(CH$_3$)$_2$,

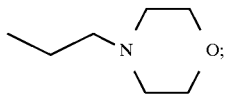

-N-2-propylmorpholino, 2,3-dihydro-6-hydroxyindene, sesamol, catechol monoester, —CH$_2$—C(O)—N(R$^8$)$_2$ wherein each R$^8$ is the same or different H or $C_1$–$C_4$ alkyl, —CH$_2$—S(O)(R$^8$), —CH$_2$—S(O)$_2$(R$^8$), —CH$_2$—CH(OC(O)CH$_2$R$^8$)—CH$_2$(OC(O)CH$_2$R$^8$), cholesteryl, a 5 or 6 carbon monosaccharide, disaccharide or oligosaccharide (3 to 9 monosaccharide residues), enolpyruvate (HOOCC—C(=CH$_2$)O), glycerol, α-D-β-diglycerides (wherein the fatty acids composing glyceride lipids generally are naturally occurring saturated or unsaturated $C_{6-26}$, $C_{6-18}$ or $C_{6-10}$ fatty acids such as linoleic, lauric, myristic, palmitic, stearic, oleic, palmitoleic, linolenic and the like fatty acids), trimethoxybenzyl, triethoxybenzyl, 2-alkyl pyridinyl ($C_{1-4}$ alkyl),

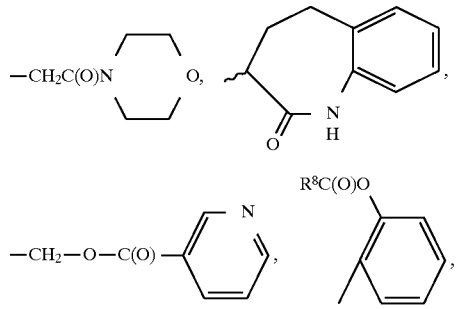

$C_1$–$C_4$ alkylene-$C_3$–$C_6$ aryl (including benzyl, —CH$_2$-pyrrolyl, —CH$_2$-thienyl, —CH$_2$-imidazolyl, —CH$_2$-oxazolyl, —CH$_2$-isoxazolyl, —CH$_2$-thiazolyl, —CH$_2$-isothiazolyl, —$_2$-pyrazolyl, —CH$_2$-pyridinyl and —CH$_2$-pyrimidinyl) substituted in the aryl moiety by 3 to 5 halogen atoms or 1 to 2 atoms or groups selected from halogen, $C_1$–$C_{12}$ alkoxy (including methoxy and ethoxy), cyano, nitro, OH, $C_1$–$C_{12}$ haloalkyl (1 to 6 halogen atoms; including —CH$_2$—CCl$_3$), $C_1$–$C_{12}$ alkyl (including methyl and ethyl), $C_2$–$C_{12}$ alkenyl or $C_2$–$C_{12}$ alkynyl, and other compounds set forth in Table B below. The hydroxyl groups of the compounds of this invention optionally are substituted with one of groups III, IV or V disclosed in WO094/21604, or with isopropyl.

Particularly useful $R_{6a}$ groups are alkylacyloxymethyl groups and their derivatives, including —CH(CH$_2$CH$_2$OCH$_3$)OC(O)C(CH$_3$)$_3$,

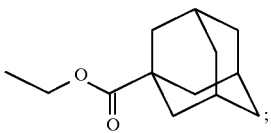

—CH$_2$OC(O)C$_{10}$H$_{15}$, —CH$_2$OC(O)C(CH$_{33}$, —CH(CH$_2$OCH$_3$)OC(O)C(CH$_3$)$_3$, —CH(CH(CH$_3$)$_2$)OC(O)C(CH$_3$)$_3$, —CH$_2$OC(O)CH$_2$CH(CH$_3$)$_2$, —CH$_2$OC(O)C$_6$H$_{11}$, —CH$_2$OC(O)C$_6$H$_5$, —CH$_2$OC(O)C$_{10}$H$_{15}$, —CH$_2$OC(O)CH$_2$CH$_3$, —CH$_2$OC(O)CH(CH$_3$)$_2$, —CH$_2$OC(O)C(CH$_3$)$_3$ and —CH$_2$OC(O)CH$_2$C$_6$H$_5$.

R$_{6a}$ and R$_{6b}$ groups optionally are used to prevent side reactions with the protected group during synthetic procedures, so they can function as protecting groups (PRT) during synthesis. For the most part the decision as to which groups to protect, when to do so, and the nature of the PRT will be dependent upon the chemistry of the reaction to be protected against (e.g., acidic, basic, oxidative, reductive or other conditions) and the intended direction of the synthesis. The PRT groups do not need to be, and generally are not, the same if the compound is substituted with multiple PRT. In general, PRT will be used to protect carboxyl, hydroxyl or amino groups. The order of deprotection to yield free groups is dependent upon the intended direction of the synthesis and the reaction conditions to be encountered, and may occur in any order.

A very large number of R$_{6a}$ hydroxy protecting groups and corresponding chemical cleavage reactions are described in "Protective Groups in Organic Chemistry", Theodora W. Greene John Wiley & Sons, Inc., New York, 1991, ISBN 0-471-62301-6) ("Greene"). See also Kocienski, Philip J.; "Protecting Groups" (Georg Thieme Verlag Stuttgart, New York, 1994), which is incorporated by reference in its entirety herein. In particular Chapter 1, Protecting Groups: An Overview, pages 1–20, Chapter 2, Hydroxyl Protecting Groups, pages 21–94, Chapter 3, Diol Protecting Groups, pages 95–117, Chapter 4, Carboxyl Protecting Groups, pages 118–154, Chapter 5, Carbonyl Protecting Groups, pages 155–184.

Typical R$_{6a}$ hydroxy protecting groups are described in Greene at pages 14–118 and include Ethers (Methyl); Substituted Methyl Ethers (Methoxymethyl, Methylthiomethyl, t-Butylthiomethyl, (Phenyldimethylsilyl)methoxymethyl, Benzyloxymethyl, p-Methoxybenzyloxymethyl, (4-Methoxyphenoxy)methyl, Guaiacolmethyl, t-Butoxymethyl, 4-Pentenyloxymethyl, Siloxymethyl, 2-Methoxyethoxymethyl, 2,2,2-Trichloroethoxymethyl, Bis(2-chloroethoxy)methyl, 2-(Trimethylsilyl)ethoxymethyl, Tetrahydropyranyl, 3-Bromotetrahydropyranyl, Tetrahydrothiopyranyl, 1-Methoxycyclohexyl, 4-Methoxytetrahydropyranyl, 4-Methoxytetrahydrothiopyranyl, 4-Methoxytetrahydrothiopyranyl S,S-Dioxido, 1-[(2-Chloro-4-methyl)phenyl]4-methoxypiperidin-4-yl, 35, 1,4-Dioxan-2-yl, Tetrahydrofuranyl, Tetrahydrothiofuranyl, 2,3,3a,4,5,6,7,7a-Octahydro-7,8,8-trimethyl-4,7-methanobenzofuran-2-yl)); Substituted Ethyl Ethers (1-Ethoxyethyl, 1-(2-Chloroethoxy)ethyl, 1-Methyl-1-methoxyethyl, 1-Methyl-1-benzyloxyethyl, 1-Methyl-1-benzyloxy-2-fluoroethyl, 2,2,2-Trichloroethyl, 2-Trimethylsilylethyl, 2-(Phenylselenyl)ethyl, t-Butyl, Allyl, p-Chlorophenyl, p-Methoxyphenyl, 2,4-Dinitrophenyl, Benzyl); Substituted Benzyl Ethers (p-Methoxybenzyl, 3,4-Dimethoxybenzyl, o-Nitrobenzyl, p-Nitrobenzyl, p-Halobenzyl, 2,6-Dichlorobenzyl, p-Cyanobenzyl, p-Phenylbenzyl, 2- and 4-Picolyl, 3-Methyl-2-picolyl N-Oxido, Diphenylmethyl, p,p'-Dinitrobenzhydryl, 5-Dibenzosuberyl, Triphenylmethyl, α-Naphthyldiphenylmethyl, p-methoxyphenyldiphenylmethyl, Di(p-methoxyphenyl)phenylmethyl, Tri(p-methoxyphenyl)methyl, 4-(4'-Bromophenacyloxy)phenyldiphenylmethyl, 4,4', 4"-Tris(4,5-dichlorophthalimidophenyl)methyl, 4,4', 4"-Tris(levulinoyloxyphenyl)methyl, 4,4', 4"-Tris(benxoyloxyphenyl)methyl, 3-(Imidazol-1-ylmethyl)bis(4', 4"-dimethoxyphenyl)methyl, 1,1-Bis(4-methoxyphenyl)-1'-pyrenylmethyl, 9-Anthryl, 9-(9-Phenyl)xanthenyl, 9-(9-Phenyl-10-oxo)anthryl, 1,3-Benzodithiolan-2-yl, Benzisothiazolyl S,S-Dioxido); Silyl Ethers (Trimethylsilyl, Triethylsilyl, Triisopropylsilyl, Dimethylisopropylsilyl, Diethylisopropylsily, Dimethylthexylsilyl, t-Butyldimethylsilyl, t-Butyldiphenylsilyl, Tribenzylsilyl, Tri-p-xylylsilyl, Triphenylsilyl, Diphenylmethylsilyl, t-Butylmethoxyphenylsilyl); Esters (Formate, Benzoylformate, Acetate, Choroacetate, Dichloroacetate, Trichloroacetate, Trifluoroacetate, Methoxyacetate, Triphenylmethoxyacetate, Phenoxyacetate, p-Chlorophenoxyacetate, p-poly-Phenylacetate, 3-Phenylpropionate, 4-Oxopentanoate (Levulinate), 4,4 (Ethylenedithio)pentanoate, Pivaloate, Adamantoate, Crotonate, 4-Methoxycrotonate, Benzoate, p-Phenylbenzoate, 2,4,6-Trimethylbenzoate (Mesitoate)); Carbonates (Methyl, 9-Fluorenylmethyl, Ethyl, 2,2,2-Trichloroethyl, 2-(Trimethylsilyl)ethyl, 2-(Phenylsulfonyl)ethyl, 2-(Triphenylphosphonio)ethyl, Isobutyl, Vinyl, Allyl, p-Nitrophenyl, Benzyl, p-Methoxybenzyl, 3,4-Dimethoxybenzyl, o-Nitrobenzyl, p-Nitrobenzyl, S-Benzyl Thiocarbonate, 4-Ethoxy-1-naphthyl, Methyl Dithiocarbonate); Groups With Assisted Cleavage (2-Iodobenzoate, 4-Azidobutyrate, 4-Niotro-4-methylpentanoate, o-(Dibromomethyl)benzoate, 2-Formylbenzenesulfonate, 2-(Methylthiomethoxy)ethyl Carbonate, 4-(Methylthiomethoxy)butyrate, 2-(Methylthiomethoxymethyl)benzoate); Miscellaneous Esters (2,6-Dichloro-4-methylphenoxyacetate, 2,6-Dichloro-4-(1,1,3,3tetramethylbutyl)phenoxyacetate, 2,4-Bis(1,1-dimethylpropyl)phenoxyacetate, Chorodiphenylacetate, Isobutyrate, Monosuccinoate, (E)-2-Methyl-2-butenoate (Tigloate), o-(Methoxycarbonyl)benzoate, p-poly-Benzoate, α-Naphthoate, Nitrate, Alkyl N,N,N',N'-Tetramethylphosphorodiamidate, N-Phenylcarbamate, Borate, Dimethylphosphinothioyl, 2,4-Dinitrophenylsulfenate); and Sulfonates (Sulfate, Methanesulfonate (Mesylate), Benzylsulfonate, Tosylate).

More typically, R$_{6a}$ hydroxy protecting groups include substituted methyl ethers, substituted benzyl ethers, silyl ethers, and esthers including sulfonic acid esters, still more typically, trialkylsilyl ethers, tosylates and acetates.

Typical 1,2-diol protecting groups (thus, generally where two OH groups are taken together with the R$_{6a}$ protecting functionality) are described in Greene at pages 118–142 and include Cyclic Acetals and Ketals (Methylene, Ethylidene, 1-t-Butylethylidene, 1-Phenylethylidene, (4-Methoxyphenyl)ethylidene, 2,2,2-Trichloroethylidene, Acetonide (Isopropylidene), Cyclopentylidene, Cyclohexylidene, Cycloheptylidene, Benzylidene, p-Methoxybenzylidene, 2,4-Dimethoxybenzylidene, 3,4-Dimethoxybenzylidene, 2-Nitrobenzylidene); Cyclic Ortho Esters (Methoxymethylene, Ethoxymethylene, Dimethoxymethylene, 1-Methoxyethylidene, 1-Ethoxyethylidine, 1,2-Dimethoxyethylidene, α-Methoxybenzylidene, 1-(N,N-Dimethylamino)ethylidene Derivative, α-(N,N-Dimethylamino)benzylidene Derivative, 2-Oxacyclopentylidene); Silyl Derivatives (Di-t-butylsilylene Group, 1,3-(1,1,3,3-Tetraisopropyldisiloxanylidene), and Tetra-t-butoxydisiloxane-1,3-diylidene), Cyclic Carbonates, Cyclic Boronates, Ethyl Boronate and Phenyl Boronate.

More typically, 1,2-diol protecting groups include those shown in Table A, still more typically, epoxides, acetonides, cyclic ketals and aryl acetals.

TABLE A

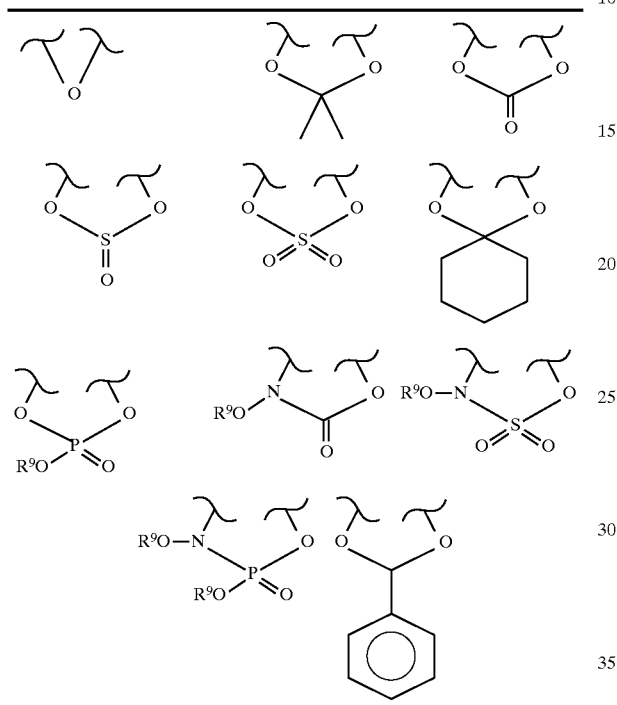

wherein $R^9$ is $C_1–C_6$ alkyl.

Carboxyl or phosphonic acids also are reacted with amino-containing compounds to form amides, as in —C(O)Y, —P(O)(Y)$_2$ or —P(O)(OH)(Y), where Y=$R_{6a}$ Alternatively, residues of amino acids are useful as $R_{6b}$ groups in that the carboxyl functionality can be used to amidate amines, as are found for instance in group $G_1$. Y may be an amine or an amino acid residue. In general, the amino acid residue has the structure $R^{11}OC(O)CH(R_{10})$NH—, where $R_{11}$ is another $R_{6a}$, one or more additional amino acid residues linked via peptide bonds, or H and $R^{10}$ is lower alkyl or lower alkyl ($C_1–C_6$) substituted with amino, carboxyl, amide, carboxyl ester, hydroxyl, $C_6–C_7$ aryl, guanidinyl, imidazolyl, indolyl, sulfhydryl, sulfoxide, and/or alkylphosphate. Ordinarily $R_{11}$ is $R_{6a}$ and $R^{10}$ is a side chain of a naturally occurring amino acid. With respect to the carboxyl-containing side chains it will be understood that if the C atom of the subject carboxyl is linked by 5 or less atoms to the phosphoamide N then the carboxyl optionally will be blocked, e.g. by esterification with $R_{6a}$ or amidation wherein the ester or amide bonds are hydrolyzable. $R^{10}$ also is taken together with the amino acid α N to form a proline residue ($R^{10}$=—CH$_2$)$_3$—). However, $R^{10}$ is generally a side group such as H, —CH$_3$, —CH(CH$_3$)$_2$, —CH$_2$—CH(CH$_3$)$_2$, —CHCH$_3$—CH$_2$—CH$_3$, —CH$_2$—C$_6$H$_5$, —CH$_2$CH$_2$—S—CH$_3$, —CH$_2$OH, —CH(OH)—CH$_3$, —CH$_2$SH, —CH$_2$—C$_6$H$_4$OH, —CH$_2$—CO—NH$_2$, —CH$_2$—CH$_2$—CO—NH$_2$, —CH$_2$—COOH, —CH$_2$—CH$_2$—COOH, —(CH$_2$)$_4$—NH$_2$ and —(CH$_2$)$_3$—NH—C(NH$_2$)—NH$_2$. $R^{10}$ also includes 1-guanidinoprop-3-yl, benzyl, 4-hydroxybenzyl, imidazol-4-yl, indol-3-yl, methoxyphenyl and ethoxyphenyl.

When the amino acid residue contains one or more chiral centers, any of the D, L, meso, threo or erythro (as appropriate) racemates, scalemates or mixtures thereof may be used as group Y. In general, if the intermediates are to be hydrolyzed non-enzymatically (as would be the case where the compounds are used as chemical intermediates for the free acids), D isomers are useful. On the other hand, L isomers are more versatile since they can be susceptible to both non-enzymatic and enzymatic hydrolysis, and are more efficiently transported by amino acid or dipeptidyl transport systems in the gastrointestinal tract.

Examples of suitable $R_{6a}$ amino acid residues include the following:

Glycyl;

Aminopolycarboxylic acids, e.g., aspartic acid, β-hydroxyaspartic acid, glutamic acid, β-hydroxyglutamic acid, β-methylaspartic acid, β-methylglutamic acid, β,β-dimethylaspartic acid, γ-hydroxyglutamic acid, β,γ-dihydroxyglutamic acid, β-phenylglutamic acid, γ-methyleneglutamic acid, 3-aminoadipic acid, 2-aminopimelic acid, 2-aminosuberic acid and 2-aminosebacic acid residues;

Amino acid amides such as glutaminyl and asparaginyl;

Polyamino- or polybasic-monocarboxylic acids such as arginine, lysine, β-aminoalanine, γ-aminobutyrine, ornithine, citruline, homoarginine, homocitrulline, 5-hydroxy-2,6-diaminohexanoic acid (commonly, hydroxylysine, including allohydroxylysine), diaminobutyric and histidine residues;

Diaminodicarboxylic acids such as α,α'-diaminosuccinic acid, α,α'-diaminoglutaric acid, α,α'-diaminoadipic acid, α,α'-diaminopimelic acid, α,α'-diamino-β-hydroxypimelic acid, α,α'-diaminosuberic acid, α,α'-diaminoazelaic acid, and α,α'-diaminosebacic acid residues;

Imino acids such as proline, 4- or 3-hydroxy-2-pyrrolidinecarboxylic acid (commonly, hydroxyproline, including allohydroxyproline), γ-methylproline, pipecolic acid, 5-hydroxypipecolic acid, —N([CH$_2$]$_{m1}$COOR$^6$)$_2$, wherein m1 and $R_6$ are as defined above, and azetidine-2-carboxylic acid residues;

A mono- or di-alkyl (typically $C_1$ –$C_8$ branched or normal) amino acid such as alanine, valine, leucine, allylglycine, butyrine, norvaline, norleucine, heptyline, α-methylserine, α-amino-α-methyl-γ-hydroxyvaleric acid, α-amino-α-methyl-δ-hydroxyvaleric acid, α-amino-α-methyl-ε-hydroxycaproic acid, isovaline, α-methylglutamic acid, α-aminoisobutyric acid, α-aminodiethylacetic acid, α-aminodiisopropylacetic acid, α-aminodi-n-propylacetic acid, α-aminodiisobutylacetic acid, α-aminodi-n-butylacetic acid, α-aminoethylisopropylacetic acid, α-amino-n-propylacetic acid, α-aminodiisoamyacetic acid, α-methylaspartic acid, α-methylglutamic acid, 1-aminocyclopropane-1-carboxylic acid; isoleucine, alloisoleucine, tert-leucine, β-methyltryptophan and α-amino-β-ethyl-β-phenylpropionic acid residues; β-phenylserinyl;

Aliphatic α-amino-β-hydroxy acids such as serine, β-hydroxyleucine, β-hydroxynorleucine, β-hydroxynorvaline, and α-amino-β-hydroxystearic acid residues;

α-Amino, α-, γ-, δ- ε-hydroxy acids such as homoserine, γ-hydroxynorvaline, δ-hydroxynorvaline and epsilonhydroxynorleucine residues; canavinyl and canalinyl; γ-hydroxyornithinyl;

2-hexosaminic acids such as D-glucosaminic acid or D-galactosaminic acid residues;

α-Amino-β-thiols such as penicillamine, β-thiolnorvaline or β-thiolbutyrine residues;

Other sulfur containing amino acid residues including cysteine; homocystine; β-phenylmethionine; methionine; S-allyl-L-cysteine sulfoxide; 2-thiolhistidine; cystathionine; and thiol ethers of cysteine or homocysteine;

Phenylalanine, tryptophan and ring-substituted α amino acids such as the phenyl- or cyclohexylamino acids α-aminophenylacetic acid, α-aminocyclohexylacetic acid and α-amino-β-cyclohexylpropionic acid; phenylalanine analogues and derivatives comprising aryl, lower alkyl, hydroxy, guanidino, oxyalkylether, nitro, sulfur or halosubstituted phenyl (e.g., tyrosine, methyltyrosine and o-chloro-, p-chloro-, 3,4-dicloro, o-, m- or p-methyl-, 2,4, 6-trimethyl-, 2-ethoxy-5-nitro, 2-hydroxy-5-nitro and p-nitro-phenylalanine); furyl-, thienyl-, pyridyl-, pyrimidinyl-, purine or naphthylalanines; and tryptophan analogues and derivatives including kynurenine, 3-hydroxykynurenine, 2-hydroxytryptophan and 4-carboxytryptophan residues;

α-Amino substituted amino acid residues including sarcosine (N-methylglycine), N-benzylglycine, N-methylalanine, N-benzylalanine, N-methylphenylalanine, N-benzylphenylalanine, N-methylvaline and N-benzylvaline; and α-Hydroxy and substituted α-hydroxy amino acid residues including serine, threonine, allothreonine, phosphoserine and phosphothreonine residues.

Any one of the foregoing or other known amino acids are suitably employed in this invention particularly if they are capable of autocatalytically hydrolyzing a P-amidate bond. Thus, in this case they should contain a free carboxyl group, or should do so upon hydrolysis in vivo.

Of particular interest are hydrophobic residues such as mono-or di-alkyl or aryl amino acids, cycloalkylamino acids and the like. These residues contribute to cell permeability by increasing the partition coefficient of the nucleotide analogue amidate. Typically, the residue does not contain a sulfhydryl or guanidino substituent.

Y optionally is a polypeptide radical. Polypeptides comprise dipeptides (2 residues), or polypeptides of 3, 5, 10 and up to 100 or more residues. They include enzymes (e.g., hydrogen peroxidase) as well as antibodies or proteins of any type against which one wishes to raise an immune response. The nature and identity of the polypeptide may vary widely. The polypeptide optionally contains a peptidolytic enzyme cleavage site at the peptide bond between the first and second residues adjacent to the phosphorus atom. Such cleavage sites are flanked by enzymatic recognition structures, e.g. a particular sequence of residues recognized by a peptidolytic enzyme.

Peptidolytic enzymes for cleaving the polypeptide conjugates of this invention are well known, and in particular include carboxypeptidases. Carboxypeptidases digest polypeptides by removing C-terminal residues, and are specific in many instances for particular C-terminal sequences. Such enzymes and their substrate requirements in general are well known. For example, a dipeptide (having a given pair of residues and a free carboxyl terminus) is covalently bonded through its α-amino group to the phosphorus or carbon atoms of the compounds herein. It is expected that this peptide will be cleaved by the appropriate peptidolytic enzyme, leaving the carboxyl of the proximal amino acid residue to autocatalytically cleave a phosphonoamidate bond.

Suitable dipeptidyl groups (designated by their single letter code) are AA, AR, AN, AD, AC, AE, AQ, AG, AH, AI, AL, AK, AM, AF, AP, AS, AT, AW, AY, AV, RA, RR, RN, RD, RC, RE, RQ, RG, RH, RI, RL, RK, RM, RF, RP, RS, RT, RW, RY, RV, NA, NR, NN, ND, NC, NE, NQ, NG, NH, NI, NL, NK, NM, NF, NP, NS, NT, NW, NY, NV, DA, DR, DN, DD, DC, DE, DQ, DG, DH, DI, DL, DK, DM, DF, DP, DS, DT, DW, DY, DV, CA, CR, CN, CD, CC, CE, CQ, CG, CH, CI, CL, CK, CM, CF, CP, CS, CT, CW, CY, CV, EA, ER, EN, ED, EC, EE, EQ, EG, EH, El, EL, EK, EM, EF, EP, ES, ET, EW, EY, EV, QA, QR, QN, QD, QC, QE, QQ, QG, QH, QI, QL, QK, QM, QF, QP, QS, QT, QW, QY, QV, GA, GR, GN, GD, GC, GE, GQ, GG, GH, GI, GL, GK, GM, GF, GP, GS, GT, GW, GY, GV, HA, HR, HN, HD, HC, HE, HQ, HG, HH, HI, HL, HK, HM, HF, HP, HS, HT, HW, HY, HV, IA, IR, IN, ID, IC, IE, IQ, IG, IH, II, IL, IK, IM, IF, IP, IS, IT, IW, IY, IV, LA, LR, LN, LD, LC, LE, LQ, LG, LH, LI, LL, LK, LM, LF, LP, LS, LT, LW, LY, LV, KA, KR, KN, KD, KC, KE, KQ, KG, KH, KI, KL, KK, KM, KF, KP, KS, KT, KW, KY, KV, MA, MR, MN, MD, MC, ME, MQ, MG, MH, MI, ML, MK, MM, MF, MP, MS, MT, MW, MY, MV, FA, FR, FN, FD, FC, FE, FQ, FG, FH, FL, FL, FK, FM, FF, FP, FS, FT, FW, FY, FV, PA, PR, PN, PD, PC, PE, PQ, PG, PH, PI, PL, PK, PM, PF, PP, PS, PT, PW, PY, PV, SA, SR, SN, SD, SC, SE, SQ, SG, SH, SI, SL, SK, SM, SF, SP, SS, ST, SW, SY, SV, TA, TR, TN, TD, TC, TE, TQ, TG, TH, TI, TL, TK, TM, TF, TP, TS, TT, TW, TY, TV, WA, WR, WN, WD, WC, WE, WQ, WG, WH, WI, WL, WK, WM, WF, WP, WS, WT, WW, WY, WV, YA, YR, YN, YD, YC, YE, YQ, YG, YH, YI, YL, YK, YM, YF, YP, YS, YT, YW, YY, YV, VA, VR, VN, VD, VC, VE, VQ, VG, VH, VI, VL, VK, VM, VF, VP, VS, VT, VW, VY and VV.

Tripeptides are also useful as Y. The sequence -X4-pro-X5-(where X4 is any amino acid residue and X5 is an amino acid residue, a carboxyl ester of proline, or hydrogen) will be cleaved by luminal carboxypeptidase to yield X4 with a free carboxyl, which in turn autocatalytically cleaves the phosphono amidate bond or the monoamino acid amidate is hydrolyzed itself by peptidases capable of yielding the free carboxyl. X5 usually will be a benzyl ester of the carboxy group of X5.

Dipeptide or tripeptide species can be selected on the basis of known transport properties and/or susceptibility to peptidases that can affect transport to intestinal mucosal or other cell types. Dipeptides and tripeptides lacking an α-amino group are transport substrates for the peptide transporter found in brush border membrane of intestinal mucosal cells (Bai, J. P. F., "Pharm Res." 9:969–978 (1992). Transport competent peptides can thus be used to enhance bioavailability of Y amidate compounds. Di- or tripeptides having one or more amino acids in the D configuration are also compatible with peptide transport and can be utilized in Y amidate compounds. Amino acids in the D configuration can be used to reduce the susceptibility of a di- or tripeptide to hydrolysis by proteases common to the brush border such as aminopeptidase N (EC 3.4.11.2). In addition, di- or tripeptides with amino acid residues can be selected on the basis of their relative resistance to hydrolysis by proteases found in the lumen of the intestine. For example, tripeptides or oligopeptides lacking asp and/or glu are poor substrates for aminopeptidase A (EC 3.4.11.7), di- or tripeptides lacking amino acid residues on the N-terminal side of hydrophobic amino acids (leu, tyr, phe, val, trp) are poor substrates for endopeptidase 24.11 (EC 3.4.24.11), and peptides lacking a pro residue at the penultimate position at a free carboxyl terminus are poor substrates for carboxypeptidase P (EC 3.4.17). Similar considerations can also be applied to the selection of peptides that are either relatively resistant or relatively susceptible to hydrolysis by cytosolic, renal, hepatic, serum or other peptidases. Such poorly cleaved polypeptide amidates are immunogens or are useful for bonding to proteins in order to prepare immunogens.

Table B lists $R_{6a}$ ester and amidate moieties that can be bonded via oxygen or directly, respectively, to —C(O)O— and —P(P)(O—)$_2$ groups. Esters of structures 1–5, 8–10 and 16, 17, 19–22 are synthesized by reacting the compound herein having a free hydroxyl with the corresponding halide (chloride or acyl chloride and the like) and N,N-dicylohexyl-N-morpholine carboxamidine (or another base such as DBU, triethylamine, CsCO$_3$, N,N-dimethylaniline and the like) in DMF (or other solvent such as acetonitrile or N-methylpyrrolidone). When $E_1$ is phosphonate, the esters of structures 5–7, 11, 12, 21, and 23–26 are synthesized by reaction of the alcohol or alkoxide salt (or the corresponding amines in the case of compounds such as 13, 14 and 15) with the monochlorophosphonate or dichlorophosphonate (or another activated phosphonate).

TABLE B

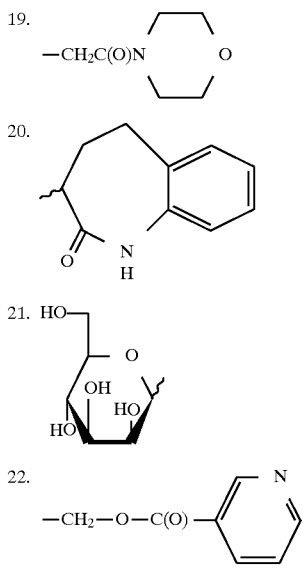

TABLE B-continued

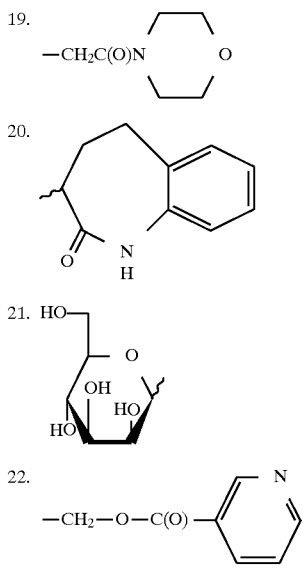

*Each $R^8$ is the same or different C1–C6 alkyl (includes methyl, ethyl, propyl, isopropyl and t-butyl).
chiral center is (R), (S) or racemate.

Other esters that are suitable for use herein are described in EP 632,048.

Exemplary $R_{6a}$ carboxylic acid, phosphonic acid, phosphonate, sulfonic acid and other protecting groups for $W_1$ acids are described in detail in Greene, T. W., "Protective Groups in Organic Synthesis" (John Wiley & sons, New York, 1981) as set forth below. Such groups include by way of example and not limitation, esters, amides, hydrazides, and the like.

In some embodiments the $R_{6a}$ protected acidic group is an ester or amide of the acidic group and $R_{6a}$ is the residue of hydroxyl or amino-containing functionality. The residues of suitable hydroxyl or amino-containing functionalities are set forth above or are found in WO 95/07920. Of particular interest are the residues of amino acids, amino acid esters, polypeptides, or aryl alcohols. Typical amino acid, polypeptide and carboxyl-esterified amino acid residues are described on pages 11–18 and related text of WO 95/07920 as groups L1 or L2, which is hereby incorporated by reference. WO 95/07920 expressly teaches the amidates of phosphonic acids, but it will be understood that such amidates are formed with any of the acid groups set forth herein and the amino acid residues set forth in WO 95/07920. The polypeptide amidates are useful as immunogens in raising antibodies against either the polypeptide (if it is not immunogenic in the animal to which it is administered) or against the epitopes on the remainder of the compound of this invention.

Typical $R_{6a}$ esters for protecting $W_1$ acidic functionalities are also described in WO 95/07920, again understanding that the same esters can be formed with the acidic groups herein as with the phosphonate of the '920 publication. Typical ester groups are defined at least on WO 95/07920 pages 89–93 (under $R^{31}$ or $R^{35}$), the table on page 105, and pages 21–23 (as R). Of particular interest are esters of unsubstituted aryl such as phenyl or arylalkyl such benzyl, or hydroxy-, halo-, alkoxy-, carboxy- and/or alkylestercarboxy-substituted aryl or alkylaryl, especially phenyl, ortho-ethoxyphenyl, or C1–C4 alkylestercarboxyphenyl (salicylate C1–C4 alkylesters).

The protected acidic groups $W_1$, particularly when using the esters or amides of WO 95/07920, are useful as prodrugs for oral administration. However, it is not essential that the acidic group be protected in order for the compounds of this invention to be effectively administered by the oral route. When the compounds of the invention having protected groups, in particular amino acid amidates or substituted and unsubstituted aryl esters are administered systemically or orally they are capable of hydrolytic cleavage in vivo to yield the free acid.

One or more of the acidic hydroxyls are protected. If more than one acidic hydroxyl is protected then the same or a different protecting group is employed, e.g., the esters may be different or the same, or a mixed amidate ester may be used.

Protecting groups embraced within $W_1$ also include alkyl- or aryl-acyloxyalkyl groups of the structure —$CH_2O(CO)R_{37}$ or —$CH_2(CO)OR_{38}$ (linked to oxygen of the acidic group) wherein $R_{37}$ and $R_{38}$ are alkyl, aryl, or alkylaryl groups (see U.S. Pat. No. 4,968,788). Frequently $R_{37}$ and $R_{38}$ are bulky groups such as branched alkyl, ortho-substituted aryl, meta-substituted aryl, or combinations thereof, including normal, secondary, iso- and tertiary alkyls of 1–6 carbon atoms. An example is the pivaloyloxymethyl group. These are of particular use with prodrugs for oral administration.

$R_{6b}$ are residues of carboxylic acids for the most part, but any of the typical amino protecting groups described by Greene at pages 315–385 are useful. They include Carbamates (methyl and ethyl, 9-fluorenylmethyl, 9(2-sulfo) fluoroenylmethyl, 9-(2,7-dibromo)fluorenylmethyl, 2,7-di-t-buthyl-[9-(10,10-dioxo-10,10,10,10-tetrahydrothioxanthyl)] methy, 4-methoxyphenacyl); Substituted Ethyl (2,2,2-trichoroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chorobenzyl, 2,4-dichlorobenzyl, 4-methylsulfinylbenzyl, 9-anthrylmethyl, diphenylmethyl); Groups With Assisted Cleavage (2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-choro-p-acyloxybenzyl, p-(dihydroxyboryl) benzyl, 5-benzisoxazolylmethyl, 2-(trifluoromethyl)-6-chromonylmethyl); Groups Capable of Photolytic Cleavage (m-nitrophenyl, 3,5-dimethoxybenzyl, o-nitrobenzyl, 3,4-dimethoxy-6-nitrobenzyl, phenyl(o-nitrophenyl)methyl); Urea-Type Derivatives (phenothiazinyl-(10)-carbonyl, N'-p-toluenesulfonylaminocarbonyl, N'-phenylaminothiocarbonyl); Miscellaneous Carbamates (t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido) benzyl, 1,1-dimethyl-3-(N,N-dimethylcarboxamido)propyl, 1,1-dimethylpropynyl, di(2-pyridyl)methyl, 2-furanylmethyl, 2-Iodoethyl, Isobornyl, Isobutyl, Isonicotinyl, p-(p'-Methoxyphenylazo)benzyl, 1-methylcyclobutyl, 1-methylcyclohexyl, 1-methyl-1-cyclopropylmethyl, 1-methyl-1-(3,5-dimethoxyphenyl) ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, 2,4,6-trimethylbenzyl); Amides (N-formyl, N-acetyl, N-choroacetyl, N-trichoroacetyl, N-trifluoroacetyl, N-phenylacetyl, N-3-phenylpropionyl, N-picolinoyl, N-3-pyridylcarboxamide, N-benzoylphenylalanyl, N-benzoyl, N-p-phenylbenzoyl); Amides With Assisted Cleavage (N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3(o-nitrophenyl)propionyl, N-2-methyl-2-(o-nitrophenoxy)propionyl, N-2methyl-2-(o-phenylazophenoxy)propionyl, N-4-chlorobutyryl, N-3-methyl-3nitrobutyryl, N-o-nitrocinnamoyl, N-acetylmethionine, N-o-nitrobenzoyl, N-o-(benzoyloxymethyl)benzoyl, 4,5-diphenyl-3-oxazolin-2-one); Cyclic Imide Derivatives (N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridonyl); N-Alkyl and N-Aryl Amines (N-methyl, N-allyl, N-[2-(trimethylsilyl)ethoxy]methyl, N-3-acetoxypropyl, N-(1-isopropyl-4-nitro-2-oxo-3-pyrrolin-3-yl), Quaternary Ammonium Salts, N-benzyl, N-di(4-methoxyphenyl)methyl, N-5-dibenzosuberyl, N-triphenylmethyl, N-(4-methoxyphenyl)diphenylmethyl, N-9-phenylfluorenyl, N-2,7-dichloro-9-fluorenylmethylene, N-ferrocenylmethyl, N-2-picolylamine N'-oxide), Imine Derivatives (N-1,1-dimethylthiomethylene, N-benzylidene, N-p-methoxybenylidene, N-diphenylmethylene, N-[(2-pyridyl)mesityl]methylene, N,(N',N'-dimethylaminomethylene, N,N'-isopropylidene, N-p-nitrobenzylidene, N-salicylidene, N-5-chlorosalicylidene, N-(5-chloro-2-hydroxyphenyl)phenylmethylene, N-cyclohexylidene); Examine Derivatives (N-(5,5-dimethyl-3-oxo-1-cyclohexenyl)); N-Metal Derivatives (N-borane derivatives, N-diphenylborinic acid derivatives, N-[phenyl(pentacarbonylchromium- or -tungsten)]carbenyl, N-copper or N-zinc chelate); N-N Derivatives (N-nitro, N-nitroso, N-oxide); N-P Derivatives (N-diphenylphosphinyl, N-dimethylthiophosphinyl, N-diphenylthiophosphinyl, N-dialkyl phosphoryl, N-dibenzyl phosphoryl, N-diphenyl phosphoryl); N-Si Derivatives; N-S Derivatives; N-Sulfenyl Derivatives (N-benzenesulfenyl, N-o-nitrobenzenesulfenyl, N-2,4-dinitrobenzenesulfenyl, N-pentachlorobenzenesulfenyl, N-2-nitro-4-methoxybenzenesulfenyl, N-triphenylmethylsulfenyl, N-3-nitropyridinesulfenyl); and N-sulfonyl Derivatives (N-p-toluenesulfonyl, N-benzenesulfonyl, N-2,3,6-trimethyl-4-methoxybenzenesulfonyl, N-2,4,6-trimethoxybenzenesulfonyl, N-2,6-dimethyl-4-methoxybenzenesulfonyl, N-pentamethylbenzenesulfonyl, N-2,3,5,6,-tetramethyl-4-methoxybenzenesulfonyl, N-4-methoxybenzenesulfonyl, N-2,4,6-trimethylbenzenesulfonyl, N-2,6-dimethoxy-4-methylbenzenesulfonyl, N2,2,5,7,8-pentamethylchroman-6-sulfonyl, N-methanesulfonyl, N-β-trimethylsilyethanesulfonyl, N-9-anthracenesulfonyl, N-4-(4', 8'-dimethoxynaphthylmethyl)benzenesulfonyl, N-benzylsulfonyl, N-trifluoromethylsulfonyl, N-phenacylsulfonyl).

More typically, protected amino groups include carbamates and amides, still more typically, —$NHC(O)R_1$ or —$N=CR_1N(R_1)_2$.

Stereoisomers

The compounds of the invention are enriched or resolved optical isomers at any or all asymmetric atoms. For example, the chiral centers apparent from the depictions are provided as the chiral isomers or racemic mixtures. Both racemic and diasteromeric mixtures, as well as the individual optical isomers isolated or synthesized, substantially free of their enantiomeric or diastereomeric partners, are all within the scope of the invention. The racemic mixtures are separated into their individual, substantially optically pure isomers through well-known techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Exemplary stereochemistry of the compounds of this invention is set forth below in Table C.

TABLE C (I)  (II)

Formula (I)

| $E_1$ | $J_{1a}$ | $J_{1b}$ | $U_1$ | $T_1$ | $G_1$ |
|---|---|---|---|---|---|
| — | — | α | β | α | α |
| — | — | β | α | α | α |
| — | — | α | β | β | α |
| — | — | α | β | α | β |
| — | — | β | α | β | α |
| — | — | β | α | α | β |
| — | — | α | β | β | β |
| — | — | β | α | β | β |

| $E_1$ | $J_{1a}$ | $J_{1b}$ | $J_2$ | $U_1$ | $T_1$ | $G_1$ |
|---|---|---|---|---|---|---|
| — | α | β | α | β | α | α |
| — | β | α | α | β | α | α |
| — | α | β | β | α | α | α |
| — | α | β | α | β | β | α |
| — | α | β | α | β | α | β |
| — | β | α | β | α | α | α |
| — | β | α | α | β | β | α |
| — | β | α | α | β | α | β |
| — | α | β | β | α | β | α |
| — | α | β | β | α | α | β |
| — | α | β | α | β | β | β |
| — | β | α | β | α | β | α |
| — | β | α | β | α | α | β |
| — | β | α | α | β | β | β |
| — | α | β | β | α | β | β |
| — | β | α | β | α | β | β |

The compounds of the invention can also exist as tautomeric isomers in certain cases. For example, ene-amine tautomers can exist for imidazole, guanidine, amidine, and tetrazole systems and all their possible tautomeric forms are within the scope of the invention.

Salts

The compositions of this invention optionally comprise pharmaceutically acceptable non-toxic salts of the compounds herein, containing, for example, $Na^+$, $Li^+$, $K^+$, $Ca^{++}$ and $Mg^{++}$. Such salts may include those derived by combination of appropriate cations such as alkali and alkaline earth metal ions or ammonium and quaternary amino ions with an acid anion moiety, typically the $W_1$ group carboxylic acid.

Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound.

In addition, salts may be formed from acid addition of certain organic and inorganic acids, e.g., HCl, HBr, $H_2SO_4$, amino acids (described above) or organic sulfonic acids, with basic centers, typically amines of group $G_1$, or with acidic groups such as $E_1$. Finally, it is to be understood that the compositions herein comprise compounds of the invention in their un-ionized, as well as zwitterionic form.

Exemplary Enumerated Compounds.

By way of example and not limitation, embodiment compounds are named below in tabular format (Table 6). Generally, each compound is depicted as a substituted nucleus in which the nucleus is designated by capital letter and each substituent is designated in order by lower case letter or number. Tables 1a and 1b are a schedule of nuclei which differ principally by the position of ring unsaturation and the nature of ring substituents. Each nucleus is given a alphabetical designation from Tables 1a and 1b, and this designation appears first in each compound name. Similarly, Tables 2a–h, 3a–b, 4a–c, and 5a–d list the selected $Q_1$, $Q_2$, $Q_3$ and $Q_4$ substituents, again by letter or number designation. Accordingly, each named compound will be depicted by a capital letter designating the nucleus from Table 1a–1b, followed by a number designating the $Q_1$ substituent, a lower case letter designating the $Q_2$ substituent, a number designating the $Q_3$ substituent, and a lower case letter or letters designating the $Q_4$ substituent. Thus, structure 8, scheme 1, is represented by A.49.a.4.i. $Q_1$–$Q_4$, it should be understood, do not represent groups or atoms but are simply connectivity designations.

TABLE 1a

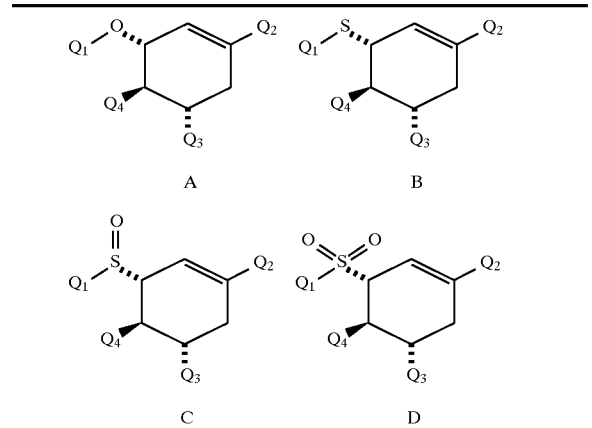

A  B

C  D

TABLE 1a-continued
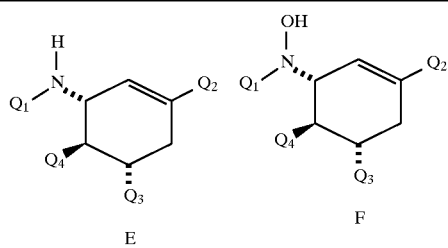
E    F
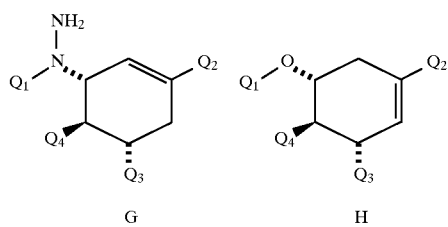
G    H
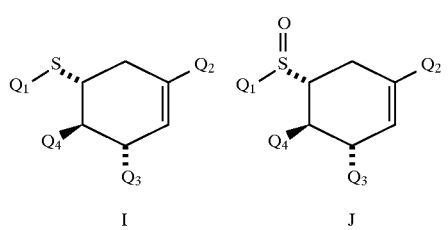
I    J
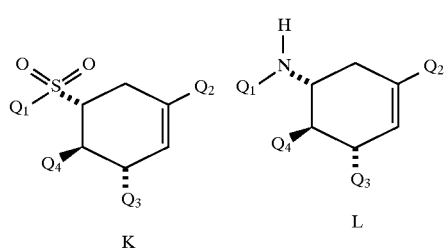
K    L
TABLE 1b
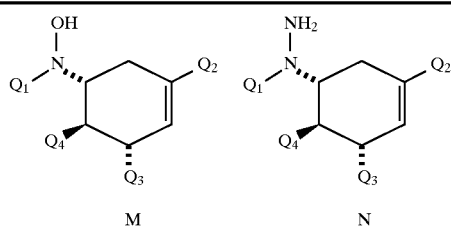
M    N
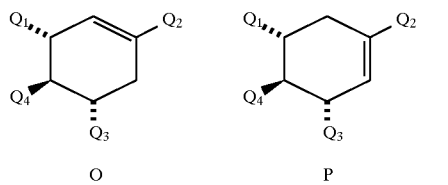
O    P
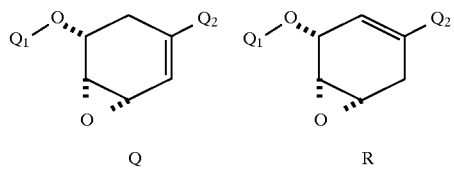
Q    R
TABLE 1b-continued
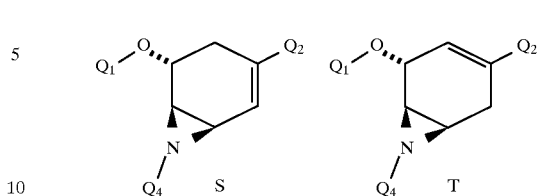
S    T
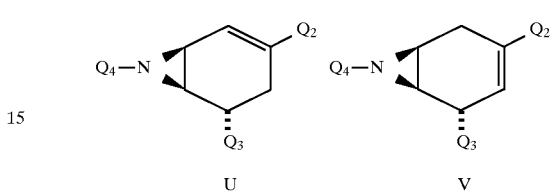
U    V
TABLE 2a
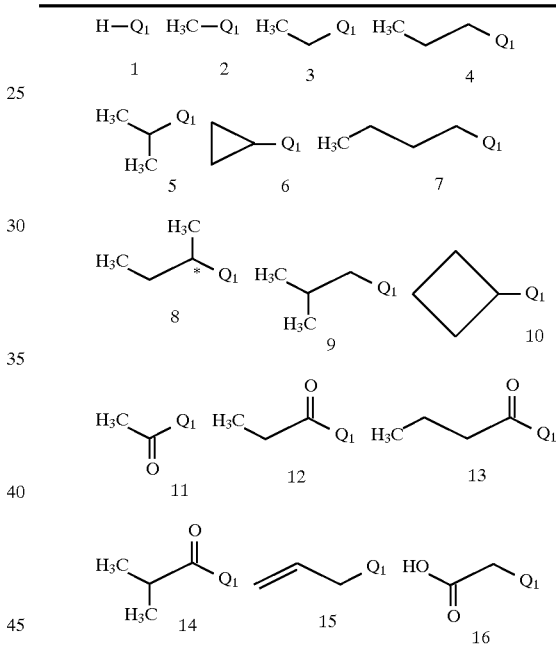
TABLE 2b
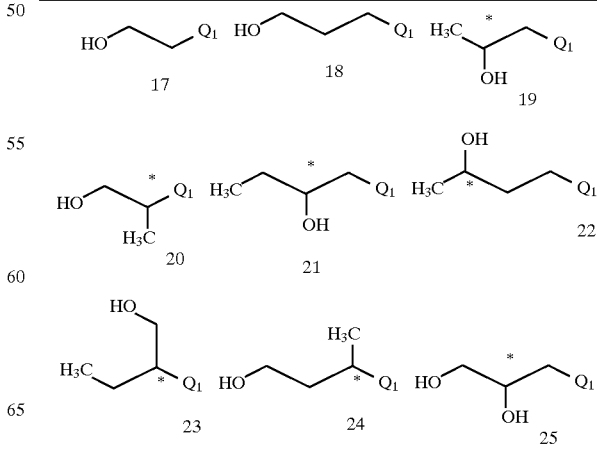

TABLE 2b-continued
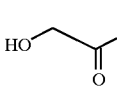
TABLE 2c
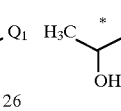
TABLE 2d
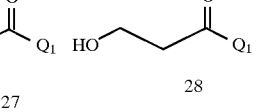
TABLE 2e
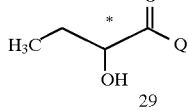

TABLE 2e-continued
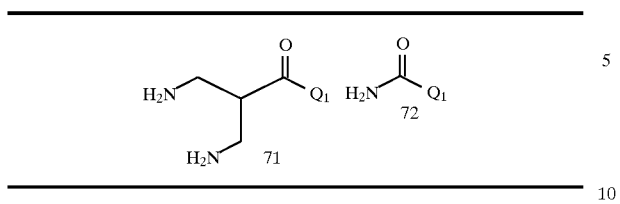
TABLE 2f
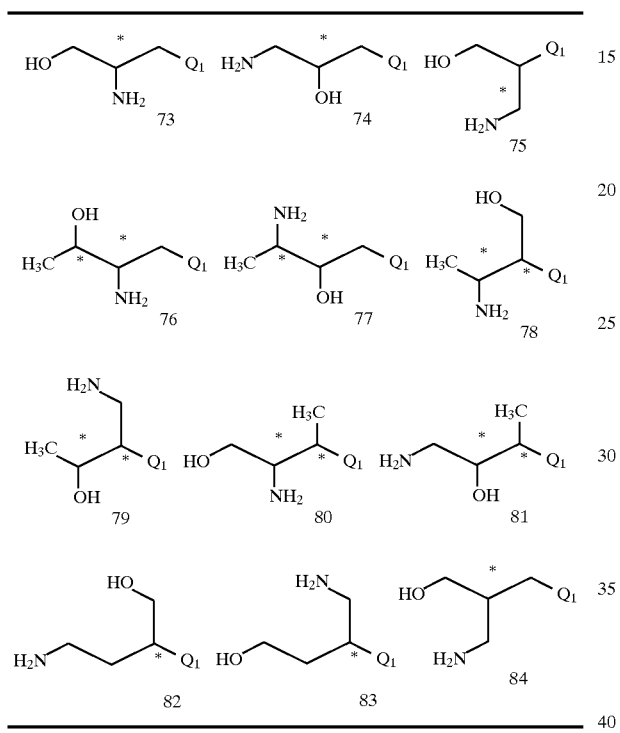
TABLE 2g
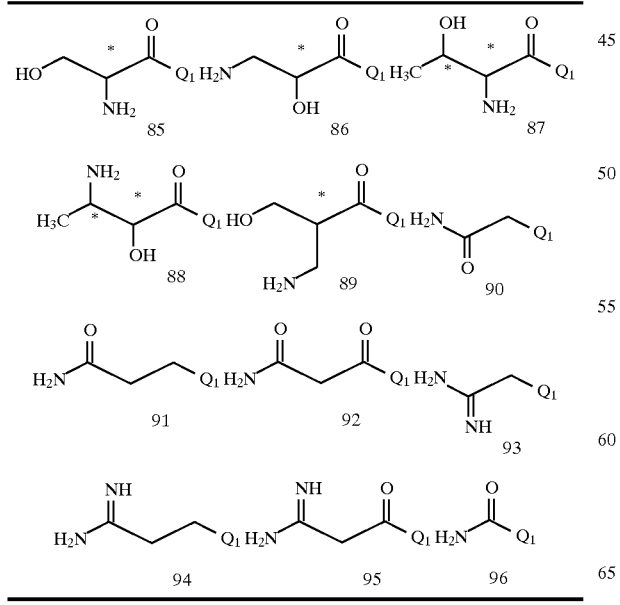
TABLE 2h
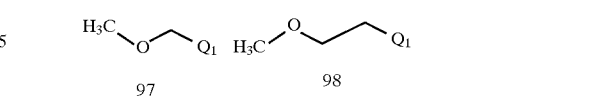
TABLE 3a
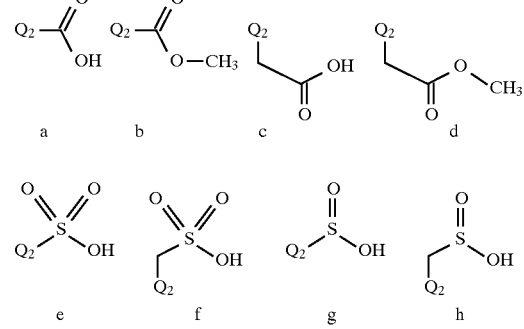
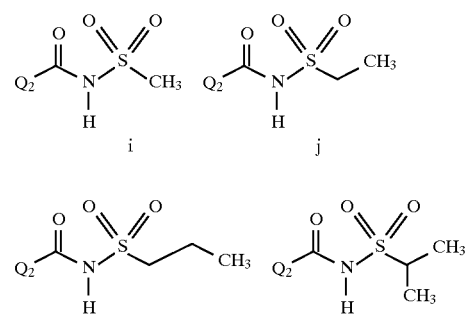
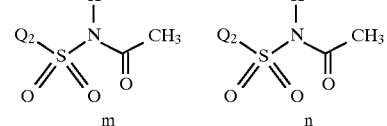
TABLE 3b
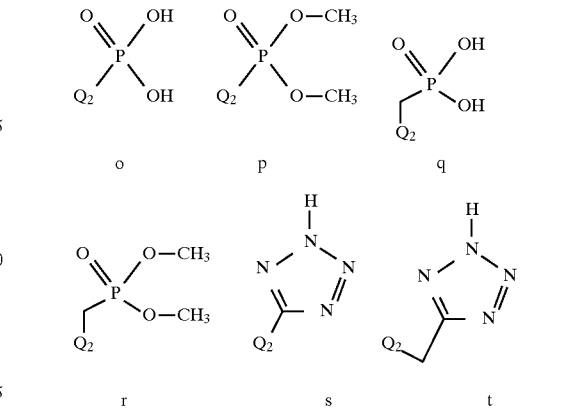

TABLE 3b-continued
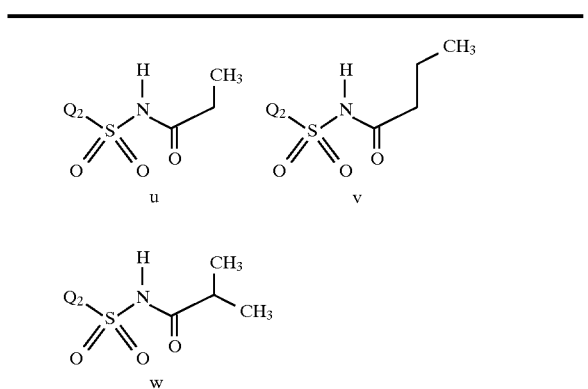
TABLE 4a
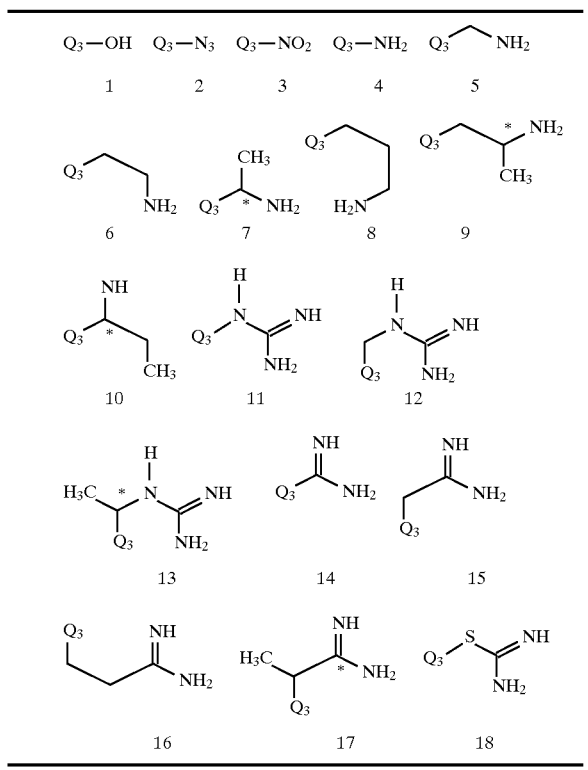
TABLE 4b
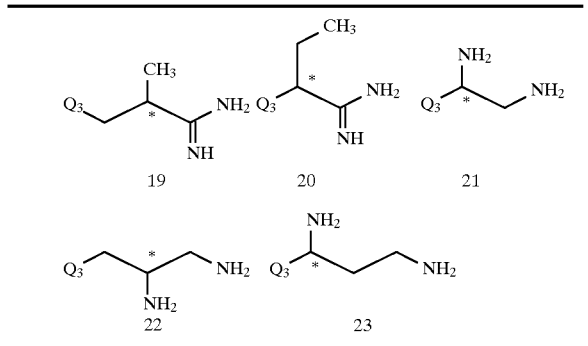
TABLE 4b-continued
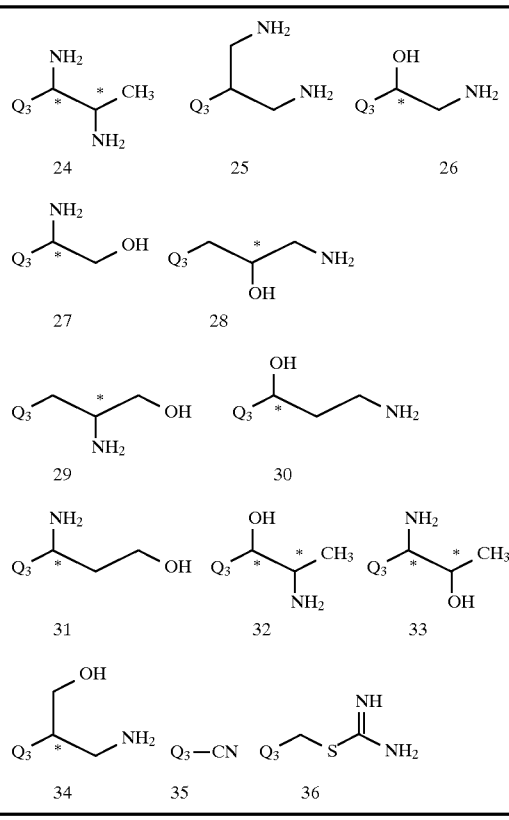
TABLE 4c
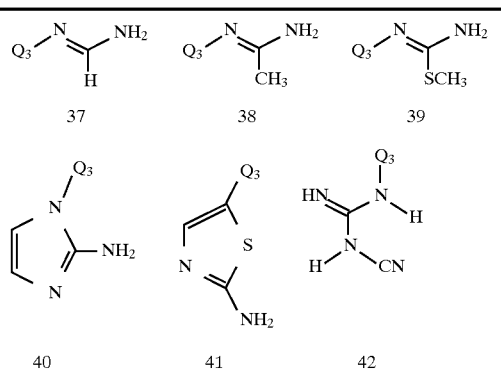
TABLE 5a
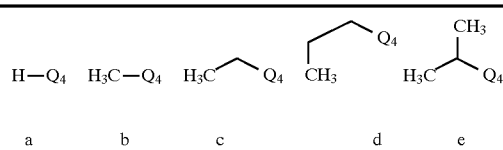

TABLE 5a-continued
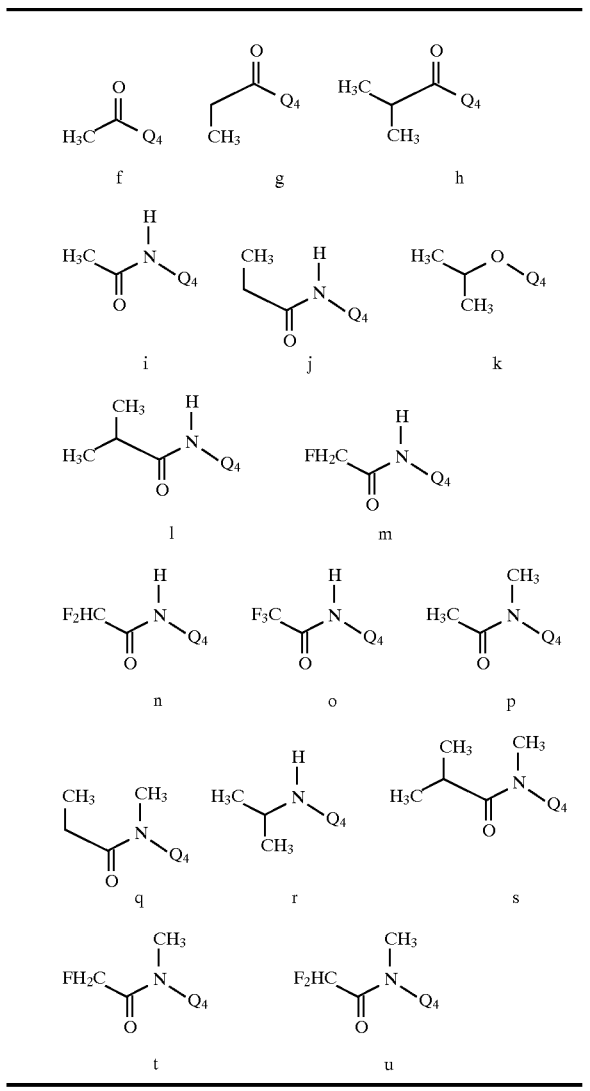
TABLE 5b
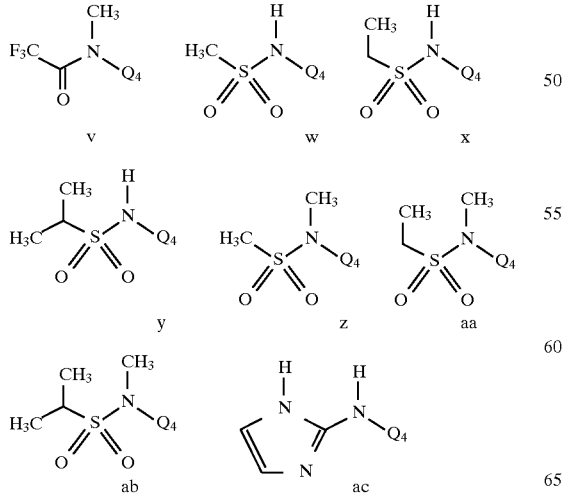
TABLE 5b-continued
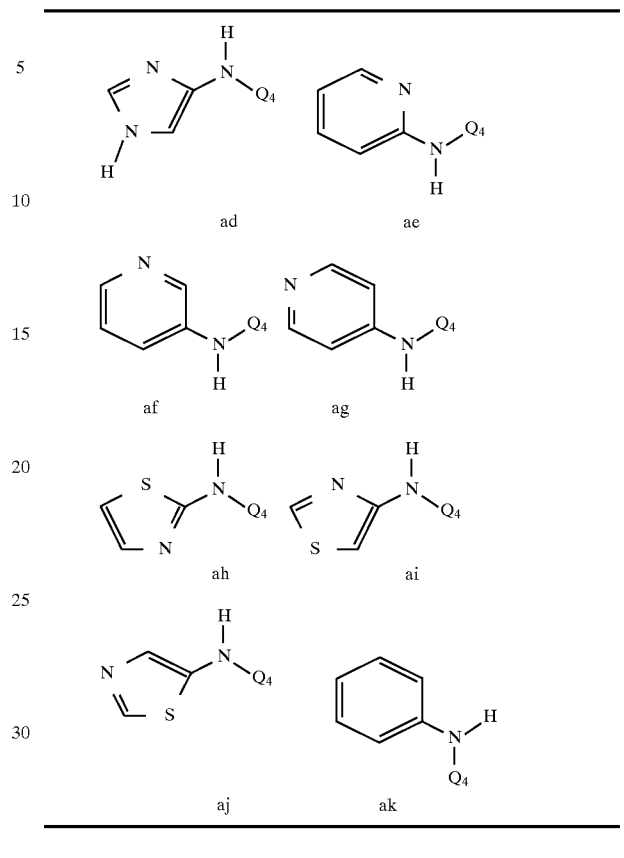
TABLE 5c
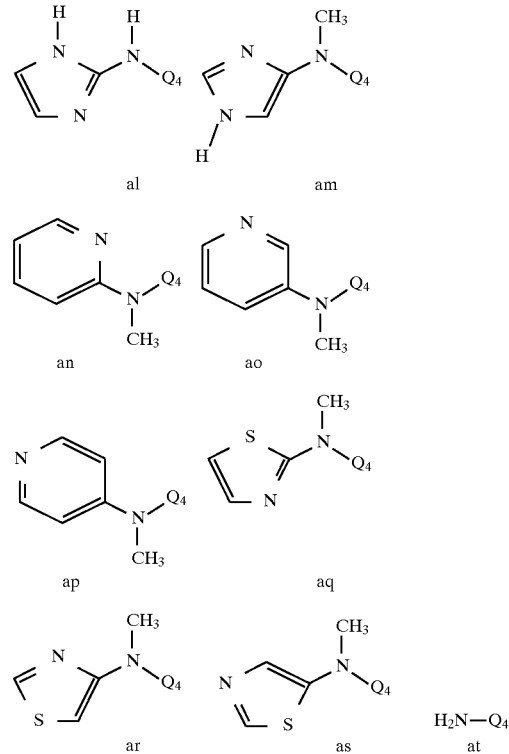

TABLE 5c-continued

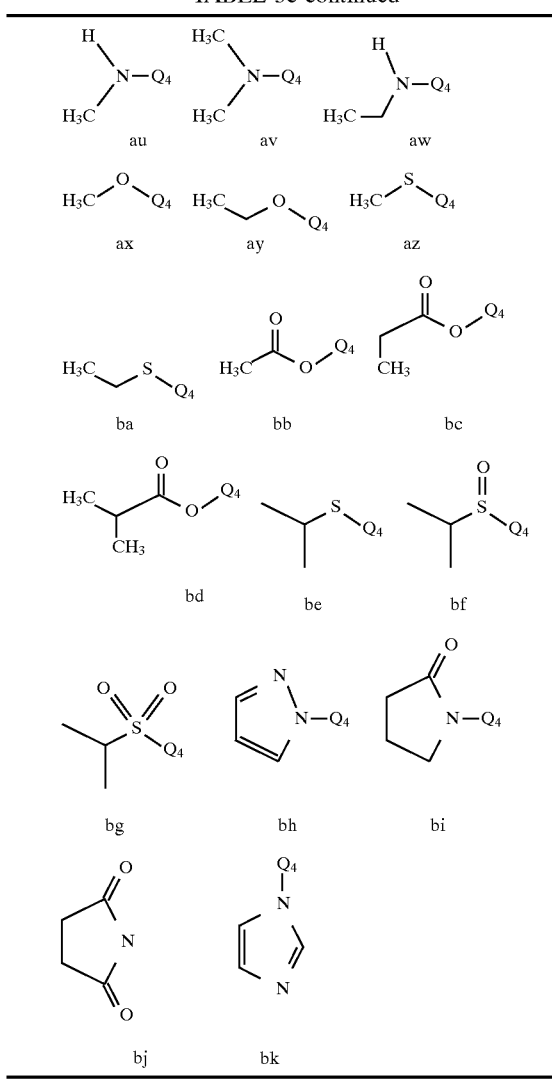

Table 6—Exemplary Enumerated Compounds

A.17.a.4.i; A.17.a.4.v; A.17.a.6.i; A.17.a.6.v; A.17.a.11.i; A.17.a.11.v; A.17.a.14.i;
A.17.a.14.v; A.17.a.15.i; A.17.a.15.v; A.17.a.18.i; A.17.a.18.v; A.17.a.25.i;
A.17.a.25.v; A.17.e.4.i; A.17.e.4.v; A.17.e.6.i; A.17.e.6.v; A.17.e.11.i; A.17.e.11.v;
A.17.e.14.i; A.17.e.14.v; A.17.e.15.i; A.17.e.15.v; A.17.e.18.i; A.17.e.18.v;
A.17.e.25.i; A.17.e.25.v; A.17.g.4.i; A.17.g.4.v; A.17.g.6.i; A.17.g.6.v; A.17.g.11.i;
A.17.g.11.v; A.17.g.14.i; A.17.g.14.v; A.17.g.15.i; A.17.g.15.v; A.17.g.18.i;
A.17.g.18.v; A.17.g.25.i; A.17.g.25.v; A.17.l.4.i; A.17.l.4.v; A.17.l.6.i; A.17.l.6.v;
A.17.l.11.i; A.17.l.11.v; A.17.l.14.i; A.17.l.14.v; A.17.l.15.i; A.17.l.15.v; A.17.l.18.i;
A.17.l.18.v; A.17.l.25.i; A.17.l.25.v; A.17.m.4.i; A.17.m.4.v; A.17.m.6.i;
A.17.m.6.v; A.17.m.11.i; A.17.m.11.v; A.17.m.14.i; A.17.m.14.v; A.17.m.15.i;
A.17.m.15.v; A.17.m.18.i; A.17.m.18.v; A.17.m.25.i; A.17.m.25.v; A.17.o.4.i;
A.17.o.4.v; A.17.o.6.i; A.17.o.6.v; A.17.o.11.i; A.17.o.11.v; A.17.o.14.i;
A.17.o.14.v; A.17.o.15.i; A.17.o.15.v; A.17.o.18.i; A.17.o.18.v; A.17.o.25.i;
A.17.o.25.v; A.33.a.4.i; A.33.a.4.v; A.33.a.6.i; A.33.a.6.v; A.33.a.11.i; A.33.a.11.v;
A.33.a.14.i; A.33.a.14.v; A.33.a.15.i; A.33.a.15.v; A.33.a.18.i; A.33.a.18.v;
A.33.a.25.i; A.33.a.25.v; A.33.e.4.i; A.33.e.4.v; A.33.e.6.i; A.33.e.6.v; A.33.e.11.i;
A.33.e.11.v; A.33.e.14.i; A.33.e.14.v; A.33.e.15.i; A.33.e.15.v; A.33.e.18.i;
A.33.e.18.v; A.33.e.25.i; A.33.e.25.v; A.33.g.4.i; A.33.g.4.v; A.33.g.6.i; A.33.g.6.v;
A.33.g.11.i; A.33.g.11.v; A.33.g.14.i; A.33.g.14.v; A.33.g.15.i; A.33.g.15.v;
A.33.g.18.i; A.33.g.18.v; A.33.g.25.i; A.33.g.25.v; A.33.l.4.i; A.33.l.4.v; A.33.l.6.i;
A.33.l.6.v; A.33.l.11.i; A.33.l.11.v; A.33.l.14.i; A.33.l.14.v; A.33.l.15.i; A.33.l.15.v;
A.33.l.18.i; A.33.l.18.v; A.33.l.25.i; A.33.l.25.v; A.33.m.4.i; A.33.m.4.v;
A.33.m.6.i; A.33.m.6.v; A.33.m.11.i; A.33.m.11.v; A.33.m.14.i; A.33.m.14.v;
A.33.m.15.i; A.33.m.15.v; A.33.m.18.i; A.33.m.18.v; A.33.m.25.i; A.33.m.25.v;
A.33.o.4.i; A.33.o.4.v; A.33.o.6.i; A.33.o.6.v; A.33.o.11.i; A.33.o.11.v; A.33.o.14.i;
A.33.o.14.v; A.33.o.15.i; A.33.o.15.v; A.33.o.18.i; A.33.o.18.v; A.33.o.25.i;
A.33.o.25.v; A.49.a.4.i; A.49.a.4.v; A.49.a.6.i; A.49.a.6.v; A.49.a.11.i; A.49.a.11.v;
A.49.a.14.i; A.49.a.14.v; A.49.a.15.i; A.49.a.15.v; A.49.a.18.i; A.49.a.18.v;
A.49.a.25.i; A.49.a.25.v; A.49.e.4.i; A.49.e.4.v; A.49.e.6.i; A.49.e.6.v; A.49.e.11.i;
A.49.e.11.v; A.49.e.14.i; A.49.e.14.v; A.49.e.15.i; A.49.e.15.v; A.49.e.18.i;
A.49.e.18.v; A.49.e.25.i; A.49.e.25.v; A.49.g.4.i; A.49.g.4.v; A.49.g.6.i; A.49.g.6.v;
A.49.g.11.i; A.49.g.11.v; A.49.g.14.i; A.49.g.14.v; A.49.g.15.i; A.49.g.15.v;
A.49.g.18.i; A.49.g.18.v; A.49.g.25.i; A.49.g.25.v; A.49.l.4.i; A.49.l.4.v; A.49.l.6.i;
A.49.l.6.v; A.49.l.11.i; A.49.l.11.v; A.49.l.14.i; A.49.l.14.v; A.49.l.15.i; A.49.l.15.v;
A.49.l.18.i; A.49.l.18.v; A.49.l.25.i; A.49.l.25.v; A.49.m.4.i; A.49.m.4.v;
A.49.m.6.i; A.49.m.6.v; A.49.m.11.i; A.49.m.11.v; A.49.m.14.i; A.49.m.14.v;
A.49.m.15.i; A.49.m.15.v; A.49.m.18.i; A.49.m.18.v; A.49.m.25.i; A.49.m.25.v;
A.49.o.4.i; A.49.o.4.v; A.49.o.6.i; A.49.o.6.v; A.49.o.11.i; A.49.o.11.v; A.49.o.14.i;
A.49.o.14.v; A.49.o.15.i; A.49.o.15.v; A.49.o.18.i; A.49.o.18.v; A.49.o.25.i;
A.49.o.25.v; B.17.a.4.i; B.17.a.4.v; B.17.a.6.i; B.17.a.6.v; B.17.a.11.i; B.17.a.11.v;
B.17.a.14.i; B.17.a.14.v; B.17.a.15.i; B.17.a.15.v; B.17.a.18.i; B.17.a.18.v; B.17.a.25.i;
B.17.a.25.v; B.17.e.4.i; B.17.e.4.v; B.17.e.6.i; B.17.e.6.v; B.17.e.11.i; B.17.e.11.v;
B.17.e.14.i; B.17.e.14.v; B.17.e.15.i; B.17.e.15.v; B.17.e.18.i; B.17.e.18.v; B.17.e.25.i;
B.17.e.25.v; B.17.g.4.i; B.17.g.4.v; B.17.g.6.i; B.17.g.6.v; B.17.g.11.i; B,17.g.11.v;
B.17.g.14.i; B.17.g.14.v; B.17.g.15.i; B.17.g.15.v; B.17.g.18.i; B.17.g.18.v; B.17.g25.i;

B.17.g.25.v; B.17.l.4.i; B.17.l.4.v; B.17.l.6.i; B.17.l.6.v; B.17.l.11.i; B.17.l.11.v;
B.17.l.14.i; B.17.l.14.v; B.17.l.15.i; B.17.l.15.v; B.17.l.18.i; B.17.l.18.v; B.17.l.25.i;
B.17.l.25.v; B.17.m.4.i; B.17.m.4.v; B.17.m.6.i; B.17.m.6.v; B.17.m.11.i;
B.17.m.11.v; B.17.m.14.i; B.17.m.14.v; B.17.m.15.i; B.17.m.15.v; B.17.m.18.i;
B.17.m.18.v; B.17.m.25.i; B.17.m.25.v; B.17.o.4.i; B.17.o.4.v; B.17.o.6.i; B.17.o.6.v;
B.17.o.11.i; B.17.o.11.v; B.17.o.14.i; B.17.o.14.v; B.17.o.15.i; B.17.o.15.v;
B.17.o.18.i; B.17.o.18.v; B.17.o.25.i; B.17.o.25.v; B.33.a.4.i; B.33.a.4.v; B.33.a.6.i;
B.33.a.6.v; B.33.a.11.i; B.33.a.11.v; B.33.a.14.i; B.33.a.14.v; B.33.a.15.i; B.33.a.15.v;
B.33.a.18.i; B.33.a.18.v; B.33.a.25.i; B.33.a.25.v; B.33.e.4.i; B.33.e.4.v; B.33.e.6.i;
B.33.e.6.v; B.33.e.11.i; B.33.e.11.v; B.33.e.14.i; B.33.e.14.v; B.33.e.15.i; B.33.e.15.v;
B.33.e.18.i; B.33.e.18.v; B.33.e.25.i; B.33.e.25.v; B.33.g.4.i; B.33.g.4.v; B.33.g.6.i;
B.33.g.6.v; B.33.g.11.i; B.33.g.11.v; B.33.g.14.i; B.33.g.14.v; B.33.g.15.i; B.33.g.15.v;
B.33.g.18.i; B.33.g.18.v; B.33.g.25.i; B.33.g.25.v; B.33.l.4.i; B.33.l.4.v; B.33.l.6.i;
B.33.l.6.v; B.33.l.11.i; B.33.l.11.v; B.33.l.14.i; B.33.l.14.v; B.33.l.15.i; B.33.l.15.v;
B.33.l.18.i; B.33.l.18.v; B.33.l.25.i; B.33.l.25.v; B.33.m.4.i; B.33.m.4.v; B.33.m.6.i;
B.33.m.6.v; B.33.m.11.i; B.33.m.11.v; B.33.m.14.i; B.33.m.14.v; B.33.m.15.i;
B.33.m.15.v; B.33.m.18.i; B.33.m.18.v; B.33.m.25.i; B.33.m.25.v; B.33.o.4.i;
B.33.o.4.v; B.33.o.6.i; B.33.o.6.v; B.33.o.11.i; B.33.o.11.v; B.33.o.14.i; B.33.o.14.v;
B.33.o.15.i; B.33.o.15.v; B.33.o.18.i; B.33.o.18.v; B.33.o.25.i; B.33.o.25.v; B.49.a.4.i;
B.49.a.4.v; B.49.a.6.i; B.49.a.6.v; B.49.a.11.i; B.49.a.11.v; B.49.a.14.i; B.49.a.14.v;
B.49.a.15.i; B.49.a.15.v; B.49.a.18.i; B.49.a.18.v; B.49.a.25.i; B.49.a.25.v; B.49.e.4.i;
B.49.e.4.v; B.49.e.6.i; B.49.e.6.v; B.49.e.11.i; B.49.e.11.v; B.49.e.14.i; B.49.e.14.v;
B.49.e.15.i; B.49.e.15.v; B.49.e.18.i; B.49.e.18.v; B.49.e.25.i; B.49.e.25.v; B.49.g.4.i;
B.49.g.4.v; B.49.g.6.i; B.49.g.6.v; B.49.g.11.i; B.49.g.11.v; B.49.g.14.i; B.49.g.v;
B.49.g.15.i; B.49.g.15.v; B.49.g.18.i; B.49.g.18.v; B.49.g.25.i; B.49.g.25.v; B.49.l.4.i;
B.49.l.4.v; B.49.l.6.i; B.49.l.6.v; B.49.l.11.i; B.49.l.11.v; B.49.l.14.i; B.49.l.14.v;
B.49.l.15.i; B.49.l.15.v; B.49.l.18.i; B.49.l.18.v; B.49.l.25.i; B.49.l.25.v; B.49.m.4.i;
B.49.m.4.v; B.49.m.6.i; B.49.m.6.v; B.49.m.11.i; B.49.m.11.v; B.49.m.14.i;
B.49.m.14.v; B.49.m.15.i; B.49.m.15.v; B.49.m.18.i; B.49.m.18.v; B.49.m.25.i;
B.49.m.25.v; B.49.o.4.i; B.49.o.4.v; B.49.o.6.i; B.49.o.6.v; B.49.o.11.i; B.49.o.11.v;
B.49.o.14.i; B.49.o.14.v; B.49.o.15.i; B.49.o.15.v; B.49.o.18.i; B.49.o.18.v;
B.49.o.25.i; B.49.o.25.v; E.17.a.4.i; E.17.a.4.v; E.17.a.6.i; E.17.a.6.v; E.17.a.11.i;
E.17.a.11.v; E.17.a.14.i; E.17.a.14.v; E.17.a.15.i; E.17.a.15.v; E.17.a.18.i; E17.a.18.v;
E.17.a.25.i; E.17.a.25.v; E.17.e.4.i; E.17.e.4.v; E.17.e.6.i; E.17.e.6.v; E.17.e.11.i;
E.17.e.11.v; E.17.e.14.i; E.17.e.14.v; E.17.e.15.i; E.17.e.15.v; E.17.e.18.i; E.17.a.18.v;
E.17.e.25.i; E.17.e.25.v; E.17.g.4.i; E.17.g.4.v; E.17.g.6.i; E.17.g.6.v; E.17.e.11.i;
E.17.g.11.v; E.17.g.14.i; E.17.g.14.v; E.17.g.15.i; E.17.g.15.v; E.17.g.18.i; E.17.e.18.v;
E.17.g.25.i; E.17.g.25.v; E.17.l.4.i; E.17.l.4.v; E.17.l.6.i; E.17.l.6.v; E.17.l.11.i;
E.17.l.11.v; E.17.l.14.i; E.17.l.14.v; E.17.l.15.i; E.17.l.15.v; E.17.l.18.i; E.17.l.18.v;
E.17.l.25.i; E.17.l.25.v; E.17.m.4.i; E.17.m.4.v; E.17.m.6.i; E.17.m.6.v; E.17.m.11.i;
E.17.m.11.v; E.17.m.14.i; E.17.m.14.v; E.17.m.15.i; E.17.m.15.v; E.17.m.18.i;
E.17.m.18.v; E.17.m.25.i; E.17.m.25.v; E.17.o.4.i; E.17.o.4.v; E.17.o.6.i; E.17.o.6.v;
E.17.o.11.i; E.17.o.11.v; E.17.o.14.i; E.17.o.14.v; E.17.o.15.i; E.17.o.15.v; E.17.o.18.i;
E.17.o.18.v; E.17.o.25.i; E.17.o.25.v; E.33.a.4.i; E.33.a.4.v; E.33.a.6.i; E.33.a.6.v;
E.33.a.11.i; E.33.a.11.v; E.33.a.14.i; E.33.a.14.v; E.33.a.15.i; E.33.a.15.v; E.33.a.18.i;
E.33.a.18.v; E.33.a.25.i; E.33.a.25.v; E.33.e.4.i; E.33.e.4.v; E.33.e.6.i; E.33.e.6.v;
E.33.e.11.i; E.33.e.11.v; E.33.e.14.i; E.33.e.14.v; E.33.e.15.i; E.33.e.15.v; E.33.e.18.i;
E.33.e.18.v; E.33.e.25.i; E.33.e.25.v; E.33.g.4.i; E.33.g.4.v; E.33.g.6.i; E.33.g.6.v;
E.33.g.11.i; E.33.g.11.v; E.33.g.14.i; E.33.g.14.v; E.33.g.15.i; E.33.g.15.v; E.33.g.18.i;
E.33.g.18.v; E.33.g.25.i; E.33.g.25.v; E.33.l.4.i; E.33.l.4.v; E.33.l.6.i; E.33.l.6.v;
E.33.l.11.i; E.33.l.11.v; E.33.l.14.i; E.33.l.14.v; E.33.l.15.i; E.33.l.15.v; E.33.l.18.i;
E.33.l.18.v; E.33.l.25.i; E.33.l.25.v; E.33.m.4.i; E.33.m.4.v; E.33.m.6.i; E.33.m.4.v;
E.33.m.11.i; E.33.m.11.v; E.33.m.14.i; E.33.m.14.v; E.33.m.15.i; E.33.m.15.v;
E.33.m.18.i; E.33.m.18.v; E.33.m.25.i; E.33.m.25.v; E.33.o.4.i; E.33.o.4.v; E.33.o.6i;
E.33.o.6.v; E.33.o.11.i; E.33.o.11.v; E.33.o.14.i; E.33.o.14.v; E.33.o.15.i; E.33.o.15.v;
E.33.o.18.i; E.33.o.18.v; E.33.o.25.i; E.33.o.25.v; E.49.a.4.i; E.49.a.4.v; E.49.a.6.i;
E.49.a.6.v; E.49.a.11.i; E.49.a.11.v; E.49.a.14.i; E.49.a.14.v; E.49.a.15.i; E.49.a.15.v;
E.49.a.18.i; E.49.a.18.v; E.49.a.25.i; E.49.a.25.v; E.49.e.4.i; E.49.e.4.v; E.49.e.6.i;
E.49.e.6.v; E.49.e.11.i; E.49.e.11.v; E.49.e.14.i; E.49.e.14.v; E.49.e.15.i; E.49.e.15.v;
E.49.e.18.i; E.49.e.18.v; E.49.e.25.i; E.49.e.25.v; E.49.g.4.i; E.49.g.4.v; E.49.g.6.i;
E.49.g.6.v; E.49.g.11.i; E.49.g.11.v; E.49.g.14.i; E.49.g.14.v; E.49.g.15.i; E.49.g.15.v;
E.49.g.18.i; E.49.g.18.v; E.49.g.25.i; E.49.g.25.v; E.49.l.4.i; E.49.l.4.v; E.49.l.6.i;
E.49.l.6.v; E.49.l.11.i; E.49.l.11.v; E.49.l.14.i; E.49.l.14.v; E.49.l.15.i; E.49.l.15.v;
E.49.l.18.i; E.49.l.18.v; E.49.l.25.i; E.49.l.25.v; E.49.m.4.i; E.49.m.4.v; E.49.m.6.i;
E.49.m.6.v; E.49.m.11.i; E.49.m.11.v; E.49.m.14.i; E.49.m.14.v; E.49.m.15.i;
E.49.m.15.v; E.49.m.18.i; E.49.m.18.v; E.49.m.25.i; E.49.m.25.v; E.49.o.4.i;
E.49.o.4.v; E.49.o.6.i; E.49.o.6.v; E.49.o.11.i; E.49.o.11.v; E.49.o.14.i; E.49.o.14v;
E.49.o.15.i; E.49.o.15.v; E.49.o.18.i; E.49.o.18.v; E.49.o.25.i; E.49.o.25.v; H.17.a.4.i;

H.17.a.4.v; H.17.a.6.i; H.17.a.6.v; H.17.a.11.i; H.17.a.11.v; H.17.a.14.i; H.17.a.14.v;
H.17.a.15.i; H.17.a.15.v; H.17.a.18.i; H.17.a.18.v; H.17.a.25.i; H.17.a.25.v;
H.17.e.4.i; H.17.e.4.v; H.17.e.6.i; H.17.e.6.v; H.17.e.11.i; H.17.e.11.v; H.17.e.14.i;
H.17.e.14.v; H.17.e.15.i; H.17.e.15.v; H.17.e.18.i; H.17.e.18.v; H.17.e.25.i;
H.17.e.25.v; H.17.g.4.i; H.17.g.4.v; H.17.g.6.i; H.17.g.6.v; H.17.g.11.i; H.17.g.11.v;
H.17.g.14.i; H.17.g.14.v; H.17.g.15.i; H.17.g.15.v; H.17.g.18.i; H.17.g.18.v;
H.17.g.25.i; H.17.g.25.v; H.17.l.4.i; H.17.l.4.v; H.17.l.6.i; H.17.l.6.v; H.17.l.11.i;
H.17.l.11.v; H.17.l.14.i; H.17.l.14.v; H.17.l.15.i; H.17.l.15.v; H.17.l.18.i;
H.17.l.18.v; H.17.l.25.i; H.17.l.25.v; H.17.m.4.i; H.17.m.4.v; H.17.m.6.i;
H.17.m.6.v; H.17.m.11.i; H.17.m.11.v; H.17.m.14.i; H.17.m.14.v; H.17.m.15.i;
H.17.m.15.v; H.17.m.18.i; H.17.m.18.v; H.17.m.25.i; H.17.m.25.v; H.17.o.4.i;
H.17.o.4.v; H.17.o.6.i; H.17.o.6.v; H.17.o.11.i; H.17.o.11.v; H.17.o.14.i;
H.17.o.14.v; H.17.o.15.i; H.17.o.15.v; H.17.o.18.i; H.17.o.18.v; H.17.o.25.i;
H.17.o.25.v; H.33.a.4.i; H.33.a.4.v; H.33.a.6.i; H.33.a.6.v; H.33.a.11.i; H.33.a.11.v;
H.33.a.14.i; H.33.a.14.v; H.33.a.15.i; H.33.a.15.v; H.33.a.18.i; H.33.a.18.v;
H.33.a.25.i; H.33.a.25.v; H.33.e.4.i; H.33.e.4.v; H.33.e.6.i; H.33.e.6.v; H.33.e.11.i;
H.33.e.11.v; H.33.e.14.i; H.33.e.14.v; H.33.e.15.i; H.33.e.15.v; H.33.e.18.i;
H.33.e.18.v; H.33.e.25.i; H.33.e.25.v; H.33.g.4.i; H.33.g.4.v; H.33.g.6.i; H.33.g.6.v;
H.33.g.11.i; H.33.g.11.v; H.33.g.14.i; H.33.g.14.v; H.33.g.15.i; H.33.g.15.v;
H.33.g.18.i; H.33.g.18.v; H.33.g.25.i; H.33.g.25.v; H.33.l.4.i; H.33.l.4.v; H.33.l.6.i;
H.33.l.6.v; H.33.l.11.i; H.33.l.11.v; H.33.l.14.i; H.33.l.14.v; H.33.l.15.i; H.33.l.15.v;
H.33.l.18.i; H.33.l.18.v; H.33.l.25.i; H.33.l.25.v; H.33.m.4.i; H.33.m.4.v;
H.33.m.6.i; H.33.m.6.v; H.33.m.11.i; H.33.m.11.v; H.33.m.14.i; H.33.m.14.v;
H.33.m.15.i; H.33.m.15.v; H.33.m.18.i; H.33.m.18.v; H.33.m.25.i; H.33.m.25.v;
H.33.o.4.i; H.33.o.4.v; H.33.o.6.i; H.33.o.6.v; H.33.o.11.i; H.33.o.11.v; H.33.o.14.i;
H.33.o.14.v; H.33.o.15.i; H.33.o.15.v; H.33.o.18.i; H.33.o.18.v; H.33.o.25.i;
H.33.o.25.v; H.49.a.4.i; H.49.a.4.v; H.49.a.6.i; H.49.a.6.v; H.49.a.11.i; H.49.a.11.v;
H.49.a.14.i; H.49.a.14.v; H.49.a.15.i; H.49.a.15.v; H.49.a.18.i; H.49.a.18.v;
H.49.a.25.i; H.49.a.25.v; H.49.e.4.i; H.49.e.4.v; H.49.e.6.i; H.49.e.6.v; H.49.e.11.i;
H.49.e.11.v; H.49.e.14.i; H.49.e.14.v; H.49.e.15.i; H.49.e.15.v; H.49.e.18.i;
H.49.e.18.v; H.49.e.25.i; H.49.e.25.v; H.49.g.4.i; H.49.g.4.v; H.49.g.6.i; H.49.g.6.v;
H.49.g.11.i; H.49.g.11.v; H.49.g.14.i; H.49.g.14.v; H.49.g.15.i; H.49.g.15.v;
H.49.g.18.i; H.49.g.18.v; H.49.g.25.i; H.49.g.25.v; H.49.l.4.i; H.49.l.4.v; H.49.l.6.i;
H.49.l.6.v; H.49.l.11.i; H.49.l.11.v; H.49.l.14.i; H.49.l.14.v; H.49.l.15.i; H.49.l.15.v;
H.49.l.18.i; H.49.l.18.v; H.49.l.25.i; H.49.l.25.v; H.49.m.4.i; H.49.m.4.v;
H.49.m.6.i; H.49.m.6.v; H.49.m.11.i; H.49.m.11.v; H.49.m.14.i; H.49.m.14.v;
H.49.m.15.i; H.49.m.15.v; H.49.m.18.i; H.49.m.18.v; H.49.m.25.i; H.49.m.25.v;
H.49.o.4.i; H.49.o.4.v; H.49.o.6.i; H.49.o.6.v; H.49.o.11.i; H.49.o.11.v; H.49.o.14.i;
H.49.o.14.v; H.49.o.15.i; H.49.o.15.v; H.49.o.18.i; H.49.o.18.v; H.49.o.25.i;
H.49.o.25.v; I.17.a.4.i; I.17.a.4.v; I.17.a.6.i; I.17.a.6.v; I.17.a.11.i; I.17.a.11.v;
I.17.a.14.i; I.17.a.14.v; I.17.a.15.i; I.17.a.15.v; I.17.a.18.i; I.17.a.18.v; I.17.a.25.i;
I.17.a.25.v; I.17.e.4.i; I.17.e.4.v; I.17.e.6.i; I.17.e.6.v; I.17.e.11.i; I.17.g.11.v;
I.17.e.14.i; I.17.e.14.v; I.17.e.15.i; I.17.e.15.v; I.17.e.18.i; I.17.e.18.v; I.17.g.25.i;
I.17.e.25.v; I.17.g.4.i; I.17.g.4.v; I.17.g.6.i; I.17.g.6.v; I.17.g.11.i; I.17.g.11.v;
I.17.g.14.i; I.17.g.14.v; I.17.g.15.i; I.17.g.15.v; I.17.g.18.i; I.17.g.18.v; I.17.g.25.i;
I.17.g.25.v; I.17.l.4.i; I.17.l.4.v; I.17.l.6.i; I.17.l.6.v; I.17.l.11.i; I.17.l.11.v; I.17.l.14.i;
I.17.l.14.v; I.17.l.15.i; I.17.l.15.v; I.17.l.18.i; I.17.l.18.v; I.17.l.25.i; I.17.l.25.v;
I.17.m.4.i; I.17.m.4.v; I.17.m.6.i; I.17.m.6.v; I.17.m.11.i; I.17.m.11.v; I.17.m.14.i;
I.17.m.14.v; I.17.m.15.i; I.17.m.15.v; I.17.m.18.i; I.17.m.18.v; I.17.m.25.i;
I.17.m.25.v; I.17.o.4.i; I.17.o.4.v; I.17.o.6.i; I.17.o.6.v; I.17.o.11.i; I.17.o.11.v;
I.17.o.14.i; I.17.o.14.v; I.17.o.15.i; I.17.o.15.v; I.17.o.18.i; I.17.o.18.v; I.17.o.25i;
I.17.o.25.v; I.33.a.4.i; I.33.a.4.v; I.33.a.6.i; I.33.a.6.v; I.33.a.11.i; I.33.a.11.v;
I.33.a.14.i; I.33.a.14.v; I.33.a.15.i; I.33.a.15.v; I.33.a.18.i; I.33.a.18.v; I.33.a.25.i;
I.33.a.25.v; I.33.e.4.i; I.33.e.4.v; I.33.e.6.i; I.33.e.6.v; I.33.e.11.i; I.33.e.11.v;
I.33.e.14.i; I.33.e.14.v; I.33.e.15.i; I.33.e.15.v; I.33.e.18.i; I.33.e.18.v; I.33.e.25.i;
I.33.e.25.v; I.33.g.4.i; I.33.g.4.v; I.33.g.6.i; I.33.g.6.v; I.33.g.11.i; I.33.g.11.v;
I.33.g.14.i; I.33.g.14.v; I.33.g.15.i; I.33.g.15.v; I.33.g.18.i; I.33.g.18.v; I.33.g.25.i;
I.33.g.25.v; I.33.l.4.i; I.33.l.4.v; I.33.l.6.i; I.33.l.6.v; I.33.l.11.i; I.33.l.11.v; I.33.l.14.i;
I.33.l.14.v; I.33.l.15.i; I.33.l.15.v; I.33.l.18.i; I.33.l.18.v; I.33.l.25.i; I.33.l.25.v;
I.33.m.4.i; I.33.m.4.v; I.33.m.6.i; I.33.m.6.v; I.33.m.11.i; I.33.m.11.v; I.33.m.14.i;
I.33.m.14.v; I.33.m.15.i; I.33.m.15.v; I.33.m.18.i; I.33.m.18.v; I.33.m.25.i;
I.33.m.25.v; I.33.o.4.i; I.33.o.4.v; I.33.o.6.i; I.33.o.6.v; I.33.o.11.i; I.33.o.11.v;
I.33.o.14.i; I.33.o.14.v; I.33.o.15.i; I.33.o.15.v; I.33.o.18.i; I.33.o.18.v; I.33.o.25.i;
I.33.o.25.v; I.49.a.4.i; I.49.a.4.v; I.49.a.6.i; I.49.a.6.v; I.49.a.11.i; I.49.a.11.v;
I.49.a.14.i; I.49.a.14.v; I.49.a.15.i; I.49.a.15.v; I.49.a.18.i; I.49.a.18.V; I.49.a.25.i;
I.49.a.25.v; I.49.e.4.i; I.49.e.4.v; I.49.e.6.i; I.49.e.6.v; I.49.e.11.i; I.49.e.11.v;
I.49.e.14.i; I.49.e.14.v.; I.49.e.15.i; I.49.e.15v; I.49.e.18.i; I.49.e.18.v; I49.e.25.i;
I.49.e.25.v; I.49.g.4.i; I.49.g.4.v; I.49.g.6.i; I.49.g.6.v; I.49.g.11.i; I.49.g.11.v;

I.49.g.14.i; I.49.g.14.v; I.49.g.15.i; I.49.g.15.v; I.49.g.18.i; I.49.g.18.v; I.49.g.25.i;
I.49.g.25.v; I.49.l.4.i; I.49.l.4.v; I.49.l.6.i; I.49.l.6.v; I.49.l.11.i; I.49.l.11.v; I.49.l.14.i;
I.49.l.14.v; I.49.l.15.i; I.49.l.15.v; I.49.l.18.i; I.49.l.18.v; I.49.l.25.i; I.49.l.25.v;
I.49.m.4.i; I.49.m.4.v; I.49.m.6.i; I.49.m.6.v; I.49.m.11.i; I.49.m.11.v; I.49.m.14i;
I.49.m.14.v; I.49.m.15.i; I.49.m.15.v; I.49.m.18.i; I.49.m.18.v; I.49.m.25.i;
I.49.m.25.v; I.49.o.4.i; I.49.o.4.v; I.49.o.6.i; I.49.o.6.v; I.49.o.11.i; I.49.o.11.v;
I.49.o.14.i; I.49.o.14.v; I.49.o.15.i; I.49.o.15.v; I.49.o.18.i; I.49.o.18.v; I.49.o.25.i;
I.49.o.25.v; L.17.a.4.i; L.17.a.4.v; L.17.a.6.i; L.17.a.6.v; L.17.a.11.i; L.17.a.11.v;
L.17.a.14.i; L.17.a.14.v; L.17.a.15.i; L.17.a.15.v; L.17.a.18.i; L.17.a.18.v; L.17.a.25.i;
L.17.a.25.v; L.17.e.4.i; L.17.e.4.v; L.17.e.6.i; L.17.e.6.v; L.17.e.11.i; L.17.e.11.v;
L.17.e.14.i; L.17.e.14.v; L.17.e.15.i; L.17.e.15.v; L.17.e.18.i; L.17.e.18.v; L.17.e.25.i;
L.17.e.25.v; L.17.g.4.i; L.17.g.4.v; L.17.g.6.i; L.17.g.6.v; L.17.g.11.i; L.17.g.11.v;
L.17.g.14.i; L.17.g.14.v; L.17.g.15.i; L.17.g.15.v; L.17.g.18.i; L.17.g.18.v; L.17.g.25.i;
L.17.g.25.v; L.17.l.4.i; L.17.l.4.v; L.17.l.6.i; L.17.l.6.v; L.17.l.11.i; L.17.l.11.v;
L.17.l.14.i; L.17.l.14.v; L.17.l.15.i; L.17.l.15.v; L.17.l.18.i; L.17.l.18.v; L.17.l.25.i;
L.17.l.25.v; L.17.m.4.i; L.17.m.4.v; L.17.m.6.i; L.17.m.6.v; L.17.m.11.i;
L.17.m.11.v; L.17.m.14.i; L.17.m.14.v; L.17.m.15.i; L.17.m.15.v; L.17.m.18.i;
L.17.m.18.v; L.17.m.25.i; L.17.m.25.v; L.17.o.4.i; L.17.o.4.v; L.17.o.6.i; L.17.o.6.v;
L.17.o.11.i; L.17.o.11.v; L.17.o.14.i; L.17.o.14.v; L.17.o.15.i; L.17.o.15.v; L.17.o.18.i;
L.17.o.18.v; L.17.o.25.i; L.17.o.25.v; L.33.a.4.i; L.33.a.4.v; L.33.a.6.i; L.33.a.6.v;
L.33.a.11.i; L.33.a.11.v; L.33.a.14.i; L.33.a.14.v; L.33.a.15.i; L.33.a.15.v; L.33.a.18.i;
L.33.a.18.v; L.33.a.25.i; L.33.a.25.v; L.33.e.4.i; L.33.e.4.v; L.33.e.6.i; L.33.e.6.v;
L.33.e.11.i; L.33.e.11.v; L.33.e.14.i; L.33.e.14.v; L.33.e.15.i; L.33.e.15.v; L.33.e.18.i;
L.33.e.18.v; L.33.e.25.i; L.33.e.25.v; L.33.g.4.i; L.33.g.4.v; L.33.g.6.i; L.33.g.6.v;
L.33.g.11.i; L.33.g.11.v; L.33.g.14.i; L.33.g.14.v; L.33.g.15.i; L.33.g.15v; L.33.g.18.i;
L.33.g.18.v; L.33.g.25.i; L.33.g.25.v; L.33.l.4.i; L.33.l.4.v; L.33.l.6.i; L.33.l.6.v;
L.33.l.11.i; L.33.l.11.v; L.33.l.14.i; L.33.l.14.v; L.33.l.15.i; L.33.l.15.v; L.33.l.18.i;
L.33.l.18.v; L.33.l.25.i; L.33.l.25.v; L.33.m.4.i; L.33.m.4.v; L.33.m.6.i; L.33.m.6.v;
L.33.m.11.i; L.33.m.11.v; L.33.m.14.i; L.33.m.14.v; L.33.m.15.i; L.33.m.15.v;
L.33.m.18.i; L.33.m.18.v; L.33.m.25.i; L.33.m.25.v; L.33.o.4.i; L.33.o.4.v; L.33.o.6.i;
L.33.o.6.v; L.33.o.11.i; L.33.o.11.v; L.33.o.14.i; L.33.o.14.v; L.33.o.15.i; L.33.o.15.v;
L.33.o.18.i; L.33.o.18.v; L.33.o.25.i; L.33.o.25.v; L.49.a.4.i; L.49.a.4.v; L.49.a.6.i;
L.49.a.6.v; L.49.a.11.i; L.49.a.11.v; L.49.a.14.i; L.49.a.14.v; L.49.a.15.i; L.49.a.15.v;
L.49.a.18.i; L.49.a.18.v; L.49.a.25.i; L.49.a.25.v; L.49.e.4.i; L.49.e.4.v; L.49.e.6.i;
L.49.e.6.v; L.49.e.11.i; L.49.e.11.v; L.49.e.14.i; L.49.e.14.v; L.49.e.15.i; L.49.e.15.v;
L.49.e.18.i; L.49.e.18.v; L.49.e.25.i; L.49.e.25.v; L.49.g.4.i; L.49.g.4.v; L.49.g.6.i;
L.49.g.6.v; L.49.g.11.i; L.49.g.11.v; L.49.g.14.i; L.49.g.14.v; L.49.g.15.i; L.49.g.15.v;
L.49.g.18.i; L.49.g.18.v; L.49.g.25.i; L.49.g.25.v; L.49.l.4.i; L.49.l.4.v; L.49.l.6.i;
L.49.l.6.v; L.49.l.11.i; L.49.l.11.v; L.49.l.14.i; L.49.l.14.v; L.49.l.15.i; L.49.l.15.v;
L.49.l.18.i; L.49.l.18.v; L.49.l.25.i; L.49.l.25.v; L.49.m.4.i; L.49.m.4.v; L.49.m.6.i;
L.49.m.6.v; L.49.m.11.i; L.49.m.11.v; L.49.m.14.i; L.49.m.14.v; L.49.m.15.i;
L.49.m.15.v; L.49.m.18.i; L.49.m.18.v; L.49.m.25.i; L.49.m.25.v; L.49.o.4.i;
L.49.o.4.v; L.49.o.6.i; L.49.o.6.v; L.49.o.11.i; L.49.o.11.v; L.49.o.14.i; L.49.o.14.v;
L.49.o.15.i; L.49.o.15.v; L.49.o.18.i; L.49.o.18.v; L.49.o.25.i; L.49.o.25.v; B.93.a.4.i;
B.93.a.4.v; B.93.a.6.i; B.93.a.6.v; B.93.a.11.i; B.93.a.11.v; B.93.a.14.i; B.93.a.14.v;
B.93.a.15.i; B.93.a.15.v; B.93.a.18.i; B.93.a.18.v; B.93.a.25.i; B.93.a.25v; B.93.e.4.i;
B.93.e.4.v; B.93.e.6.i; B.93.e.6.v; B.93.e.11.i; B.93.e.11.v; B.93.e.14.i; B.93.e.14.v;
B.93.e.15.i; B.93.e.15.v; B.93.e.18.i; B.93.e.18.v; B.93.e.25.i; B.93.e.25.v; B.93.g.4.i;
B.93.g.4.v; B.93.g.6.i; B.93.g.6.v; B.93.g.11.i; B.93.g.11.v; B.93.g.14.i; B.93.g.14.v;
B.93.g.15.i; B.93.g.15.v; B.93.g.18.i; B.93.g.18.v; B.93.g.25.i; B.93.g.25.v; B.93.l.4.i;
B.93.l.4.v; B.93.l.6.i; B.93.l.6.v; B.93.l.11.i; B.93.l.11.v; B.93.l.14.i; B.93.l.14.v;
B.93.l.15.i; B.93.l.15.v; B.93.l.18.i; B.93.l.18.v; B.93.l.25.i; B.93.l.25.v; B.93.m.4.i;
B.93.m.4.v; B.93.m.6.i; B.93.m.6.v; B.93.m.11.i; B.93.m.11.v; B.93.m.14.i;
B.93.m.14.v; B.93.m.15.i; B.93.m.15.v; B.93.m.18.i; B.93.m.18.v; B.93.m.25.i;
B.93.m.25.v; B.93.o.4.i; B.93.o.4.v; B.93.o.6.i; B.93.o.6.v; B.93.o.11.i; B.93.o.11.v;
B.93.o.14.i; B.93.o.14.v; B.93.o.15.i; B.93.o.15.v; B.93.o.18.i; B.93.o.18.v;
B.93.o.25.i; B.93.o.25.v; B.94.a.4.i; B.94.a.4.v; B.94.a.6.i; B.94.a.6.v; B.94.a.11.i;
B.94.a.11.v; B.94.a.14.i; B.94.a.14.v; B.94.a.15.i; B.94.a.15.v; B.94.a.18.i;
B.94.a.18.v; B.94.a.25.i; B.94.a.25.v; B.94.e.4.i; B.94.e.4.v; B.94.e.6.i; B.94.e.6.v;
B.94.e.11.i; B.94.e.11.v; B.94.e.14.i; B.94.e.14.v; B.94.e.15.i; B.94.e.15.v; B.94.e.18.i;
B.94.e.18.v; B.94.e.25.i; B.94.e.25.v; B.94.g.4.i; B.94.g.4.v; B.94.g.6.i; B.94.g.6.v;
B.94.g.11.i; B.94.g.11.v; B.94.g.14.i; B.94.g.14.v; B.94.g.15.i; B.94.g.15.v; B.94.g.18.i;
B.94.g.18.v; B.94.g.25.i; B.94.g.25.v; B.94.l.4.i; B.94.l.4.v; B.94.l.6.i; B.94.l.6.v;
B.94.l.11.i; B.94.l.11.v; B.94.l.14.i; B.94.l.14.v; B.94.l.15.i; B.94.l.15.v; B.94.l.18.i;
B.94.l.18.v; B.94.l.25.i; B.94.l.25.v; B.94.m.4.i; B.94.m.4.v; B.94.m.6.i; B.94.m.6.v;
B.94.m.11.i; B.94.m.11.v; B.94.m.14.i; B.94.m.14.v; B.94.m.15.i; B.94.m.15.v;
B.94.m.18.i; B.94.m.18.v; B.94.m.25.i; B.94.m.25.v; B.94.o.4.i; B.94.o.4.v;
B.94.o.6.i; B.94.o.6.v; B.94.o.11.i; B.94.o.11.v; B.94.o.14.i; B.94.o.14.v; B.94.o.15.i;

B.94.o.15.v; B.94.o.18.i; B.94.o.18.v; B.94.o.25.i; B.94.o.25.v; E.93.a.4.i; E.93.a.4.v;
E.93.a.6.i; E.93.a.6.v; E.93.a.11.i; E.93.a.11.v; E.93.a.14.i; E.93.a.14.v; E.93.a.15.i;
E.93.a.15.v; E.93.a.18.i; E.93.a.18.v; E.93.a.25.i; E.93.a.25.v; E.93.e.4.i; E.93.e.4.v;
E.93.e.6.i; E.93.e.6.v; E.93.e.11.i; E.93.e.11.v; E.93.e.14.i; E.93.e.14.v; E.93.e.15.i;
E.93.e.15.v; E.93.e.18.i; E.93.e.18.v; E.93.e.25.i; E.93.e.25.v; E.93.g.4.i; E.93.g.4.v;
E.93.g.6.i; E.93.g.6.v; E.93.g.11.i; E.93.g.11.v; E.93.g.14.i; E.93.g.14.v; E.93.g.15.i;
E.93.g.15.v; E.93.g.18.i; E.93.g.18.v; E.93.g.25.i; E.93.g.25.v; E.93.l.4.i; E.93.l.4.v;
E.93.l.6.i; E.93.l.6.v; E.93.l.11.i; E.93.l.11.v; E.93.l.14.i; E.93.l.14.v; E.93.l.15.i;
E.93.l.15.v; E.93.l.18.i; E.93.l.18.v; E.93.l.25.i; E.93.l.25.v; E.93.m.4.i; E.93.m.4.v;
E.93.m.6.i; E.93.m.6.v; E.93.m.11.i; E.93.m.11.v; E.93.m.14.i; E.93.m.14.v;
E.93.m.15.i; E.93.m.15.v; E.93.m.18.i; E.93.m.18.v; E.93.m.25.i; E.93.m.25.v;
E.93.o.4.i; E.93.o.4.v; E.93.o.6.i; E.93.o.6.v; E.93.o.11.i; E.93.o.11.v; E.93.o.14.i;
E.93.o.14.v; E.93.o.15.i; E.93.o.15.v; E.93.o.18.i; E.93.o.18.v; E.93.o.25.i;
E.93.o.25.v; E.94.a.4.i; E.94.a.4.v; E.94.a.6.i; E.94.a.6.v; E.94.a.11.i; E.94.a.11.v;
E.94.a.14.i; E.94.a.14.v; E.94.a.15.i; E.94.a.15.v; E.94.a.18.i; E.94.a.18.v; E.94.a.25.i;
E.94.a.25.v; E.94.e.4.i; E.94.e.4.v; E.94.e.6.i; E.94.e.6.v; E.94.e.11.i; E.94.e.11.v;
E.94.e.14.i; E.94.e.14.v; E.94.e.15.i; E.94.e.15.v; E.94.e.18.i; E.94.e.18.v; E.94.e.25.i;
E.94.e.25.v; E.94.g.4.i; E.94.g.4.v; E.94.g.6.i; E.94.g.6.v; E.94.g.11.i; E.94.g.11.v;
E.94.g.14.i; E.94.g.14.v; E.94.g.15.i; E.94.g.15.v; E.94.g.18.i; E.94.g.18.v; E.94.g.25.i;
E.94.g.25.v; E.94.l.4.i; E.94.l.4.v; E.94.l.6.i; E.94.l.6.v; E.94.l.11.i; E.94.l.11.v;
E.94.l.14.i; E.94.l.14.v; E.94.l.15.i; E.94.l.15.v; E.94.l.18.i; E.94.l.18.v; E.94.l.25.i;
E.94.l.25.v; E.94.m.4.i; E.94.m.4.v; E.94.m.6.i; E.94.m.6.v; E.94.m.11.i;
E.94.m.11.v; E.94.m.14.i; E.94.m.14.v; E.94.m.15.i; E.94.m.15.v; E.94.m.18.i;
E.94.m.18.v; E.94.m.25.i; E.94.m.25.v; E.94.o.4.i; E.94.o.4.v; E.94.o.6.i; E.94.o.6.v;
E.94.o.11.i; E.94.o.11.v; E.94.o.14.i; E.94.o.14.v; E.94.o.15.i; E.94.o.15.v; E.94.o.18.i;
E.94.o.18.v; E.94.o.25.i; E.94.o.25.v; I.93.a.4.i; I.93.a.4.v; I.93.a.6.i; I.93.a.6.v;
I.93.a.11.i; I.93.a.11.v; I.93.a.14.i; I.93.a.14.v; I.93.a.15.i; I.93.a.15.v; I.93.a.18.i;
I.93.a.18.v; I.93.a.25.i; I.93.a.25.v; I.93.e.4.i; I.93.e.4.v; I.93.e.6.i; I.93.e.6.v;
I.93.e.11.i; I.93.e.11.v; I.93.e.14.i; I.93.e.14.v; I.93.e.15.i; I.93.e.15.v; I.93.e.18.i;
I.93.e.18.v; I.93.e.25.i; I.93.e.25.v; I.93.g.4.i; I.93.g.4.v; I.93.g.6.i; I.93.g.6.v;
I.93.g.11.i; I.93.g.11.v; I.93.g.14.i; I.93.g.14.v; I.93.g.15.i; I.93.g.15.v; I.93.g.18.i;
I.93.g.18.v; I.93.g.25.i; I.93.g.25.v; I.93.l.4.i; I.93.l.4.v; I.93.l.6.i; I.93.l.6.v; I.93.l.11.i;
I.93.l.11.v; I.93.l.14.i; I.93.l.14.v; I.93.l.15.i; I.93.l.15.v; I.93.l.18.i; I.93.l.18.v;
I.93.l.25.i; I.93.l.25.v; I.93.m.4.i; I.93.m.4.v; I.93.m.6.i; I.93.m.6.v; I.93.m.11.i;
I.93.m.11.v; I.93.m.14.i; I.93.m.14.v; I.93.m.15.i; I.93.m.15.v; I.93.m.18.i;
I.93.m.18.v; I.93.m.25.i; I.93.m.25.v; I.93.o.4.i; I.93.o.4.v; I.93.o.6.i; I.93.o.6.v;
I.93.o.11.i; I.93.o.11.v; I.93.o.14.i; I.93.o.14.v; I.93.o.15.i; I.93.o.15.v; I.93.o.18.i;
I.93.o.18.v; I.93.o.25.i; I.93.o.25.v; I.94.a.4.i; I.94.a.4.v; I.94.a.6.i; I.94.a.6.v;
I.94.a.11.i; I.94.a.11.v; I.94.a.14.i; I.94.a.14.v; I.94.a.15.i; I.94.a.15.v; I.94.a.18.i;
I.94.a.18.v; I.94.a.25.i; I.94.a.25.v; I.94.e.4.i; I.94.e.4.v; I.94.e.6.i; I.94.e.6.v;
I.94.e.11.i; I.94.e.11.v; I.94.e.14.i; I.94.e.14.v; I.94.e.15.i; I.94.e.15.v; I.94.e.18.i;
I.94.e.18.v; I.94.e.25.i; I.94.e.25.v; I.94.g.4.i; I.94.g.4.v; I.94.g.6.i; I.94.g.6.v;
I.94.g.11.i; I.94.g.11.v; I.94.g.14.i; I.94.g.14.v; I.94.g.15.i; I.94.g.15.v; I.94.g.18.i;
I.94.g.18.v; I.94.g.25.i; I.94.g.25.v; I.94.l.4.i; I.94.l.4.v; I.94.l.6.i; I.94.l.6.v; I.94.l.11.i;
I.94.l.11.v; I.94.l.14.i; I.94.l.14.v; I.94.l.15.i; I.94.l.15.v; I.94.l.18.i; I.94.l.18.v;
I.94.l.25.i; I.94.l.25.v; I.94.m.4.i; I.94.m.4.v; I.94.m.6.i; I.94.m.6.v; I.94.m.11.i;
I.94.m.11.v; I.94.m.14.i; I.94.m.14.v; I.94.m.15.i; I.94.m.15.v; I.94.m.18.i;
I.94.m.18.v; I.94.m.25.i; I.94.m.25.v; I.94.o.4.i; I.94.o.4.v; I.94.o.6.i; I.94.o.6.v;
I.94.o.11.i; I.94.o.11.v; I.94.o.14.i; I.94.o.14.v; I.94.o.15.i; I.94.o.15.v; I.94.o.18.i;
I.94.o.18.v; I.94.o.25.i; I.94.o.25.v; L.93.a.4.i; L.93.a.4.v; L.93.a.6.i; L.93.a.6.v;
L.93.a.11.i; L.93.a.11.v; L.93.a.14.i; L.93.a.14.v; L.93.a.15.i; L.93.a.15.v; L.93.a.18.i;
L.93.a.18.v; L.93.a.25.i; L.93.a.25.v; L.93.e.4.i; L.93.e.4.v; L.93.e.6.i; L.93.e.6.v;
L.93.e.11.i; L.93.e.11.v; L.93.e.14.i; L.93.e.14.v; L.93.e.15.i; L.93.e.15.v; L.93.e.18.i;
L.93.e.18.v; L.93.e.25.i; L.93.e.25.v; L.93.g.4.i; L.93.g.4.v; L.93.g.6.i; L.93.g.6.v;
L.93.g.11.i; L.93.g.11.v; L.93.g.14.i; L.93.g.14.v; L.93.g.15.i; L.93.g.15.v; L.93.g.18.i;
L.93.g.18.v; L.93.g.25.i; L.93.g.25.v; L.93.l.4.i; L.93.l.4.v; L.93.l.6.i; L.93.l.6.v;
L.93.l.11.i; L.93.l.11.v; L.93.l.14.i; L.93.l.14.v; L.93.l.15.i; L.93.l.15.v; L.93.l.18.i;
L.93.l.18.v; L.93.l.25.i; L.93.l.25.v; L.93.m.4.i; L.93.m.4.v; L.93.m.6.i; L.93.m.6.v;
L.93.m.11.i; L.93.m.11.v; L.93.m.14.i; L.93.m.14.v; L.93.m.15.i; L.93.m.15.v;
L.93.m.18.i; L.93.m.18.v; L.93.m.25.i; L.93.m.25.v; L.93.o.4.i; L.93.o.4.v; L.93.o.6.i;
L.93.o.6.v; L.93.o.11.i; L.93.o.11.v; L.93.o.14.i; L.93.o.14.v; L.93.o.15.i; L.93.o.15.v;
L.93.o.18.i; L.93.o.18.v; L.93.o.25.i; L.93.o.25.v; L.94.a.4.i; L.94.a.4.v; L.94.a.6.i;
L.94.a.6.v; L.94.a.11.i; L.94.a.11.v; L.94.a.14.i; L.94.a.14.v; L.94.a.15.i; L.94.a.15.v;
L.94.a.18.i; L.94.a.18.v; L.94.a.25.i; L.94.a.25.v; L.94.e.4.i; L.94.e.4.v; L.94.e.6.i;
L.94.e.6.v; L.94.e.11.i; L.94.e.11.v; L.94.e.14.i; L.94.e.14.v; L.94.e.15.i; L.94.e.15.v;
L.94.e.18.i; L.94.e.18.v; L.94.e.25.i; L.94.e.25.v; L.94.g.4.i; L.94.g.4.v; L.94.g.6.i;
L.94.g.6.v; L.94.g.11.i; L.94.g.11.v; L.94.g.14.i; L.94.g.14.v; L.94.g.15.i; L.94.g.15.v;
L.94.g.18.i; L.94.g.18.v; L.94.g.25.i; L.94.g.25.v; L.94.l.4.i; L.94.l.4.v; L.94.l.6.i;

L.94.l.6.v; L.94.l.11.i; L.94.l.11.v; L.94.l.14.i; L.94.l.14.v; L.94.l.15.i; L.94.l.15.v;
L.94.l.18.i; L.94.l.18.v; L.94.l.25.i; L.94.l.25.v; L.94.m.4.i; L.94.m.4.v; L.94.m.6.i;
L.94.m.6.v; L.94.m.11.i; L.94.m.11.v; L.94.m.14.i; L.94.m.14.v; L.94.m.15.i;
L.94.m.15.v; L.94.m.18.i; L.94.m.18.v; L.94.m.25.i; L.94.m.25.v; L.94.o.4.i;
L.94.o.4.v; L.94.o.6.i; L.94.o.6.v; L.94.o.11.i; L.94.o.11.v; L.94.o.14.i; L.94.o.14.v;
L.94.o.15.i; L.94.o.15.v; L.94.o.18.i; L.94.o.18.v; L.94.o.25.i; L.94.o.25.v; O.93.a.4.i;
O.93.a.4.v; O.93.a.6.i; O.93.a.6.v; O.93.a.11.i; O.93.a.11.v; O.93.a.14.i; O.93.a.14.v;
O.93.a.15.i; O.93.a.15.v; O.93.a.18.i; O.93.a.18.v; O.93.a.25.i; O.93.a.25.e.4.i;
O.93.e.4.v; O.93.e.6.i; O.93.e.6.v; O.93.e.11.i; O.93.e.11.v; O.93.e.14.i; O.93.e.14.v;
O.93.e.15.i; O.93.e.15.v; O.93.e.18.i; O.93.e.18.v; O.93.e.25.i; O.93.e.25.v; O.93.g.4.i;
O.93.g.4.v; O.93.g.6.i; O.93.g.6.v; O.93.g.11.i; O.93.g.11.v; O.93.g.14.i; O.93.g.14.v;
O.93.g.15.i; O.93.g.15.v; O.93.g.18.i; O.93.g.18.v; O.93.g.25.i; O.93.g.25.v; O.93.l.4.i;
O.93.l.4.v; O.93.l.6.i; O.93.l.6.v; O.93.l.11.i; O.93.l.11.v; O.93.l.14.i; O.93.l.14.v;
O.93.l.15.i; O.93.l.15.v; O.93.l.18.i; O.93.l.18.v; O.93.l.25.i; O.93.l.25.v; O.93.m.4.i;
O.93.m.4.v; O.93.m.6.i; O.93.m.6.v; O.93.m.11.i; O.93.m.11.v; O.93.m.14.i;
O.93.m.14.v; O.93.m.15.i; O.93.m.15.v; O.93.m.18.i; O.93.m.18.v; O.93.m.25.i;
O.93.m.25.v; O.93.o.4.i; O.93.o.4.v; O.93.o.6.i; O.93.o.6.v; O.93.o.11.i; O.93.o.11.i;
O.93.o.14.i; O.93.o.14.v; O.93.o.15.i; O.93.o.15.v; O.93.o.18.i; O.93.o.18.v;
O.93.o.25.i; O.93.o.25.v; O.94.a.4.i; O.94.a.4.v; O.94.a.6.i; O.94.a.6.v; O.94.a.11.i;
O.94.a.11.v; O.94.a.14.i; O.94.a.14.v; O.94.a.15.i; O.94.a.15.v; O.94.a.18.i;
O.94.a.18.v; O.94.a.25.i; O.94.a.25.v; O.94.e.4.i; O.94.e.4.v; O.94.e.6.i; O.94.e.6.v;
O.94.e.11.i; O.94.e.11.v; O.94.e.14.i; O.94.e.14.v; O.94.e.15.i; O.94.e.15.v;
O.94.e.18.i; O.94.e.18.v; O.94.e.25.i; O.94.e.25.v; O.94.g.4.i; O.94.g.4.v; O.94.g.6.i;
O.94.g.6.v; O.94.g.11.i; O.94.g.11.v; O.94.g.14.i; O.94.g.14.v; O.94.g.15.i;
O.94.g.15.v; O.94.g.18.i; O.94.g.18.v; O.94.g.25.i; O.94.g.25.v; O.94.l.4.i; O.94.l.4.v;
O.94.l.6.i; O.94.l.6.v; O.94.l.11.i; O.94.l.11.v; O.94.l.14.i; O.94.l.14.v; O.94.l.15.i;
O.94.l.15.v; O.94.l.18.i; O.94.l.18.v; O.94.l.25.i; O.94.l.25.v; O.94.m.4.i; O.94.m.4.v;
O.94.m.6.i; O.94.m.6.v; O.94.m.11.i; O.94.m.11.v; O.94.m.14.i; O.94.m.14.v;
O.94.m.15.i; O.94.m.15.v; O.94.m.18.i; O.94.m.18.v; O.94.m.25.i; O.94.m.25.v;
O.94.o.4.i; O.94.o.4.v; O.94.o.6.i; O.94.o.6.v; O.94.o.11.i; O.94.o.11.v; O.94.o.14.i;
O.94.o.14.v; O.94.o.15.i; O.94.o.15.v; O.94.o.18.i; O.94.o.18.v; O.94.o.25.i;
O.94.o.25.v; P.93.a.4.i; P.93.a.4.v; P.93.a.6.i; P.93.a.6.v; P.93.a.11.i; P.93.a.11.v;
P.93.a.14.i; P.93.a.14.v; P.93.a.15.i; P.93.a.15.v; P.93.a.18.i; P.93.a.18.v; P.93.a.25.i;
P.93.a.25.v; P.93.e.4.i; P.93.e.4.v; P.93.e.6.i; P.93.e.6.v; P.93.e.11.i; P.93.e.11.v;
P.93.e.14.i; P.93.e.14.v; P.93.e.15.i; P.93.e.15.v; P.93.e.18.i; P.93.e.18.v; P.93.e.25.i;
P.93.e.25.v; P.93.g.4.i; P.93.g.4.v; P.93.g.6.i; P.93.g.6.v; P.93.g.11.i; P.93.g.11.v;
P.93.g.14.i; P.93.g.14.v; P.93.g.15.i; P.93.g.15.v; P.93.g.18.i; P.93.g.18.v; P.93.g.25.i;
P.93.g.25.v; P.93.l.4.i; P.93.l.4.v; P.93.l.6.i; P.93.l.6.v; P.93.l.11.i; P.93.l.11.v;
P.93.l.14.i; P.93.l.14.v; P.93.l.15.i; P.93.l.15.v; P.93.l.18.i; P.93.l.18.v; P.93.l.25.i;
P.93.l.25.v; P.93.m.4.i; P.93.m.4.v; P.93.m.6.i; P.93.m.6.v; P.93.m.11.i;
P.93.m.11.v; P.93.m.14.i; P.93.m.14.v; P.93.m.15.i; P.93.m.15.v; P.93.m.18.i;
P.93.m.18.v; P.93.m.25.i; P.93.m.25.v; P.93.o.4.i; P.93.o.4.v; P.93.o.6.i; P.93.o.6.v;
P.93.o.11.i; P.93.o.11.v; P.93.o.14.i; P.93.o.14.v; P.93.o.15.i; P.93.o.15.v; P.93.o.18.i;
P.93.o.18.v; P.93.o.25.i; P.93.o.25.v; P.94.a.4.i; P.94.a.4.v; P.94.a.6.i; P.94.a.6.v;
P.94.a.11.i; P.94.a.11.v; P.94.a.14.i; P.94.a.14.v; P.94.a.15.i; P.94.a.15.v; P.94.a.18.i;
P.94.a.18.v; P.94.a.25.i; P.94.a.25.v; P.94.e.4.i; P.94.e.4.v; P.94.e.6.i; P.94.e.6.v;
P.94.e.11.i; P.94.e.11.v; P.94.e.14.i; P.94.e.14.v; P.94.e.15.i; P.94.e.15.v; P.94.e.18.i;
P.94.e.18.v; P.94.e.25.i; P.94.e.25.v; P.94.g.4.i; P.94.g.4.v; P.94.g.6.i; P.94.g.6.v;
P.94.g.11.i; P.94.g.11.v; P.94.g.14.i; P.94.g.14.v; P.94.g.15.i; P.94.g.15.v; P.94.g.18.i;
P.94.g.18.v; P.94.g.25.i; P.94.g.25.v; P.94.l.4.i; P.94.l.4.v; P.94.l.6.i; P.94.l.6.v;
P.94.l.11.i; P.94.l.11.v; P.94.l.14.i; P.94.l.14.v; P.94.l.15.i; P.94.l.15.v; P.94.l.18.i;
P.94.l.18.v; P.94.l.25.i; P.94.l.25.v; P.94.m.4.i; P.94.m.4.v; P.94.m.6.i; P.94.m.6.v;
P.94.m.11.i; P.94.m.11.v; P.94.m.14.i; P.94.m.14.v; P.94.m.15.i; P.94.m.15.v;
P.94.m.18.i; P.94.m.18.v; P.94.m.25.i; P.94.m.25.v; P.94.o.4.i; P.94.o.4.v; P.94.o.6.i;
P.94.o.6.v; P.94.o.11.i; P.94.o.11.v; P.94.o.14.i; P.94.o.14.v; P.94.o.15.i; P.94.o.15.v;
P.94.o.18.i; P.94.o.18.v; P.94.o.25.i; P.94.o.25.v; A.2.a.4.i; A.2.a.4.o; A.2.a.4.bh;
A.2.a.4.bi; A.2.a.4.bj; A.2.a.4.bk; A.2.a.11.i; A.2.a.11.o; A.2.a.11.bh; A.2.a.11.bi;
A.2.a.11.bj; A.2.a.11.bk; A.2.a.15.i; A.2.a.15.o; A.2.a.15.bh; A.2.a.15.bi; A.2.a.15.bj;
A.2.a.15.bk; A.2.a.37.i; A.2.a.37.o; A.2.a.37.bh; A.2.a.37.bi; A.2.a.37.bj; A,2.a.37.bk;
A.2.a.38.i; A.2.a.38.o; A.2.a.38.bh; A.2.a.38.bi; A.2.a.38.bj; A.2.a.38.bk; A.2.a.39.i;
A.2.a.39.o; A.2.a.39.bh; A.2.a.39.bi; A.2.a.39.bj; A.2.a.39.bk; A.2.a.40.i; A,2.a.40.o;
A.2.a.40.bh; A.2.a.40.bi; A.2.a.40.bj; A.2.a.40.bk; A.2.a.41.i; A.2.a.41.o;
A.2.a.41.bh; A.2.a.41.bi; A.2.a.41.bj; A.2.a.41.bk; A.2.a.42.i; A.2.a.42.o;
A.2.a.42.bh; A.2.a.42.bi; A.2.a.42.bj; A.2.a.42.bk; A.2.a.43.i; A.2.a.43.o;
A.2.a.43.bh; A.2.a.43.bi; A.2.a.43.bj; A.2.a.43.bk;
A.3.a.4.i; A.3.a.4.o; A.3.a.4.bh; A.3.a.4.bi; A.3.a.4.bj; A.3.a.4.bk; A.3.a.11.i;
A.3.a.11.o; A.3.a.11.bh; A.3.a.11.bi; A.3.a.11.bj; A.3.a.11.bk; A.3.a.15.i; A.3.a.15.o;
A.3.a.15.bh; A.3.a.15.bi; A.3.a.15.bj; A.3.a.15.bk; A.3.a.37.i; A.3.a.37.o;

A.3.a.37.bh; A.3.a.37.bi; A.3.a.37.bj; A.3.a.37.bk; A.3.a.38.i; A.3.a.38.o;
A.3.a.38.bh; A.3.a.38.bi; A.3.a.38.bj; A.3.a.38.bk; A.3.a.39.i; A.3.a.39.o;
A.3.a.39.bh; A.3.a.39.bi; A.3.a.39.bj; A.3.a.39.bk; A.3.a.40.i; A.3.a.40.o;
A.3.a.40.bh; A.3.a.40.bi; A.3.a.40.bj; A.3.a.40.bk; A.3.a.41.i; A.3.a.41.o;
A.3.a.41.bh; A.3.a.41.bi; A.3.a.41.bj; A.3.a.41.bk; A.3.a.42.i; A.3.a.42.o;
A.3.a.42.bh; A.3.a.42.bi; A.3.a.42.bj; A.3.a.42.bk; A.3.a.43.i; A.3.a.43.o;
A.3.a.43.bh; A.3.a.43.bi; A.3.a.43.bj; A.3.a.43.bk; A.4.a.4.i; A.4.a.4.o; A.4.a.4.bh;
A.4.a.4.bi; A.4.a.4.bj; A.4.a.4.bk; A.4.a.11.i; A.4.a.11.o; A.4.a.11.bh; A.4.a.11.bi;
A.4.a.11.bj; A.4.a.11.bk; A.4.a.15.i; A.4.a.15.o; A.4.a.15.bh; A.4.a.15.bi; A.4.a.15.bj;
A.4.a.15.bk; A.4.a.37.i; A.4.a.37.o; A.4.a.37.bh; A.4.a.37.bi; A.4.a.37.bj; A.4.a.37.bk;
A.4.a.38.i; A.4.a.38.o; A.4.a.38.bh; A.4.a.38.bi; A.4.a.38.bj; A.4.a.38.bk; A.4.a.39.i;
A.4.a.39.o; A.4.a.39.bh; A.4.a.39.bi; A.4.a.39.bj; A.4.a.39.bk; A.4.a.40.i; A.4.a.40.o;
A.4.a.40.bh; A.4.a.40.bi; A.4.a.40.bj; A.4.a.40.bk; A.4.a.41.i; A.4.a.41.o;
A.4.a.41bh; A.4.a.41.bi; A.4.a.41.bj; A.4.a.41.bk; A.4.a.42.i; A.4.a.42.o;
A.4.a.42.bh; A.4.a.42.bi; A.4.a.42.bj; A.4.a.42.bk; A.4.a.43.i; A.4.a.43.o;
A.4.a.43.bh; A.4.a.43.bi; A.4.a.43.bj; A.4.a.43.bk; A.7.a.4.i; A.7.a.4.o; A.7.a.4.bh;
A.7.a.4.bi; A.7.a.4.bj; A.7.a.4.bk; A.7.a.11.i; A.7.a.11.o; A.7.a.11.bh; A.7.a.11.bi;
A.7.a.11.bj; A.7.a.11.bk; A.7.a.15.i; A.7.a.15.o; A.7.a.15.bh; A.7.a.15.bi; A.7.a.15.bj;
A.7.a.15.bk; A.7.a.37.i; A.7.a.37.o; A.7.a.37.bh; A.7.a.37.bi; A.7.a.37.bj; A.7.a.37.bk;
A.7.a.38.i; A.7.a.38.o; A.7.a.38.bh; A.7.a.38.bi; A.7.a.38.bj; A.7.a.38.bk; A.7.a.39.i;
A.7.a.39.o; A.7.a.39.bh; A.7.a.39.bi; A.7.a.39.bj; A.7.a.39.bk; A.7.a.40.i; A.7.a.40.o;
A.7.a.40.bh; A.7.a.40.bi; A.7.a.40.bj; A.7.a.40.bk; A.7.a.41.i; A.7.a.41.o;
A.7.a.41.bh; A.7.a.41.bi; A.7.a.41.bj; A.7.a.41.bk; A.7.a.42.i; A.7.a.42.o;
A.7.a.42.bh; A.7.a.42.bi; A.7.a.42.bj; A.7.a.42.bk; A.7.a.43.i; A.7.a.43.o;
A.7.a.43.bh; A.7.a.43.bi; A.7.a.43.bj; A.7.a.43.bk;
A.17.a.4.i; A.17.a.4.o; A.17.a.4.bh; A.17.a.4.bi; A.17.a.4.bj; A.17.a.4.bk; A.17.a.11.i;
A.17.a.11.o; A.17.a.11.bh; A.17.a.11.bi; A.17.a.11.bj; A.17.a.11.bk; A.17.a.15.i;
A.17.a.15.o; A.17.a.15.bh; A.17.a.15.bi; A.17.a.15.bj; A.17.a.15.bk; A.17.a.37.i;
A.17.a.37.o; A.17.a.37.bh; A.17.a.37.bi; A.17.a.37.bj; A.17.a.37.bk; A.17.a.38.i;
A.17.a.38.o; A.17.a.38.bh; A.17.a.38.bi; A.17.a.38.bj; A.17.a.38.bk; A.17.a.39.i;
A.17.a.39.o; A.17.a.39.bh; A.17.a.39.bi; A.17.a.39.bj; A.17.a.39.bk; A.17.a.40.i;
A.17.a.40.o; A.17.a.40.bh; A.17.a.40.bi; A.17.a.40.bj; A.17.a.40.bk; A.17.a.41.i;
A.17.a.41.o; A.17.a.41.bh; A.17.a.41.bi; A.17.a.41.bj; A.17.a.41.bk; A.17.a.42.i;
A.17.a.42.o; A.17.a.42.bh; A.17.a.42.bi; A.17.a.42.bj; A.17.a.42.bk; A.17.a.43.i;
A.17.a.43.o; A.17.a.43.bh; A.17.a.43.bi; A.17.a.43.bj; A.17.a.43.bk; A.18.a.4.i;
A.18.a.4.o; A.18.a.4.bh; A.18.a.4.bi; A.18.a.4.bj; A.18.a.4.bk; A.18.a.11.i;
A.18.a.11.o; A.18.a.11.bh; A.18.a.11.bi; A.18.a.11.bj; A.18.a.11.bk; A.18.a.15.i;
A.18.a.15.o; A.18.a.15.bh; A.18.a.15.bi; A.18.a.15.bj; A.18.a.15.bk; A.18.a.37.i;
A.18.a.37.o; A.18.a.37.bh; A.18.a.37.bi; A. 18.a.37.bj; A.18.a.37.bk; A.18.a.38.i;
A.18.a.38.o; A.18.a.38.bh; A.18.a.38.bi; A.18.a.38.bj; A.18.a.38.bk; A.18.a.39.i;
A.18.a.39.o; A.18.a.39.bh; A.18.a.39.bi; A.18.a.39.bj; A.18.a.39.bk; A.18.a.40.i;
A.18.a.40.o; A.18.a.40.bh; A.18.a.40.bi; A.18.a.40.bj; A.18.a.40.bk; A.18.a.41.i;
A.18.a.41.o; A.18.a.41.bh; A.18.a.41.bi; A.18.a.41.bj; A.18.a.41.bk; A.18.a.42.i;
A.18.a.42.o; A.18.a.42.bh; A.18.a.42.bi; A.18.a.42.bj; A.18.a.42.bk; A.18.a.43.i;
A.18.a.43.o; A.18.a.43.bh; A.18.a.43.bi; A. 18.a.43.bj; A.18.a.43.bk; A.19.a.4.i;
A.19.a.4.o; A.19.a.4.bh; A.19.a.4.bi; A.19.a.4.bj; A.19.a.4.bk; A.19.a.11.i;
A.19.a.11.o; A.19.a.11.bh; A.19.a.11.bi; A.19.a.11.bj; A.19.a.11.bk; A.19.a.15.i;
A.19.a.15.o; A.19.a.15.bh; A.19.a.15.bi; A.19.a.15.bj; A.19.a.15.bk; A.19.a.37.i;
A.19.a.37.o; A.19.a.37.bh; A.19.a.37.bi; A.19.a.37.bj; A.19.a.37.bk; A.19.a.38.i;
A.19.a.38.o; A.19.a.38.bh; A.19.a.38.bi; A.19.a.38.bj; A.19.a.38.bk; A.19.a.39.i;
A.19.a.39.o; A.19.a.39.bh; A.19.a.39.bi; A.19.a.39.bj; A.19.a.39.bk; A.19.a.40.i;
A.19.a.40.o; A.19.a.40.bh; A.19.a.40.bi; A.19.a.40.bj; A.19.a.40.bk; A.19.a.42.i;
A.19.a.41.o; A.19.a.41.bh; A.19.a.41bi; A.19.a.41.bj; A.19.a.41.bk; A.19.a.42.i;
A.19.a.42.o; A.19.a.42.bh; A.19.a.42.bi; A.19.a.42.bj; A.19.a.42.bk; A.19.a.43.i;
A.19.a.43.o; A.19.a.43.bh; A.19.a.43.bi; A.19.a.43.bj; A.19.a.43.bk; A.97.a.4.i;
A.97.a.4.o; A.97.a.4.bh; A.97.a.4.bi; A.97.a.4.bj; A.97.a.4.bk; A.97.a.11.i;
A.97.a.11.o; A.97.a.11.bh; A.97.a.11.bi; A.97.a.11.bj; A.97.a.11.bk; A.97.a.15.i;
A.97.a.15.o; A.97.a.15.bh; A.97.a.15.bi; A.97.a.15.bj; A.97.a.15.bk; A.97.a.37.i;
A.97.a.37.o; A.97.a.37.bh; A.97.a.37.bi; A.97.a.37.bj; A.97.a.37.bk; A.97.a.38.i;
A.97.a.38.o; A.97.a.38.bh; A.97.a.38.bi; A.97.a.38.bj; A.97.a.38.bk; A.97.a.39.i;
A.97.a.39.o; A.97.a.39.bh; A.97.a.39.bi; A.97.a.39.bj; A.97.a.39.bk; A.97.a.40.i;
A.97.a.40.o; A.97.a.40.bh; A.97.a.40.bi; A.97.a.40.bj; A.97.a.40.bk; A.97.a.41.i;
A.97.a.41.o; A.97.a.41.bh; A.97.a.41.bi; A.97.a.41.bj; A.97.a.41.bk; A.97.a.42.i;
A.97.a.42.o; A.97.a.42.bh; A.97.a.42.bi; A.97.a.42.bj; A.97.a.42.bk; A.97.a.43.i;
A.97.a.43.o; A.97.a.43.bh; A.97.a.43.bi; A.97.a.43.bj; A.97.a.43.bk; A.98.a.4.i;
A.98.a.4.o; A.98.a.4.bh; A.98.a.4.bi; A.98.a.4.bj; A.98.a.4.bk; A.98.a.11.i;
A.98.a.11.o; A.98.a.11.bh; A.98.a.11.bi; A.98.a.11.bj; A.98.a.11.bk; A.98.a.15.i;
A.98.a.15.o; A.98.a.15.bh; A.98.a.15.bi; A.98.a.15.bj; A.98.a.15.bk; A.98.a.37.i;

A.98.a.37.o; A.98.a.37.bh; A.98.a.37.bi; A.98.a.37.bj; A.98.a.37.bk; A.98.a.38.i;
A.98.a.38.o; A.98.a.38.bh; A.98.a.38.bi; A.98.a.38.bj; A.98.a.38.bk; A.98.a.39.i;
A.98.a.39.o; A.98.a.39.bh; A.98.a.39.bi; A.98.a.39.bj; A.98.a.39.bk; A.98.a.40.i;
A.98.a.40.o; A.98.a.40.bh; A.98.a.40.bi; A.98.a.40.bj; A.98.a.40.bk; A.98.a.41.i;
A.98.a.41.o; A.98.a.41.bh; A.98.a.41.bi; A.98.a.41.bj; A.98.a.41.bk; A.98.a.42.i;
A.98.a.42.o; A.98.a.42.bh; A.98.a.42.bi; A.98.a.42.bj; A.98.a.42.bk; A.98.a.43.i;
A.98.a.43.o; A.98.a.43.bh; A.98.a.43.bi; A.98.a.43.bj; A.98.a.43.bk;

Screens for Neuraminidase Inhibitors

Compositions of the invention are screened for inhibitory activity against neuraminidase by any of the conventional techniques for evaluating enzyme activity. Within the context of the invention, typically compositions are first screened for inhibition of neuraminidase in vitro and compositions showing inhibitory activity are then screened for activity in vivo. Compositions having in vitro Ki (inhibitory constants) of less then about $5\times10^{-6}$M, typically less than about $5\times10^{-7}$M and preferably less than about $5\times10^{-8}$M are preferred for in vivo use.

Useful in vitro screens have been described in detail and will not be elaborated here. However, Itzstein, M. von et aL.; *Nature* 1993, 363(6428), 418–423, in particular page 420, column 2, full paragraph 3, to page 421, column 2, first partial paragraph, describes a suitable in vitro assay of Potier, M.; et al.; *Analyt. Biochem.* 1979, 94, 287–296, as modified by Chong, A. K. J.; et al.; *Biochem. Biophys. Acta* 1991, 1077, 65–71;and Colman, P. M.; et al.; International Publication No. WO 92/06691 (Int. App. No. PCT/AU90/00501, publication date Apr. 30, 1992) page 34, line 13, to page 35, line 16, describes another useful in vitro screen.

In vivo screens have also been described in detail, see Itzstein, M. von et al.; op. cit., in particular page 421, column 2, first full paragraph, to page 423, column 2, first partial paragraph, and Colman, P. M.; et al.; op. cit. page 36, lines 1–38, describe suitable in vivo screens.

Pharmaceutical Formulations.

Another aspect of the invention relates to compositions comprising one or more pharmaceutically-acceptable carriers. One or more compounds of the invention (herein referred to as the active ingredients) are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient.

While it is possible for the active ingredients to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in Remington's Pharmaceutical Sciences (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the invention suitable for oral administration are prepared as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues e.g. mouth and skin, the formulations are preferably applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10% particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis of influenza A or B infections as described below.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

Effective dose of active ingredient depends at least on the nature of the condition being treated, toxicity, whether the compound is being used prophylactically (lower doses) or against an active influenza infection, the method of delivery, and the pharmaceutical formulation, and will be determined by the clinician using conventional dose escalation studies. It can be expected to be from about 0.001 to about 30 mg/kg body weight per day. For example, for inhalation the daily candidate dose for an adult human of approximately 70 kg body weight will range from 1 mg to 1000 mg, preferably between 5 mg and 500 mg, and may take the form of single or multiple doses.

Active ingredients of the invention are also used in combination with other active ingredients. Such combinations are selected based on the condition to be treated, cross-reactivities of ingredients and pharmaco-properties of the combination. For example, when treating viral infections of the respiratory system, in particular influenza infection, the compositions of the invention are combined with anti-virals (such as amantidine, rimantadine and ribavirin), mucolytics, expectorants, bronchialdilators, antibiotics, antipyretics, or analgesics. Ordinarily, antibiotics, antipyretics, and analgesics are administered together with the compounds of this invention.

Methods of Inhibition of Neuraminidase.

Another aspect of the invention relates to methods of inhibiting the activity of neuraminidase comprising the step of treating a sample suspected of containing neuraminidase with a composition of the invention.

Within the context of the invention samples suspected of containing neuraminidase include natural or man-made materials such as living organisms; tissue or cell cultures; biological samples such as biological material samples (blood, serum, urine, cerebrospinal fluid, tears, sputum, saliva, tissue samples, and the like); laboratory samples; food, water, or air samples; bioproduct samples such as extracts of cells, particularly recombinant cells synthesizing a desired glycoprotein; and the like. Typically the sample will be suspected of containing an organism which produces neuraminidase, frequently a pathogenic organism such as a virus. Samples can be contained in any medium including water and organic solvent/water mixtures. Samples include living organisms such as humans, and man made materials such as cell cultures.

The treating step of the invention comprises adding the composition of the invention to the sample or it comprises adding a precursor of the composition to the sample. The addition step comprises any method of administration as described above.

If desired, the activity of neuraminidase after application of the composition can be observed by any method including direct and indirect methods of detecting neuraminidase activity. Quantitative, qualitative, and semiquantitative methods of determining neuraminidase activity are all contemplated. Typically one of the screening methods described above are applied, however, any other method such as observation of the physiological properties of a living organism are also applicable.

Organisms that contain neuraminidase include bacteria (*Vibrio cholerae, Clostridium perfringens, Streptococcus pneumoniae*, and *Arthrobacter sialophilus*) and viruses (especially orthomyxoviruses or paramyxoviruses such as influenza virus A and B, parainfluenza virus, mumps virus, Newcastle disease virus, fowl plague virus, and sendai virus). Inhibition of neuraminidase activity obtained from or found within any of these organisms is within the objects of this invention. The virology of influenza viruses is described in "Fundamental Virology" (Raven Press, New York, 1986), Chapter 24.

Metabolites of the Compounds of the Invention

Also falling within the scope of this invention are the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. $C^{14}$ or $H^3$) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no neuraminidase inhibitory activity of their own.

Uses for the Compounds of This Invention.

The compounds of this invention, or the biologically active substances produced from these compounds by hydrolysis or metabolism in vivo, are used as immunogens or components of immunogenic compositions to prepare antibodies capable of binding specifically to the compounds or their metabolic products which retain immunologically recognized epitopes (sites of antibody binding). The immunogenic compositions therefore are useful as intermediates in the preparation of antibodies for use in diagnostic, quality control, or the like, methods or in assays for the compounds or their novel metabolic products. In addition, the compounds are useful for raising antibodies against otherwise non-immunogenic polypeptides, in that the compounds serve as haptenic sites stimulating an immune response.

The hydrolysis products of interest include products of the hydrolysis of the protected acidic and basic groups discussed above. In preferred embodiments the acidic or basic amides comprising immunogenic polypeptides such as albumin keyhole limpet hemocyamin and others described below generally are useful as immunogens. The metabolic products described above may retain a substantial degree of immunological cross reactivity with the compounds of the invention. Thus, the antibodies of this invention will be capable of binding to the unprotected compounds of the invention without binding to the protected compounds; alternatively the metabolic products, will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN═C═Nalk are useful in preparing the conjugates of this invention. The conjugates comprise a compound of the invention attached by a bond or a linking group of 1–100, typically, 1–25, more typically 1–10 carbon atoms to the immunogenic substance. The conjugates are separated from starting materials and by products using chromatography or the like, and then are sterile filtered and vialed for storage.

The compounds of this invention are cross-linked for example through any one or more of the following groups: a hydroxyl group of $U_1$; a carboxyl group of $E_1$; a carbon atom of $U_1$, $E_1$, $G_1$, or $T_1$, in substitution of H; and an amine group of $G_1$. Included within such compounds are amides of polypeptides where the polypeptide serves as an above-described protecting or $R_{6a}$ or $R_{6b}$ groups.

Animals are typically immunized against the immunogenic conjugates or derivatives and antisera or monoclonal antibodies prepared in conventional fashion.

Compositions of the invention act as inhibitors of neuraminidase. As such the compositions will bind to locations on the surface or in a cavity of neuraminidase having a geometry unique to neuraminidase. Compositions binding neuraminidase may bind with varying degrees of reversibility. Those compounds binding substantially irreversibly are ideal candidates for use in this method of the invention. Once labeled, the substantially irreversibly binding compositions are useful as probes for the detection of neuraminidase. Accordingly, the invention relates to methods of detecting neuraminidase in a sample suspected of containing neuraminidase comprising the steps of: treating a sample suspected of containing neuraminidase with a composition comprising a compound of the invention bound to a label; and observing the effect of the sample on the activity of the label. Suitable labels are well known in the diagnostics field and include stable free radicals, fluorophores, radioisotopes, enzymes, chemiluminescent groups and chromogens. The compounds herein are labeled in conventional fashion using functional groups such as hydroxyl or amino.

The compounds of the invention are useful for maintaining the structural integrity of glycoproteins in recombinant cell culture, i.e. they are added to fermentations in which glycoproteins are being produced for recovery so as to inhibit neuraminidase catalyzed cleavage of the desired glycoproteins.

The compounds of the invention are polyfunctional. As such they represent a unique class of monomers for the synthesis of polymers. By way of example and not limitation, the polymers prepared from the compounds of this invention include polyamides and polyesters.

The present compounds are used as monomers to provide access to polymers having unique pendent functionalities. The compounds of this invention are useful in homopolymers, or as comonomers with monomers which do not fall within the scope of the invention. Homopolymers of the compounds of this invention will have utility as cation exchange agents (polyesters) in the preparation of molecular sieves (polyamides), textiles, fibers, films, formed articles and the like where the acid functionality $E_1$ is esterified to a hydroxyl group in $U_1$, for example, whereby the pendant basic group $G_1$ is capable of binding acidic functionalities such as are found in polypeptides whose purification is desired. Polyamides are prepared by cross-linking $E_1$ and $G_1$, with $U_1$ remaining free to function as a hydrophilic or hydrophobic affinity group, depending up the selection of the $U_1$ group. The preparation of these polymers from the compounds of the invention is conventional per se.

The compounds of the invention are also a unique class of polyfunctional surfactants. Particularly when $U_1$ does not contain a hydrophilic substituent and is alkyl or alkoxy, $J_1$ is H and $T_1$ is N-acetyl or the like, the compounds have the properties of bi-functional surfactants. As such they have useful surfactant, surface coating, emulsion modifying, rheology modifying and surface wetting properties.

As polyfunctional compounds with defined geometry and carrying simultaneously polar and non-polar moieties, the compounds of the invention are useful as a unique class of phase transfer agents. By way of example and not limitation, the compounds of the invention are useful in phase transfer catalysis and liquid/liquid ion extraction (LIX).

The compounds of the invention optionally contain asymmetric carbon atoms in groups $U_1$, $E_1$, $G_1$, and $T_1$. As such, they are a unique class of chiral auxiliaries for use in the synthesis or resolution of other optically active materials. For example, a racemic mixture of carboxylic acids can be resolved into its component enantiomers by: 1) forming a mixture of diastereomeric esters or amides with a compound of the invention wherein $U_1$ is an asymmetric hydroxyalkane or amino alkane group; 2) separating the diastereomers; and 3) hydrolyzing the ester structure. Racemic alcohols are separated by ester formation with an acid group of $E_1$. Further, such a method can be used to resolve the compounds of the invention themselves if optically active acids or alcohols are used instead of racemic starting materials.

The compounds of this invention are useful as linkers or spacers in preparing affinity absorption matrices, immobilized enzymes for process control, or immunoassay reagents. The compounds herein contain a multiplicity of functional groups that are suitable as sites for cross-linking desired substances. For example, it is conventional to link affinity reagents such as hormones, peptides, antibodies, drugs, and the like to insoluble substrates. These insolublized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

Many functional groups in the compounds of this invention are suitable for use in cross-linking. For example, the carboxylic or phosphonic acid of group $E_1$ is used to form esters with alcohols or amides with amines of the reagent to be cross-linked. The $G_1$ sites substituted with OH, $NHR_1$, SH, azido (which is reduced to amino if desired before cross-linking), CN, $NO_2$, amino, guanidino, halo and the like are suitable sites. Suitable protection of reactive groups will be used where necessary while assembling the cross-linked reagent to prevent polymerization of the bifunctional compound of this invention. In general, the compounds here are used by linking them through carboxylic or phosphonic acid to the hydroxyl or amino groups of the first linked partner, then covalently bonded to the other binding partner through a $T_1$ or $G_1$ group. For example a first binding partner such as a steroid hormone is esterified to the carboxylic acid of a compound of this invention and then this conjugate is cross-linked through a $G_1$ hydroxyl to cyanogen bromide activated Sepaharose, whereby immobilized steroid is obtained. Other chemistries for conjugation are well known. See for example Maggio, "Enzyme-Inmunoassay" (CRC, 1988, pp 71–135) and references cited therein.

As noted above, the therapeutically useful compounds of this invention in which the $W_1$, or $G_1$ carboxyl, hydroxyl or amino groups are protected are useful as oral or sustained release forms. In these uses the protecting group is removed in vivo e.g., hydrolyzed or oxidized, so as to yield the free carboxyl, amino or hydroxyl. Suitable esters or amides for this utility are selected based on the substrate specificity of esterases and/or carboxypeptidases expected to be found within cells where precursor hydrolysis is desired. To the extent that the specificity of these enzymes is unknown, one will screen a plurality of the compounds of this invention until the desired substrate specificity is found. This will be apparent from the appearance of free compound or of antiviral activity. One generally selects amides or esters of the invention compound that are (i) not hydrolyzed or hydrolyzed comparatively slowly in the upper gut, (ii) gut and cell permeable and (iii) hydrolyzed in the cell cytoplasm and/or systemic circulation. Screening assays preferably use cells from particular tissues that are susceptible to influenza infection, e.g. the mucous membranes of the bronchopulmonary tract. Assays known in the art are suitable for determining in vivo bioavailability including intestinal lumen stability, cell permeation, liver homogenate stability and plasma stability assays. However, even if the ester, amide or other protected derivatives are not converted in vivo to the free carboxyl, amino or hydroxyl groups, they remain useful as chemical intermediates.

Exemplary Methods of Making the Compounds of the Invention.

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

A number of exemplary methods for the preparation of the compositions of the invention are provided below. These methods are intended to illustrate the nature of such preparations are not intended to limit the scope of applicable methods.

Generally, the reaction conditions such as temperature, reaction time, solvents, workup procedures, and the like, will be those common in the art for the particular reaction to be performed. The incorporated reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

One exemplary method of preparing the compounds of the invention is shown in Schemes 1a and 1b below. A detailed description of the methods is found in the Experimental section below.

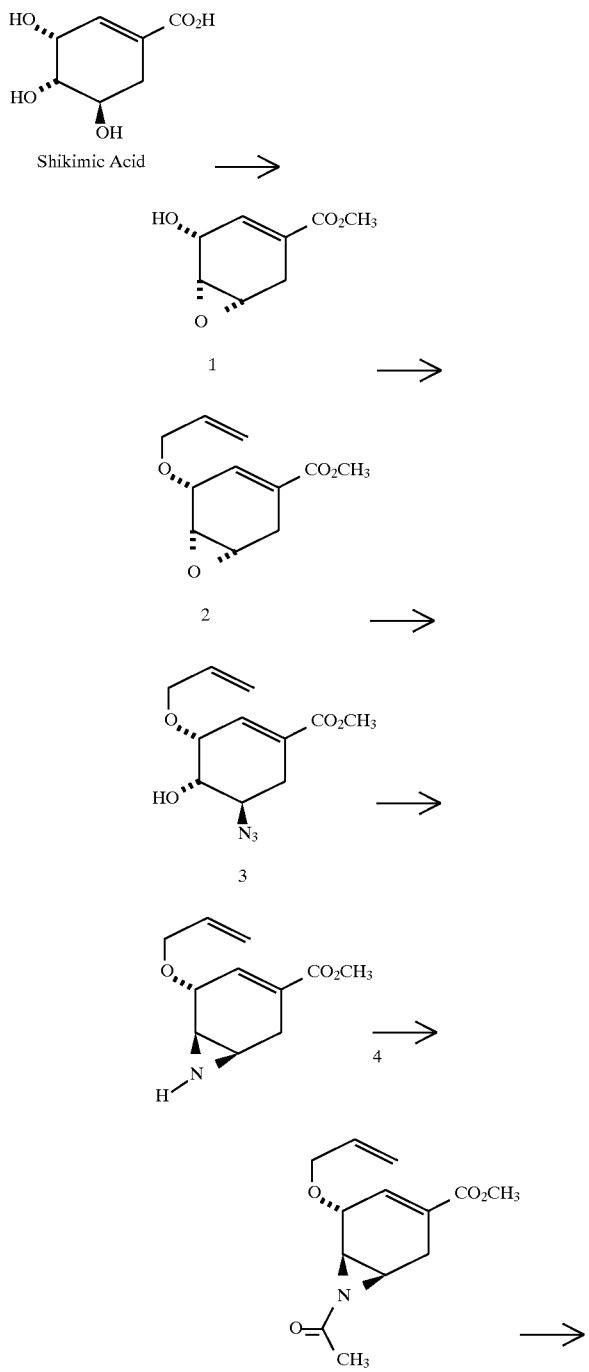

Scheme 1b

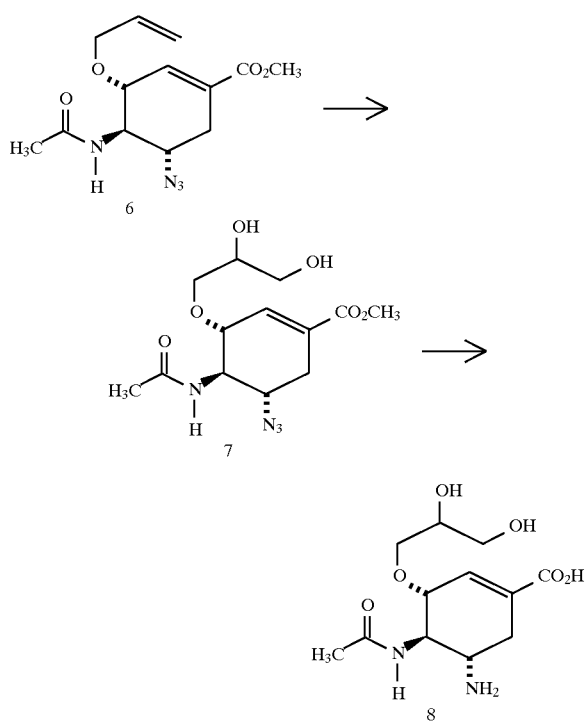

Modifications of Schemes 1a and 1b to form additional embodiments is shown in Schemes 2–4.

Scheme 2

Aziridine 5 is converted to the amino nitrile 9 by $Yb(CN)_3$ catalyzed addition of TMSCN according to the procedure of Utimoto and co-workers, *Tetrahedron Lett.*1990, 31, 6379.

Conversion of nitrile 9 to the corresponding amidine 10 is accomplished using a standard three step sequence: i) $H_2S$; ii) $CH_3I$; iii) $NH_4OAc$. A typical conversion is found in *J. Med. Chem.* 1993, 36, 1811.

Nitrile 9 is converted to the amino methyl compound 11 by reduction using any of the available methods found in "Modern Synthetic Reactions" 2nd ed. H.O. House, Benjamin/Cummings Publishing Co., 1972.

Amino methyl compound 11 is converted to the bis-Boc protected guanidino compound 12 by treating 11 with N,N'-bis-Boc-1H-pyrazole-1-carboxamidine according to the method found in *Tetrahedron Lett.* 1995, 36, 299.

Scheme 2

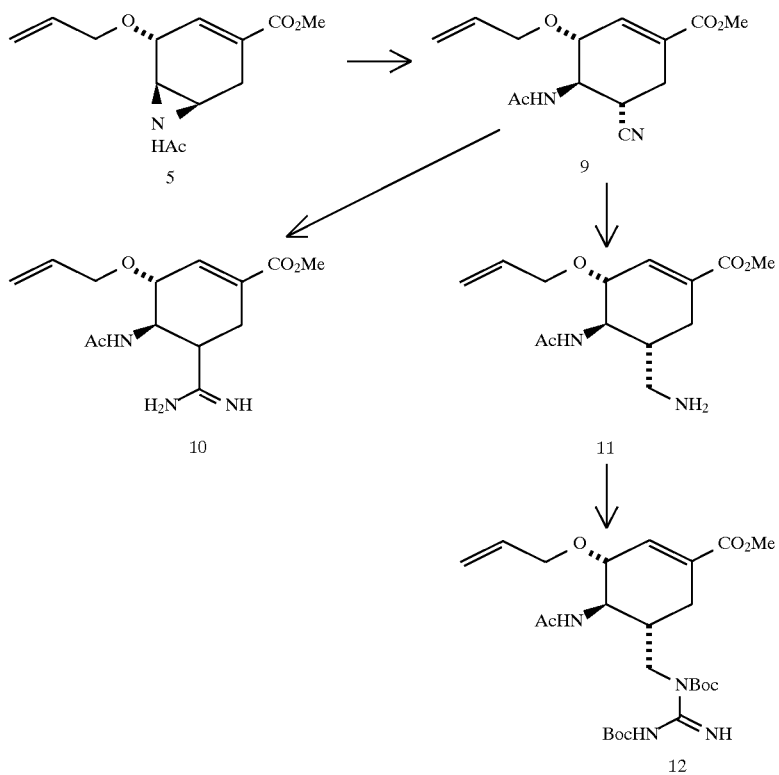

Scheme 3

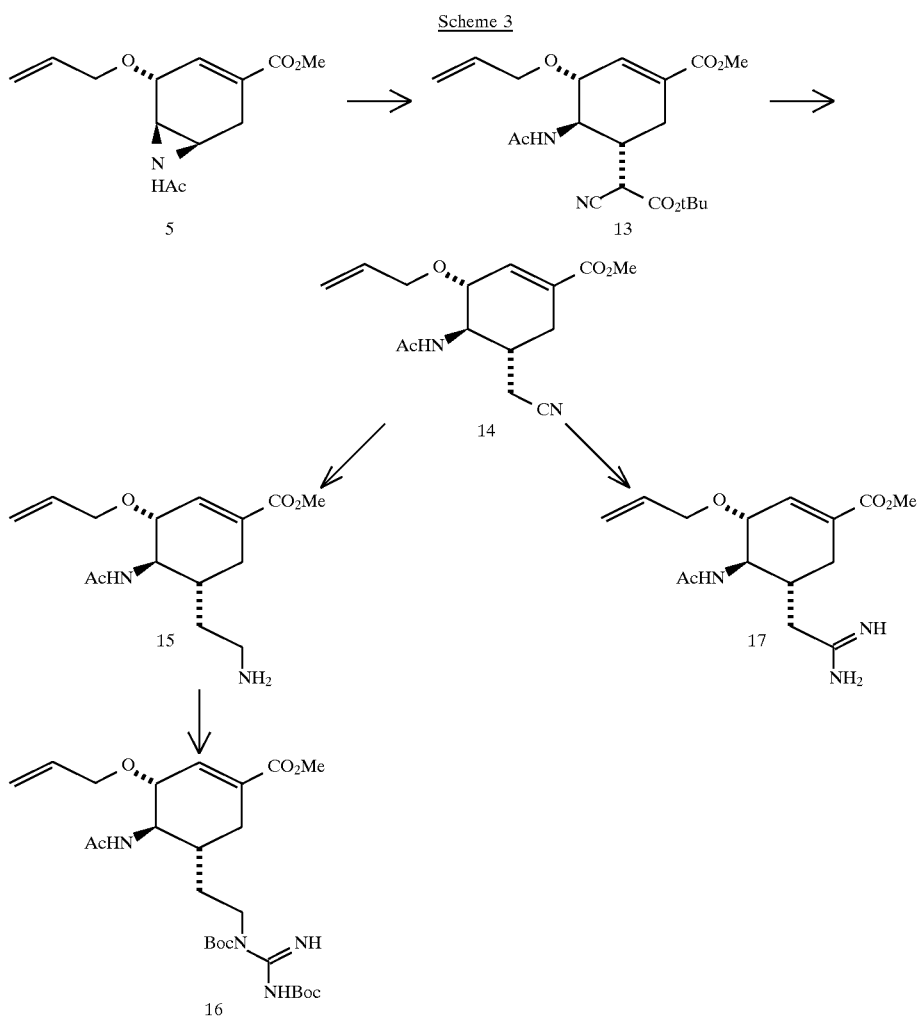

Scheme 3

The aziridine 5 is opened with a-cyano acetic acid t-butyl ester to give 13. Aziridine openings of this type are found in *Tetrahedron Lett*.1982, 23, 5021. Selective hydrolysis of the t-butyl ester moiety under acidic condtions followed by decarboxylation gives nitrile 14.

Reduction of 14 to the amino ethyl derivative 15 is accomplished in the same fashion as the conversion of 9 to 11. The amine 15 is then converted into the guanidino derivative 16 with N,N'-bis-Boc-1H-pyrazole-1-carboxamidine according to the method found in *Tetrahedron Lett*.1995, 36, 299.

The nitrile 14 is converted to the corresponding amidine 17 using the same sequence described above for the conversion of 9 to 10.

Scheme 4

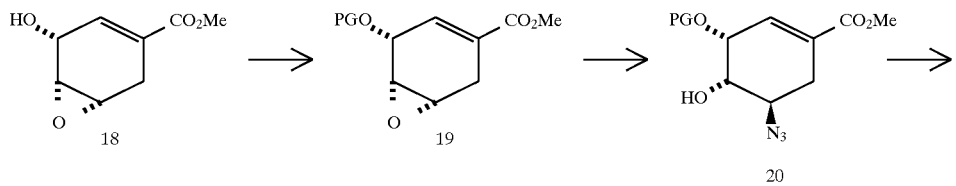

-continued
Scheme 4

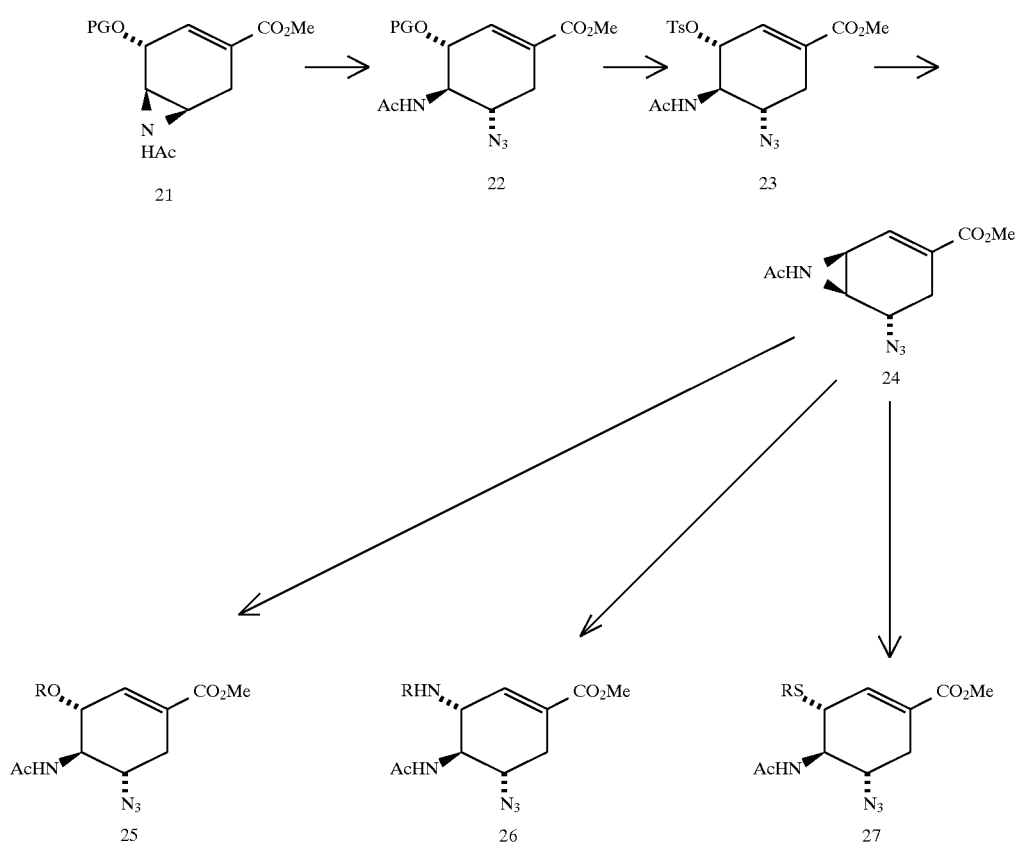

Scheme 4

The epoxy alcohol 18 is protected (PG=protecting group) with MOMCl, typical conditions are found in "Protective Groups in Organic Synthesis" 2nd ed.,T. W. Greene and P. G. M. Wuts, John Wiley & Sons, New York, N.Y., 1991.

The epoxide 19 is opened with $NaN_3/NH_4Cl$ to the amino alcohol 20 according to the procedure of Sharpless and co-workers, J. Org. Chem.1985, 50, 1557.

Reduction of 20 to the N-acetyl aziridine 21 is accomplished in a three step sequence: 1) MsCl/triethyl amine; 2) $H_2$/Pd; 3) AcCl/pyridine. Such transformations can be found in Angew. Chem. Int. Ed. Engl. 1994, 33, 599.

Aziridine 21 is converted to the azido amide 22 by opening with $NaN_3/NH_4Cl$ in DMF at 65° C. as described in J. Chem. Soc. Perkin Trans I, 1976,801.

Removal of the MOM protecting group of 22 is accomplished using the methods described in "Protective Groups in Organic Synthesis" 2nd ed.,T. W. Greene and P. G. M. Wuts, John Wiley & Sons, New York, N.Y., 1991. The resulting alcohol is converted directly to aziridine 24 with TsCl in pyridine. Such transformations are found in Angew. Chem. Int. Ed. Engl. 1994, 33, 599.

Aziridine 24 is then reacted with ROH, $RNH_2$ or RSH to give the corresponding ring opened derivatives 25, 26 and 27, respectively. Aziridine openings of this type are found in Tetrahedron Lett. 1982, 23, 5021 and Angew. Chem. Int. Ed. Engl. 1994, 33, 599.

Scheme 5

Another class of compounds of the invention are prepared by the method of Schemes 5a and 5b. Quinic acid is converted to 28 by the method of Shing, T. K. M.; et al.; Tetrahedron 1991, 47(26), 4571. Mesylation with MsCl in $TEA/CH_2Cl_2$ will give 29 which is reacted with $NaN_3$ in DMF to give 30. Reaction of 30 with TFA in $CH_2Cl_2$ will give 31 which is mesylated with MsCl in $TEA/CH_2Cl_2$ to give 32. Reaction with triphenylphosphine in water will give 33 which is converted to 35 by sequential application of: 1) $CH_3C(O)Cl$ in pyridine, 2) $NaN_3$ in DMP, and 3) NaH in THF. Alkylation of 35 with a wide variety of nucleophiles common in the art will provide a number of compounds such as 36. Methods for elaboration of the compounds such as 36 to other embodiments of the invention will be similar to those described above.

Scheme 5

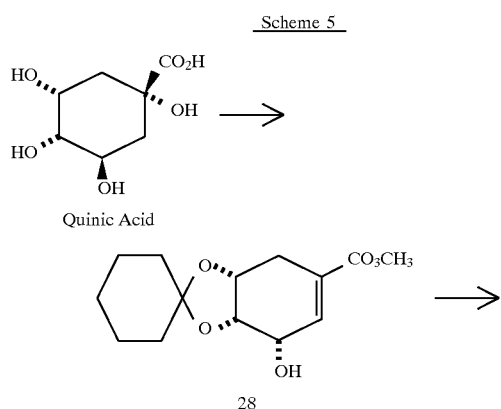

Quinic Acid

28

65
-continued
Scheme 5
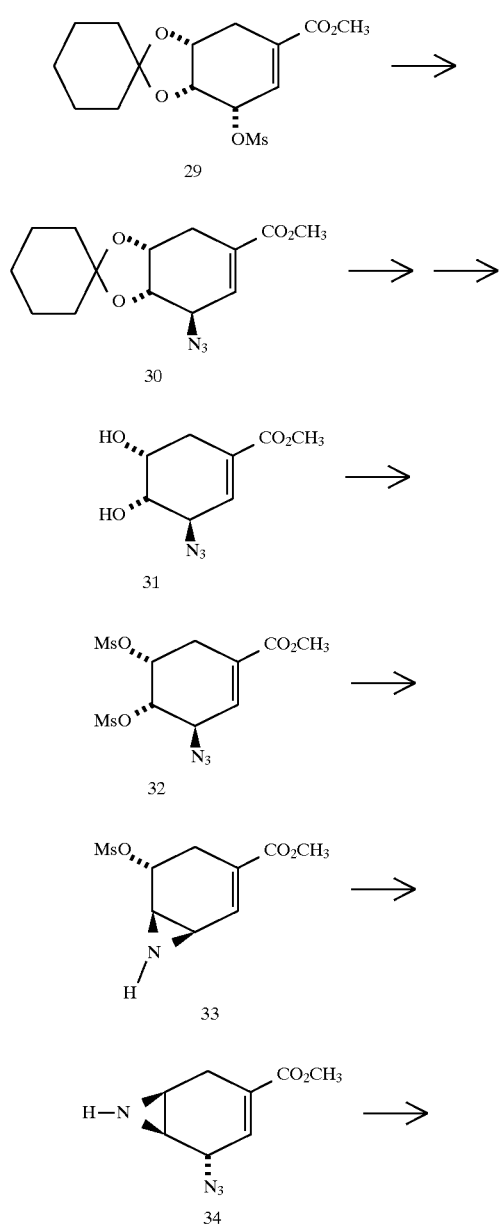
66
-continued
Scheme 5
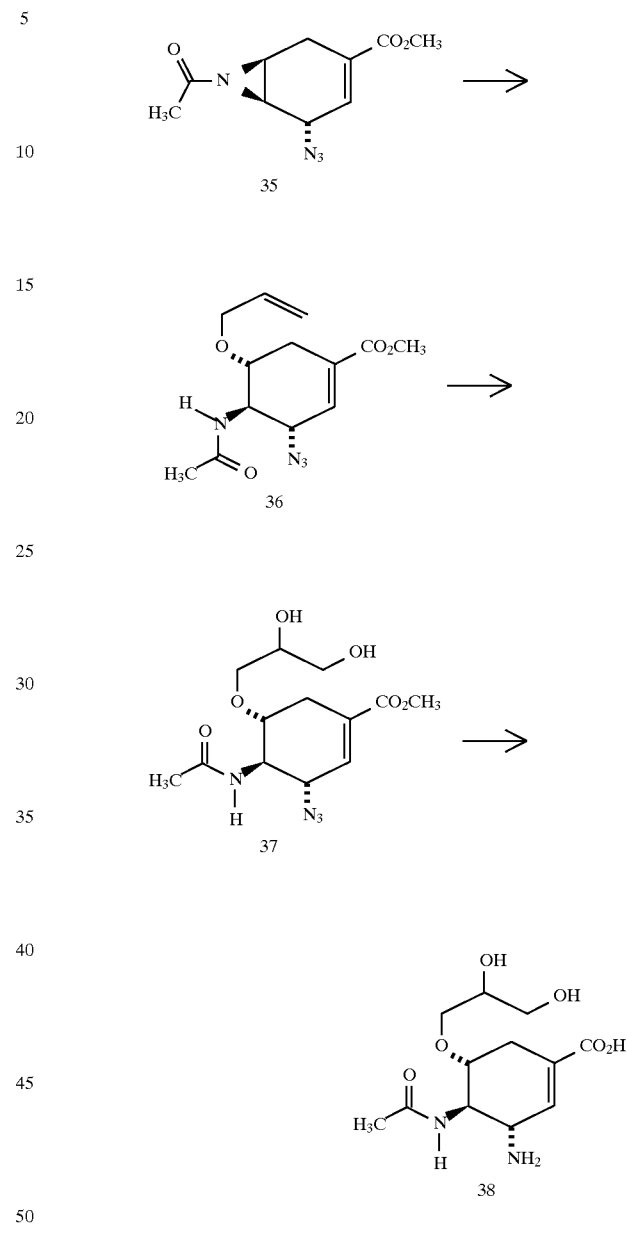

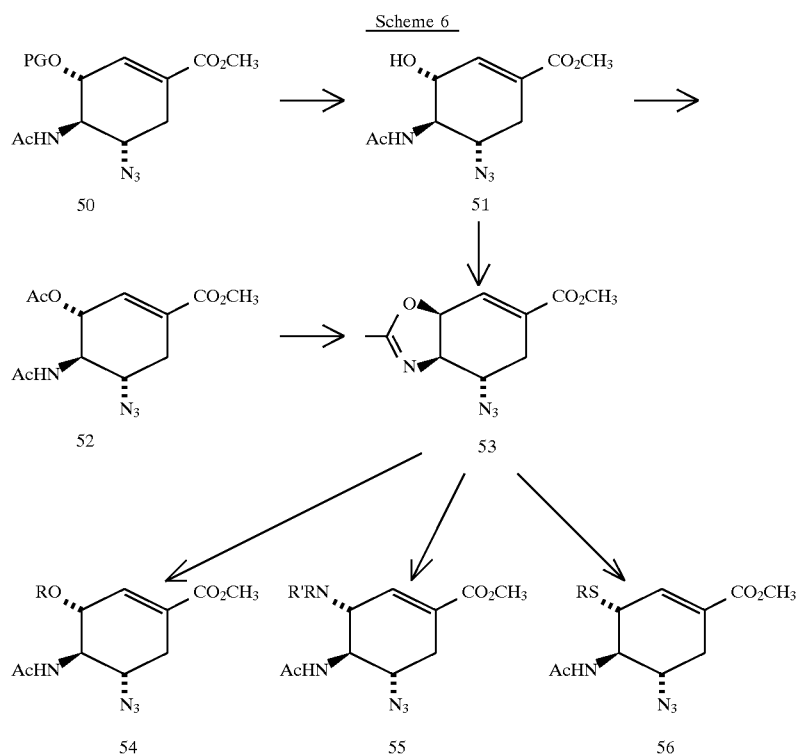

Scheme 6

Another class of compounds of the invention are prepared by the method of Scheme 6. Protected alcohol 50 (PG= methoxymethyl ether) is deprotected under standard conditions described in "Protective Groups in Organic Synthesis" 2nd ed., T. W. Greene and P. G. M. Wuts, John Wiley & Sons, New York, N.Y., 1991. Alcohol 51 is converted to acetate 52 with acetic anhydride and pyridine under standard conditions. Acetate 52 is treated with TMSOTf or $BF_3.OEt$ to afford oxazoline 53. Such transformations are described in *Liebigs Ann. Chem.*, 1991, 129 and *Carbohydrate Research* 1993, 181, respectively. Alternatively, alcohol 51 is transformed to oxazoline 53 by conversion to the corresponding mesylate or tosylate and subsequently cyclized to the oxazoline under standard conditions, as described in *J. Org. Chem.* 1985, 50, 1126 and *J. Chem. Soc.* 1970, 1385. Oxazoline 53 is reacted with ROH, RR'NH, or RSH to provide the corresponding ring opened derivatives 54, 55, and 56 respectively. Such transformations are described in *J. Org. Chem.* 1984, 49, 4889. and *Chem. Rev.* 1971, 71, 483.

Schemes 7–12

Other exemplary methods of preparing the compounds of the invention are shown in Schemes 7–12 below. A detailed description of the methods is found in the Experimental section below.

Scheme 7a

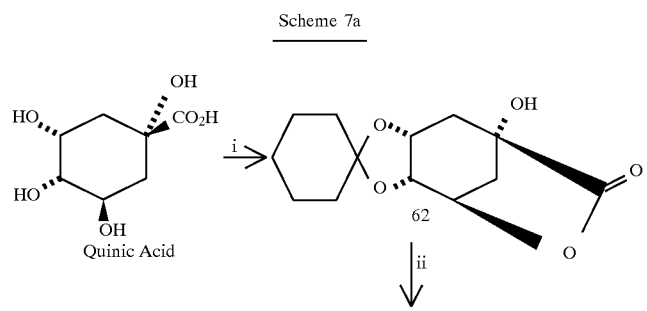

-continued
Scheme 7a
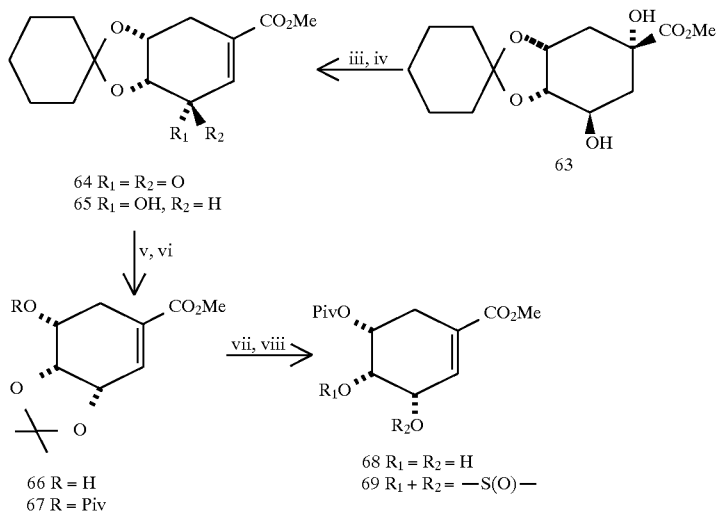
i. cyclohexanone/TsOH/benzene; ii. NaOMe/MeOH; iii. PCC/Molecular sieves 3 A/pyridine;
iv. NaBH₄/MeOH; v. acetone/TsOH; vi. PivCl/pyridine; vii. acetone/H₂O; viii. SOCl₂/Et₃N
Scheme 7b
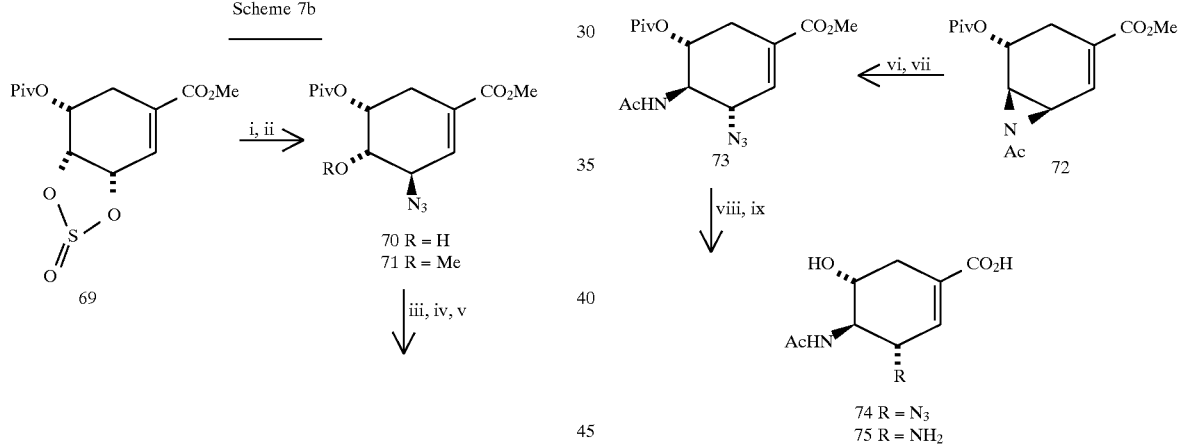
i. NaNa₃/DMF; ii. MsCl/Et₃N; iii. PPh₃/THF; iv. H₂O/Et₃N; v. AcCl/pyridine; vi. NaN₃/NH₄C
vii. Ac₂O; viii. KOH/MeOH/H₂O; ix. H₂/Pd-C(Lindlar)
Scheme 7c
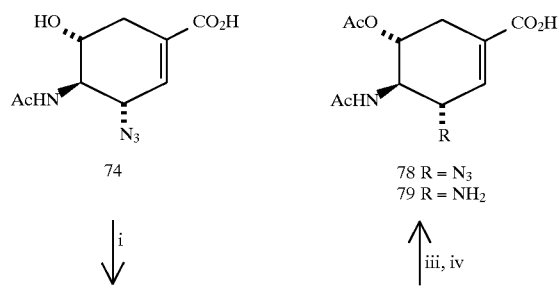

-continued
Scheme 7c
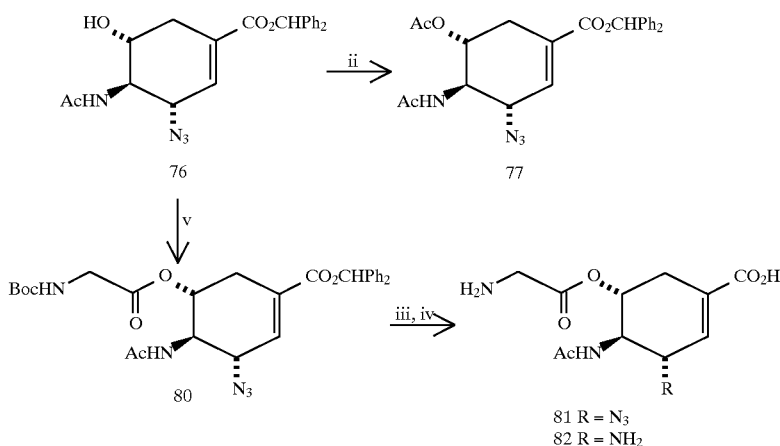
i. Ph₂CN₂/EtOH; ii. Ac₂O/pyridine; iii. TFA/anisole; iv. H₂/Pd-C(lindlar)
v. BocNHCH₂CO₂H/DCC/DMAP;
Scheme 8
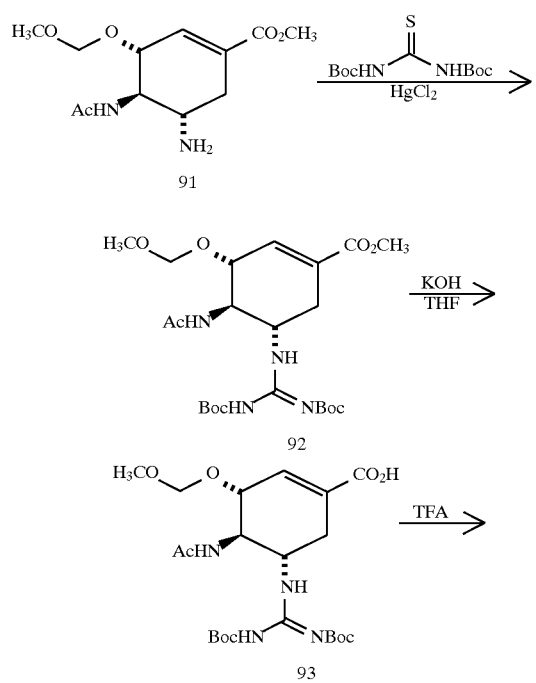
Scheme 9
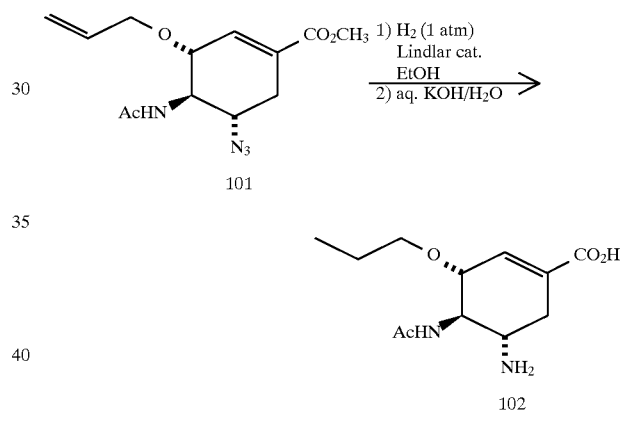
Scheme 10
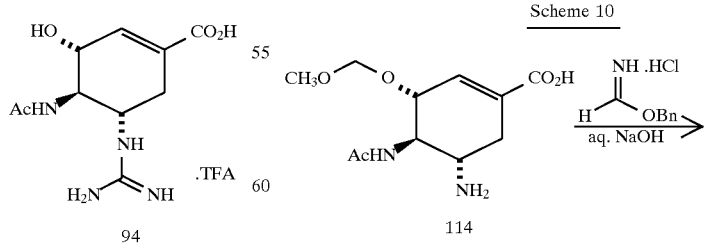

Scheme 10

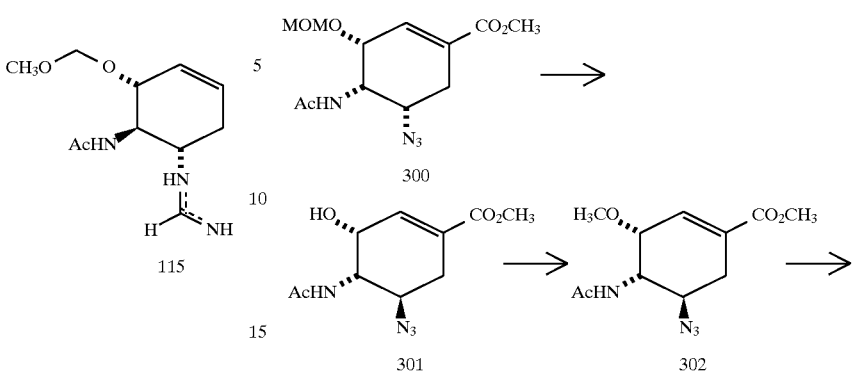

Scheme 11

Scheme 13

Scheme 14

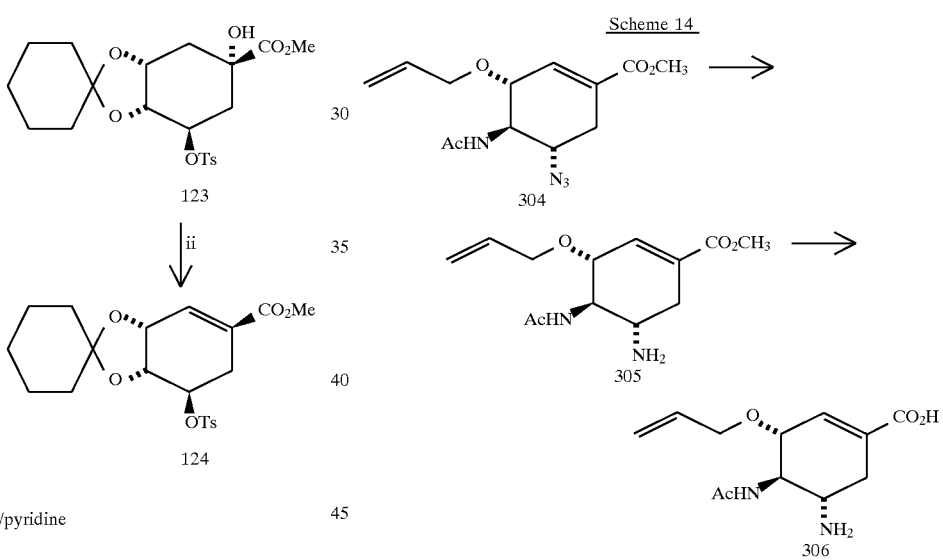

i. TsCl/DMAP/pyridine; ii. POCl₃/pyridine

Scheme 12

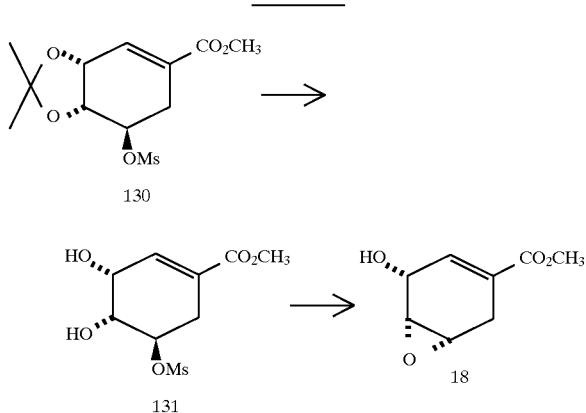

Modification of the exemplary starting materials to form different $E_1$ groups has been described in detail and will not be elaborated here. See Fleet, G. W. J.; et al.; *J. Chem. Soc. Perkin Trans. I*, 1984, 905–908, Fleet, G. W. J.; et al.; *J. Chem. Soc., Chem. Commun.*, 1983, 849–850, Yee, Ying K.; et al.; *J. Med. Chem.* 1990, 33, 2437–2451; Olson, R. E.; et al.; *Bioorganic & Medicinal Chemistry Letters*, 1994, 4(18), 2229–2234, Santella, J. B. III; et al.; *Bioorganic & Medicinal Chemistry Letters*, 1994, 4(18), 2235–2240; Judd, D. B.; et al.; *J. Med. Chem.* 1994, 37, 3108–3120, and Lombaert, S. De; et al.; *Bioorganic & Medicinal Chemistry Letters*, 1994, 5(2), 151–154, each of which is incorporated herein by reference in its entirety.

The $E_1$ sulfur analogs of the carboxylic acid compounds of the invention are prepared by any of the standard techniques. By way of example and not limitation, the carboxylic acids are reduced to the alcohols by standard methods. The alcohols are converted to halides or sulfonic acid esters by standard methods and the resulting compounds are reacted with NaSH to produce the sulfide product. Such reactions are described in Patai, "The Chemistry of the Thiol Group" (John Wiley, New York, 1974), pt. 2, and in particular pages 721–735.

Modifications of each of the above schemes leads to various analogs of the specific exemplary materials produced above. The above cited citations describing suitable methods of organic synthesis are applicable to such modifications.

In each of the above exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

Each of the cited works above is incorporated by reference in its entirety. Specifically cited sections or pages of the above cited works are incorporated by reference with specificity. The invention has been described in detail sufficient to allow one of ordinary skill in the art to make and use the subject matter of the following claims. It is obvious that certain modifications of the methods and compositions of the following claims can be made within the scope and spirit of the invention.

EXAMPLES

General

The following Examples refer to the Schemes.

EXAMPLE 1

Epoxy alcohol 1: Prepared according to the procedure of McGowan and Berchtold, *J. Org. Chem.* 1981, 46, 2381.

EXAMPLE 2

Epoxy allyl ether 2: To a solution of epoxy alcohol 1 (2.37g, 14.08 mmol) in dry benzene (50 mL) was added thallium(I)ethoxide (1.01 mL) in one portion. After 2 hr the reaction was concentrated in vacuo and the residue dissolved in acetonitrile. Allyl iodide (3.0 mL) was added and the mixture was stirred in the dark for 16 h. The solids were filtered thru a celite pad and washed with chloroform. Concentration in vacuo followed by flash chromatography (40% EtOAc in hexane) gave 1.24 g (42%) of 2 as a pale viscous oil.

$^1$H NMR (300 MHz, $CDCl_3$):d 6.75 (1H,m); 6.10–5.90 (1H, m,—CH=,allyl); 5.40–5.15 (2H, m,=$CH_2$, allyl); 4.47–4.43 (1H,m); 4.30–4.15(2H,m, —$CH_2$—,allyl); 3.73 (3H,s); 3.55–3.50 (1H,m);3.45–3.40(1H,m); 3.15–3.00(1H, dm, J=19.5 Hz), 2.50–2.35(1H,dm,J=2.7, 19.5 Hz).

EXAMPLE 3

Azido alcohol 3: Epoxide 2 (1.17 g, 5.57 mmol), sodium azide (1.82 g) and ammonium chloride (658 mg) were refluxed in MeOH/$H_2O$(8:1) (35 mL) for 18 h. The reaction was then concentrated in vacuo and the residue partitioned between ethyl ether and water. The organic layer was washed with brine and dried. Concentration in vacuo gave 3 as a pale oil 1.3 g (92%) which was used without further purification.$^1$H NMR (300 MHz, $CDCl_3$):d 6.95–6.85(1H, m); 6.00–5.85(1H, m,—CH=,allyl); 5.35–5.25(2H, m,=$CH_2$, allyl);4.25–4.10(2H,m,—$CH_2$—,ally); 4.12(1H, bt,J=4.2 Hz); 3.95–3.75(2H,m); 3.77(3H,s); 2.85(1H,dd,J= 5.3,18.3 Hz);2.71(1H,bs);2.26(1H,dd,J=7.2, 18.3 Hz).

EXAMPLE 4

Aziridine 4: To a solution of alcohol 3 (637 mg, 2.52 mmol) in $CH_2Cl_2$ (20 mL) cooled to 0° C. was added DMAP (few crystals) and triethyl amine (442 mL). MsCl (287 mL) was then added and the reaction stirred for 2 h at 0° C. Volatiles were removed and the residue partitioned between ethyl ether and water. The organic layer was washed with satd. bicarbonate, brine and then dried. Concentration in vacuo gave 881 mg of crude mesylate. $^1$H NMR (300 MHz, $CDCl_{13}$):d 6.87–6.84(1H,s); 6.00–5.85(1H, m,—CH=,allyl); 5.40–5.25 (2H,m,=$CH_2$, allyl);4.72(1H, dd,J=3.9,8.5 Hz); 4.32(1H,bt,J=3.9 Hz);4.30–4.15(2H,m,—$CH_2$—,ally);3.77 (3H,s); 3.14 (3H,s); 2.95 (1H,dd,J=5.7, 18.6 Hz); 2.38 (1H,dd,J=6.7, 18.6 Hz).

The crude mesylate was dissolved in dry THF (20 mL) and treated with $Ph_3P$ (727 mg). After stirring for 3 h at room temperature, water (15mL) and solid $NaHCO_3$ (1.35 g) was added and the mixture stirred overnight at room temperature. The reaction was then concentrated in vacuo and the residue partitioned between EtOAc, satd. bicarb. and brine. The organic layer was separated and dried over $MgSO_4$. Concentration in vacuo and flash chromtography of the residue gave the aziridine 4 170 mg (33%) as a pale yellow oil.

$^1$H NMR (300 MHz, $CDCl_3$):d 6.82–6.80(1H,m); 6.04–5.85(1H, m,—CH=,allyl); 5.35–5.20 (2H, m,=$CH_2$, allyl); 4.39 (1H,bd, J=2.4 Hz);4.20–4.05 (2H,m,—$CH_2$, allyl); 3.73 (3H,s);2.90–2.80 (1H,bd, J=18.9 Hz); 2.65–2.40 (2H,m).

EXAMPLE 5

N-acetyl aziridine 5: Aziridine 4 (170 mg, 0.814 mmol) was dissolved in $CH_2Cl_2$ (2 mL) and pyridine (4 mL) and cooled to 0° C. Acetyl chloride (87 mL) was then added and the reaction stirred at 0° C. for 1 h. Volatiles were removed in vacuo and the residue partitioned between ethyl ether, satd. bicarb. and brine. The organic layer was separated and dried over MgSO$_4$. Concentration gave crude 5 196 mg (96%) which was used without further purification.$^1$H NMR (300 MHz, CDCl$_3$):d 6.88–6.86(1H,m); 6.00–5.85(1H, m,—CH=,allyl); 5.40–5.20 (2H, m,=CH$_2$, allyl); 4.45–4.40 (1H,m); 4.16 (2H,d, J=6.0 Hz,—CH$_2$—,allyl); 3.76(3H,s);3.00–2.95(2H,m); 2.65(1H, bd, J=18.5 Hz); 2.14 (3H,s).

EXAMPLE 6

Azido allyl ether 6: Aziridine 5 (219 mg, 0.873 mmol), sodium azide (426 mg) and ammonium chloride (444 mg) in dry DMF (7 mL) was heated at 65° C. under argon overnight. The reaction was poured into satd. bicarb./brine and extracted with ethyl ether several times. The combined ether layers were washed with brine and dried. Concentration followed by flash chromatography (EtOAc only) gave the azido amine 77 mg (35%) which was dissolved in CH$_2$Cl$_2$ (1 mL) and pyridine (1 mL) and cooled to 0° C. Acetyl chloride (38 mL) was added and after 45 min solid NaHCO$_3$ was added and the volatiles removed under vacuum. The residue was partitioned between EtOAc and brine. The organic layer was dried over MgSO$_4$ and concentrated in vacuo. Flash chromatography (EtOAc) only) gave 6 90 mg (99%). $^1$H NMR (500 MHz, CDCl$_3$):d 6.86(1H, bt, J=2.2 Hz); 5.95–5.82 (lH,m,CH=,allyl); 5.68 (1H,bd, J=7.3 Hz); 5.35–5.20 (2H, m,=CH$_2$, allyl); 4.58–4.52 (1H,m); 4.22–4.10 (2H,m); 4.04 (1H, dd, J=5.9, 12.5 Hz);3.77 (3H, s); 3.54–3.52 (1H, m); 2.89 (1H, dd, J=5.9, 17.6 Hz); 2.32–2.22 (1H,m); 2.06 (3H, s).

EXAMPLE 7

Azido diol 7: To a solution of olefin 6 (90 mg, 0.306 mmol) in acetone (3 ml) and water (258 mL) was added N-methyl morpholine-N-oxide (39 mg) and OsO$_4$ (73 mL of a 2.5% w/w in t-butanol). The reaction was then stirred at room temperature for 3 days. Solid sodium hydrosulfite was added and after stirring for 20 min the reaction was filtered thru a celite pad and washed with copious amounts of acetone. Concentration in vacuo followed by flash chromatography (10% MeOH in CH$_2$Cl$_2$) gave the diol 7 50 mg (50%). $^1$H NMR (300 MHz, CD$_3$CN):d 6.80–6.70(1H,m); 4.20–4.15 (1H, bm); 3.95–3.80 (1H,m); 3.80–3.25 (6H, m); 3.70 (3H, s); 3.10 (1H, bs); 2.85 (1H,bs); 2.85–2.75(1H,m); 2.30–2.15 (1H, m); 2.16 (1H, bs); 1.92 (3H, s).

EXAMPLE 8

Amino acid diol 8: A solution of the diol 7 (23 mg, 0.07 mmol) in THF (1 ml) was treated with aq. KOH (223 mL, of 0.40M solution) at room temperature. After stirring for 1.5 h the reaction was acidified to pH=4 with Amberlite IR-120 (plus) ion exchange resin. The resin was filtered and washed with MeOH. Concentration in vacuo gave the crude carboxylic acid which was dissolved in ethanol (1.5 mL). To this solution was added Lindlars catalyst (20 mg) and the reaction stirred over a hydrogen atmosphere (1 atm via a balloon) for 20 h. The reaction mixture was filtered thru a celite pad and washed with hot ethanol and water. The ethanol was removed under vacuum and the resulting aqueous layer lyophilized to give a mixture of the desired amino acid 8 and the starting azide 7 as a white powder.Compound 8:$^1$H NMR (500 MHz, D$_{2O}$):d 6.5 (1H, s); 4.24–4.30 (2H, m); 4.25–4.18 (1H, m); 3.90–3.55 (5H, complex m); 2.96–2.90 (1H, m); 2.58–2.50 (1H, complex m);2.12 (3H,s).

EXAMPLE 9

Compound 62: A suspension of Quinic acid (60 g), cyclohexanone (160 ml) and toluenesulfonic acid (600 mg) in benzene (450 mL) was refluxed with Dean-Stark for 14 hrs. The reaction mixture was cooled to rt. and poured into sat. NaHCO$_3$ solution (150 ml). The aqueous layer was extracted with CH$_2$Cl$_2$ (3×). The combined organic layers were washed with water (2×), brine (1×), and dried over Na$_2$SO$_4$. Concentration gave a whited solid, which was recrystallized from ether (75 g, 95%): $^1$H NMR (CDCl$_3$) d 4.73 (dd, J=6.1, 2.5 Hz, 1 H), 4.47 (ddd, J=7.0,7.0,3.0 Hz, 1H), 4.30 (ddd, J=5.4,2.6, 1.4 Hz, 1 H), 2.96 (s, 1H), 2.66 (d, J=11.7 Hz, 1H), 2.40–2.15 (m, 3 H), 1.72–1.40 (m, 10 H).

EXAMPLE 10

Compound 36: To a solution of lactone 62 (12.7 g, 50 mmol) in methanol (300 ml) was added sodium methoxide (2.7 g, 50 mmol) in one portion. The mixture was stirred at rt. for 3 hrs, and quenched with acetic acid (3 ml) and stirred for 10 min. The mixture was poured into sat. NH$_4$Cl solution (300 ml), and extracted with CH$_2$Cl$_2$ (3×). The combined organic phase was washed with brine (1x), and dried over MgSO$_4$. Purification by flash column chromatography (Hexane/EtOAc=1/1 to 1/2) gave diol (11.5 g, 80%) and starting material (1.2 g, 10%): $^1$H NMR (CDCl$_3$) d 4.47 (ddd, J=7.4, 5.8, 3.5 Hz, 1 H), 4.11 (m, 1 H), 3.98 (m, 1 H), 3.81 (s, 3 H), 3.45 (s, 1 H), 2.47 (d, J=3.3 Hz, 1 H), 2.27 (m, 2 H), 2.10 (dd, J=11.8, 4.3 Hz, 1 H), 1.92–1.26 (m, 10 H).

EXAMPLE 11

Compound 64: To a mixture of diol 63 (1.100 g, 3.9 mmol), molecule sieves (3 A, 2.2 g) and pyridine (1.1 g) in CH$_2$Cl$_2$ (15 ml) was added PCC (3.3 g, 15.6 mmol) in one portion. The mixture was stirred at rt. for 26 hrs, and diluted with ether (30 ml). The suspension was filtered through a pad of celite, and washed with ether (2×20 ml). The combined ether was washed with brine (2×), and dried over MgSO$_4$. Concentration and purification was by flash column chromatography (Hexane/EtOAc=3/1) gave the ketone (0.690 g, 67%): $^1$H NMR (CDCl$_3$) d 6.84 (d, J=2.8 Hz, 1 H), 4.69 (ddd, J=6.4, 4.9, 1.6 Hz, 1 H), 4.30 (d, J=5.0 Hz, 1 H), 3.86 (s, 3 H), 3.45 (d, J=22.3 Hz, 1 H), 2,86 (m, 1 H), 1.69–1.34 (m, 10 H).

EXAMPLE 12

Compound 65: To a solution of ketone 64 (0.630 g, 2.4 mmol) in MeOH (12 ml) at 0° C. was added NaBH4 in 30 min. The mixture was stirred for additional 1.5 hrs at 0° C., and quenched with 15 ml of sat. NH$_4$Cl solution. The solution was extracted with CH$_2$Cl$_2$ (3×), and the combined organic extract was dried over MgSO$_4$. Purification by flash column chromatography (Hexane/EtOAc=2/1) gave the alcohol (0.614 g, 97%): $^1$H NMR (CDCl$_3$) d 6.94 (d, J=0.5 Hz, 1 H), 4.64 (ddd, J=9.8, 6.7, 3.2 Hz, 1 H), 4.55 (dd, J=7.1,4.2 Hz, 1 H), 4.06 (m, 1 H), 3.77 (s, 3 H), 3.04 (dd, J=16.5,2.1 Hz, 1 H), 2.73 (d, J=10.2 Hz, 1 H), 1.94 (m, 1 H), 1.65–1.29 (m, 10 H).

EXAMPLE 13

Compound 66: Alcohol 65 (2.93 g, 10.9 mmol) and toluenesulfonic acid (1.5 g) were dissolved in acetone (75 ml), and the mixture was stirred at rt. for 15 hrs. The reaction was quenched with water (30 ml), and basified with concentrated NH$_3$—H$_2$O until PH=9. Acetone was removed under reduced pressure, and the water phase was extracted with CH$_2$Cl$_2$ (3×). The combined organic extracts were washed with brine (1×), and dried over Na$_2$SO$_4$. Concentration gave the desired product: $^1$H NMR (CDCl$_3$) d 7.01

(m, 1 H), 4.73 (m, 1 H), 4.42 (m, 1 H), 3.97 (m, 1 H), 3.76 (s, 3 H), 2.71–2.27 (m, 2 H), 2.02 (s, 3 H), 1.98 (s, 3 H).

EXAMPLE 14

Compound 67: To a solution of alcohol 66 (10.9 mmol) in $CH_2Cl_2$ (60 ml) at 0° C. was added pyridine (4.4 ml, 54.5 mmol), followed by addition of trimethylacetyl chloride (2.7 ml, 21.8 mmol). The mixture was warmed to rt. and stirred for 14 hrs. The mixture was diluted with $CH_2Cl_2$, and washed with water (2×), brine (1×), and dried over $MgSO_4$. Purification by flash column chromatography (Hexane/EtOAc=9/1) gave the diester (2.320 g, 68%): $^1H$ NMR ($CDCl_3$) d 6.72 (m, 1 H), 5.04 (m, 1 H), 4.76 (m, 1 H), 4.40 (m, 1 H), 3.77 (s, 3 H), 2.72–2.49 (m, 2 H), 1.37 (s, 3 H), 1.35 (s, 3 H), 1.23 (s, 9 H).

EXAMPLE 15

Compound 68: Diester 67 (2.32 g, 2.3 mmol) was dissolved in acetone/H2O (1/1, 100 ml) and heated at 55° C. for 16 hrs. Solvents were removed, water (2×50 ml) was added and evaporated. Concentration with toluene (2×50 ml) gave diol, which was used without further purification: $^1H$ NMR ($CDCl_3$) d 6.83 (m, 1 H), 5.06 (m, 1 H), 4.42 (m, 1 H), 4.09 (m, 1 H), 3.77 (s, 3 H), 2.68–2.41 (m, 2 H), 1.22 (s, 9 H).

EXAMPLE 16

Compound 69: To a solution of diol 68 (0.410 g, 1.5 mmol) in THF (8 ml) at 0° C. was added triethylamine (0.83 ml, 6.0 mmol), followed by slow addition of thionyl chloride (0.33 ml, 4.5 mmol). The mixture was warmed to rt. and stirred for 3 hrs. The mixture was diluted with $CHCl_3$, and washed with water (3×), brine (1×), and dried over $MgSO_4$. Purification by flash column chromatography (Hexanes/EtOAc=5/1) gave a exo/endo mixture (0.430 g, 90%): $^1H$ NMR ($CDCl_3$) d 6.89–6.85 (m, 1 H), 5.48–4.84 (m, 3 H), 3.80, 3.78 (s, 3 H), 2.90–2.60 (m, 2 H), 1.25, 1.19 (s, 9 H).

EXAMPLE 17

Compound 70: The mixture of sulfone 69 (0.400 g, 1.3 mmol) and sodium azide (0.410 g, 6.29 mmol) in DMF (10 ml) was stirred for 20 hrs. The reaction mixture was then diluted with ethyl acetate, washed with sat. $NH_4Cl$ solution, water, brine, and dried over $MgSO_4$. Concentration gave the azide (0.338 g, 90%): $^1H$ NMR ($CDCl_3$) d 6.78 (m, 1 H), 5.32 (m, 1 H), 4.20 (m, 1 H), 3.89 (m, 1 H), 3.78 (s, 3 H), 3.00–2.60 (m, 2 H), 1.21 (s, 9 H).

EXAMPLE 18

Compound 71: To a solution of alcohol 70 (0.338 g, 1.1 mmol) in $CH_2Cl_2$ (11 ml) at 0° C. was added triethylamine (0.4 ml, 2.9 mmol), followed by slow addition of methylsulfonic chloride (0.18 ml, 2.3 mmol). The mixture was stirred at 0° C. for 30 min., and diluted with $CH_2Cl_2$. The organic layer was washed with water (2×), brine, and dried over $MgSO_4$. Purification by flash column chromatography (Hexane/EtOAc=3/1) gave the desired compound (0.380 g, 82%): $^1H$ NMR ($CDCl_3$) d 6.82 (m, 1 H), 5.44 (m, 1 H), 4.76 (dd, J=7.3, 1.4 Hz, 1 H), 4.48 (m, 1 H), 3.80 (s, 3 H), 3.11 (s, 3 H), 2.82–2.61 (m, 2 H), 1.21 (s, 9 H).

EXAMPLE 19

Compound 72: The mixture of azide 71 (0.380 g, 0.94 mmol) and triphenylphosphine (0.271 g, 1.04mmol) in THF (19 ml) was stirred for 2 hrs. The reaction was quenched with water (1.9 ml) and triethylamine (0.39 ml, 2.82 mmol), and the mixture was stirred for 14 hrs. Solvents were removed under reduced pressure, and the mixture was used for next step. To a solution of above mixture in $CH_2Cl_2$ (20 ml) at 0° C. was added pyridine (0.68 ml, 8.4 mmol), followed by slow addition of acetyl chloride (0.30 ml, 4.2 mmol). The mixture was stirred at 0° C. for 5 min., and diluted with ethyl acetate. The mixture was washed with water (2×), brine (1×), dried over $MgSO_4$. Purification by flash column chromatography (Hexanes/EtOAc=3/1) gave the aziridine (0.205 g, 83%): $^1H$ NMR ($CDCl_3$) d 7.19 (m, 1 H), 5.58 (m, 1 H), 3.77 (s, 3 H), 3.14 (m, 2 H), 2.85 (dd, J=7.0, 1.6 Hz, 1 H), 2.34 (m, 1 H), 2.16 (s, 3H), 1.14 (s,9 H).

EXAMPLE 20

Compound 73: The mixture of aziridine 72 (0.200 g, 0.68 mmol), sodium azide (0.221 g, 3.4 mmol), and ammonium chloride (0.146 g, 2.7 mmol) in DMF (10 ml) was stirred at rt. for 14 hrs. Then the mixture was diluted with ethyl acetate, and washed with water (5×), brine (1×), and dried over $MgSO_4$. Purification by flash column chromatography (hexanes/EtOAc=2/1) gave desired product and deacetyl amine (0.139 g). The mixture was dissolved in acetic anhydride (2 ml), and stirred for 2 hrs. Excess anhydride was removed under reduced pressure, and give the desired product (149 mg): $^1H$ NMR ($CDCl_3$) d 6.76 (m, 1 H), 5.53 (d, J=8.5 Hz, 1 H), 5.05 (m, 1 H), 4.31 (m, 1 H), 4.08 (m, 1 H), 3.79 (s, 3 H), 2.91 (m, 1 H), 2.51 (m, 1 H), 1.99 (s, 3 H), 1.20 (s, 9 H).

EXAMPLE 21

Compound 74: A solution of potassium hydroxide in $MeOH/H_2O$ (0.5 M, 4.4 ml, 2.2 mmol) was added to ester 73 (149 mg, 0.44 mmol) and the mixture was stirred at rt. for 3 hrs. The mixture was cooled to 0° C., and acidified with Amberlite (acidic) to PH=3–4. The mixture was filtered, and washed with MeOH. Concentration gave the carboxylic acid as a white solid (73 mg, 69%): $^1H$ NMR ($CD_3OD$) d 6.62 (m, 1 H), 4.15 (m, 1 H), 3.95–3.72 (m, 2 H), 2.84 (dd, J=6.7, 1.4 Hz, 1 H), 2.23 (m, 1 H), 1.99 (s, 3 H).

EXAMPLE 22

Compound 75: The mixture of azide 74 (8 mg) and Pd-C (Lindlar) (15 mg) in ethanol (2 ml) was stirred under hydrogen for 16 hrs. The mixture was filtered through celite, washed with hot $MeOH-H_2O$ (1/1). Concentration gave a solid. The solid was dissolved in water, and passed through a short C-8 column, and washed with water. Concentration gave a white solid (6 mg): $^1H$ NMR ($D_2O$) d 6.28 (m, 1 H), 4.06–3.85 (m, 3 H), 2.83 (dd, J=17.7,5.4 Hz, 1 H), 2.35 (m, 1 H), 2.06 (s, 3 H).

EXAMPLE 23

Compound 76: Carboxylic acid 74 (68 mg, 0.28 mmol) and diphenyldiazomethane (61 mg, 0.31 mmol) were dissolved in ethanol (12 ml), and stirred for 16 hrs. The reaction was quenched with acetic acid (0.5 ml), and the mixture was stirred for 10 min. Solvents were removed under reduced pressure. Purification by flash column chromatography (EtOAc) gave the ester (56 mg, 50%): $^1H$ NMR ($CD_3OD$) d 7.36–7.23 (m, 10 H), 6.88 (s, 1 H), 6.76 (s, 1 H), 4.21 (m, 1 H), 3.93–3.79 (m, 2 H), 2.89 (dd, J=17.7, 5.0 Hz, 1 H), 2.34 (m, 1 H), 2.00 (s, 3 H).

EXAMPLE 24

Compound 77: To a solution of alcohol 76 (20 mg, 0.05 mmol) in $CH_2Cl_2$ (1 ml) was added pyridine (40 ul, 0.5 mmol), followed by addition of acetic anhydride (24 ul, 0.25 mmol). The mixture was stirred for 24 hrs, and solvents and reagents were removed under reduced pressure. Purification by flash column chromatography (Hexane/EtOAc=1/2) gave the diester (20 mg, 91%): $^1$H NMR (CDCl$_3$) d 7.40–7.27 (m, 10 H), 6.95 (s, 1 H), 6.87 (m, 1 H), 5.60 (m, 1 H), 5.12 (ddd, J=16.4, 10.2, 5.9 Hz, 1 H), 4.28 (dd, J=20.0, 9.4 Hz, 1 H), 4.15 (m, 1 H), 2.93 (dd, J=17.8, 5.2 Hz, 1 H), 2.57 (m, 1 H), 2.09 (s, 3 H), 2.01 (s, 3 H).

EXAMPLE 25

Compound 78: The mixture of diester 77 (20 mg, 0.045 mmol), anisole (50 ul, 0.45 mmol), and TFA (1 ml) in CH$_2$Cl$_2$ (1 ml) was stirred for 20 min. Solvents and reagents were removed under reduced pressure. Purification by flash column chromatography (EtOAc to EtOAc/AcOH=100/1) gave the carboxylic acid (6 mg): $^1$H NMR (CDCl$_3$) d 6.85 (m, 1 H), 5.54 (m, 1 H), 5.12 (m, 1 H), 4.31–4.03 (m, 2 H), 2.89 (m, 1 H), 2.60–2.41 (m, 1 H), 2.11 (s, 3 H), 2.03 (s, 3 H).

EXAMPLE 26

Compound 79: The mixture of azide 78 (6 mg, 0.02 mmol) and Pd-C (lindlar) (15 mg) in EtOH/H$_2$O (2.2 ml, 10/1) was stirred under hydrogen for 3 hrs. The mixture was filtered through a pad of celite, washed with hot MeOH/H$_2$O (1/1). Evaporation gave a white solid. The solid was dissolved in water, and passed through a C-8 column. Evaporation of water gave a white powder (3 mg): $^1$H NMR (D$_2$O) d 6.32 (m, 1 H), 5.06 (m, 1 H), 4.06 (t, J=10.4 Hz, 1 H), 3.84 (m, 1 H), 2.83 (m, 1 H), 2.42 (m, 1 H), 2.06 (s, 3 H), 2.00 (s, 3 H).

EXAMPLE 27

Compound 80: To a solution of alcohol 76 (35 mg, 0.086 mmol), Boc-glycine (30 mg, 0.172 mmol), and catalytic amount DMAP in CH$_2$Cl$_2$ (1 ml) was added DCC (35 mg, 0.172 mmol). The mixture was stirred for 30 min, and filtered and washed with CHCl$_3$. The CHCl$_3$ solution was washed with water (2x). Concentration gave a white solid. Purification by flash column chromatography (Hexane/EtOAc=1/2) gave product (30 mg): $^1$H NMR (CDCl$_3$) d 7.39–7.26 (m, 10 H), 6.95 (s, 1 H), 6.86 (m, 1 H), 5.77 (m, 1 H), 5.27 (m, 1 H), 4.99 (m, 1 H), 4.18–4.01 (m, 2 H), 3.94–3.84 (m, 2 H), 2.96 (dd, J=7.8, 5.9 Hz, 1H), 2.57 (m, 1 H), 2.02 (s, 3 H), 1.45 (s, 9 H).

EXAMPLE 28

Compound 81: The mixture of diester 80 (30 mg, 0.05 mmol), anisole (150 ul), and TFA (1 ml) in CH$_2$Cl$_2$ (1 ml) was stirred for 3 hrs. Solvents and reagents were evaporated. The mixture was dissolved in water, and washed with CHCl$_3$ (3x). Water phase was evaporated to gave a white solid (15 mg): $^1$H NMR (CD$_3$OD) d 6.73 (m, 1 H), 5.25–5.15 (m, 1 H), 4.35 (m, 1 H), 4.17 (m, 1H), 3.82 (m, 2 H), 2.93 (dd, J=17.7, 5.6 Hz, 1 H), 2.42 (m, 1 H), 1.97 (s, 3 H).

EXAMPLE 29

Compound 72: The mixture of azide 71 (15 mg, 0.05 mmol) and Pd-C (Lindlar) (30 mg) in EtOH/H$_2$O (4 ml, 1/1)was stirred under hydrogen for 3 hrs. The mixture was filtered through a pad of celite, and washed with hot MeOH/H$_2$O (1/1). Concentration gave a glass-like solid. The solid was dissolved in water, and passed through C-8 column. Evaporation of water gave the amino acid: $^1$H NMR (D$_2$O) d 6.68 (m, 1 H), 5.28 (m, 1 H), 4.29 (m, 1H), 4.08–3.79 (m, 3 H), 2.85 (m, 1 H), 2.41 (m, 1 H), 2.04 (s, 3 H).

EXAMPLE 30 bis-Boc guanidinyl methyl ester 92: Treated according to the procedure of Kim and Qian, *Tetrahedron Lett.* 1993, 34, 7677. To a solution of amine 91 (42 mg, 0.154 mmol), bis-Boc thiourea (43 mg, 0.155 mmol) and triethylamine (72mL) in dry DMF (310 mL) cooled to 0° C. was added mercury chloride (46 mg, 0.170 mmol) in one portion. After 30 min the reaction was warmed to room temperature and stirred for an additional 2.5 h. The reaction mixture was then filtered through a celite pad, concentrated and purified by flash column chromatography (100% ethyl acetate) to give 70 mg (89%) of 92 as a colorless foam. $^1$H NMR (CDCl$_3$, 300 MHz):d 11.37(s, 1H); 8.60(d, 1H, J=7.8 Hz); 6.83(t, 1H, J=2.1 Hz); 6.63(d, 1H, J=8.4 Hz); 4.76(d, 1H, J=7.0 Hz); 4.71(d, 1H, J=7.0 Hz); 4.45–4.10(complex m, 2H); 3.76(s, 3H); 3.39(s, 3H); 2.84(dd, 1H, J=5.4, 17.4 Hz); 2.45–2.30 (m, 1H); 1.92(s, 3H); 1.49(s, 18H).

EXAMPLE 31 bis-Boc guanidinyl carboxylic acid 93: To a solution of ester 92 (70 mg, 0.136 mmol) in THF (3 ml) cooled to 0° C. was added aq. KOH (350 mL of a 0.476M solution). The reaction was then warmed to room temperature and stirred for 2 h. The reaction was then acidified to pH=4.5 with Amberlite IR-120 (plus) acidic resin. The resin was then filtered and washed with ethanol and H$_2$O. Concentration in vacuo gave 66 mg (97%) of carboxylic acid 93 as a white solid. $^1$H NMR (CDCl$_3$, 300 MHz):d 11.40(br s, 1H); 8.67(d, 1H, J=7.8 Hz); 6.89(s, 1H); 6.69(br d, 1H, J=8.4 Hz); 4.77(d, 1H, J=7.2 Hz); 4.70(d, 1H, J=7.2 Hz); 4.40–4.15(m, 2H); 3.39(s, 3H); 2.84(dd, 1H, J=4.8, 17.1 Hz); 2.45–2.30 (m, 1H); 1.95(s, 3H); 1.49(s, 9H); 1.48(s, 9H).

EXAMPLE 32

Guanidine carboxylic acid TFA salt 94: To a solution of bis-Boc guanidinyl carboxylic acid 93 (23 mg, 0.046 mmol) in CH$_2$Cl$_2$ (1 mL) cooled to 0° C. was added neat trifluoroacetic acid (500 mL). After 30 min the reaction was warmed to room temperature and stirred for an additional 1.25 h. Volatiles were removed under vacuum and the residue co-evaporated with several portions of H$_2$O to give a pale orange solid. The residue was purified by reverse phase C$_{18}$ chromatography using H$_2$O as an eluent. Fractions containing the desired product were pooled and lyophilized to give 15 mg of 93 as a white powder.$^1$H NMR (D$_2$O, 500 MHz):d 6.82(t, 1H, J=2.0 Hz); 4.51–4.47(m, 1H); 3.93(dd, 1H, J=9.0, 11.2 Hz); 3.87–3.80 (apparent ddd, 1H); 2.88(m, 1H); 2.48–2.45(complex m); 2.07(s, 3H). $^{13}$C NMR (D$_2$O):d 176.1; 170.0; 157.1; 139.2; 129.5; 69.4; 56.2; 50.9; 30.3; 22.2.

EXAMPLE 33

Synthesis of 102: A solution of azido allyl ether 101 (24 mg, 0.082 mmol) in ethanol (1 ml) was treated with hydrogen gas (1 atm) over Lindlars catalyst (30 mg) for 1.5 h. The reaction mixture was filtered through a celite pad and washed with hot ethanol. Concentration in vacuo gave a pale solid which was dissolved in THF (1.5 ml) and treated with aqueous KOH (246 ml of a 0.50M solution). After stirring at ambient temperature for 2 h the reaction was acidified to pH=4.0 with Amberlite IR-120 (plus) acidic resin, filtered and washed with ethanol and H$_2$O. Concentration in vacuo gave an orange solid which was purified by a $C_{18}$ column chromatography eluting with $H_2O$. Fractions containing the product were pooled and lyophilized to give a 2 to 1 mixture of 102 and the fully saturated compound 103 as a white powder. $^1$H NMR data for compound 102: $^1$H NMR ($D_2O$, 500 MHz):d: 7.85 (s, 1H);4.29 (br d, 1H, J=9.2 Hz); 4.16 (dd, 1H, J=11.6, 11.6 Hz); 3.78–3.72 (m, 2H); 3.62 (apparent ddd, 1H); 2.95 (apparent dd, 1H); 2.58–2.52 (m, 1H); 2.11 (s, 3H); 1.58 (q, 2H, J=7.3 Hz); 0.91 (t, 3H, J=7.3 Hz).

EXAMPLE 34

Synthesis of 115: A solution of amino acid 114 (10.7 mg, 0.038 mmol) in water (1.3 ml) cooled to 0° C. was adjusted to pH=9.0 with 1.0M NaOH. Benzyl formimidate hydrochloride (26 mg, 0.153 mmol) was then added in one portion and the reaction stirred between 0°–5° C. for 3 h while maintaining the pH between 8.5–9.0 with 1.0M NaOH. The reaction was then concentrated in vacuo and the residue applied to a $C_{18}$ column and eluted with water. Fractions containing the product were pooled and lyophilized to give the formamidine carboxylic acid 115 (10 mg) as a white powder. $^1$H NMR ($D_2O$, 300 MHz, mixture isomers): d 7.83 (s, 1H); [6.46(s) & 6.43 (s); 1 H total]; 4.83 (d, 1H, J=7.3 Hz); 4.73 (d, 1H, J=7.3 Hz); 4.50–4.35 (m, 1H); 4.10–4.05 (m, 1H); [4.03–3.95 (m) & 3.80–3.65 (m), 1 H total]; 3.39 (s, 3H); 2.90–2.75 (m, 1H); 2.55–2.30 (m, 1H); [2.03 (s) & 2.01 (s), 3H total].

EXAMPLE 35

Compound 123: To a solution of alcohol 63 (5.842 g, 20.5 mmol) and DMAP (200 mg) in pyridine (40 ml) was added tosyl chloride (4.3 g, 22.6 mmol). The mixture was stirred at rt for 40 hrs, and pyridine was removed under reduced pressure. The reaction was quenched with water, and extracted with EtOAc (3×). The combined organic extracts were washed with water, brine, and dried over $MgSO_4$. Purification by flash column chromatography (Hexanes/EtOAc=2/1) gave the tosylate (8.04 g, 89%): $^1$H NMR ($CDCl_3$) d 7.84 (d, J=8.3 Hz, 2H), 7.33 (d, J=8.1 Hz, 2 H), 4.78 (m, 1 H), 4.43 (m, 1 H), 4.06 (m, 1 H), 3.79 (s, 3 H), 2.44 (s, 3 H), 2.43–1.92 (m, 4 H),1.61–1.22 (m, 10 H).

EXAMPLE 36

Compound 124: To a solution of alcohol 123 (440 mg, 1.0 mmol) in pyridine (3 ml) was added $POCL_{13}$ (100 ul, 1.1 mmol). The mixture was stirred at rt for 12 hrs, and quenched with sat. $NH_4Cl$ solution. The water phase was extracted with ether (3×). The combined ether layers were washed with water (2×), 2N HCl solution (2×), brine, and dried over $MgSO_4$. Purification by flash column chromatography (Hexane/EtOAc=2/1) gave a mixture of the desired product 124 and some inpurity (350 mg, 83%, 2/1).

EXAMPLE 37

Compound 18: To a solution of the known acetonide of methyl shikimate (877 mg, 3.85 mmol, Tetrahedron Lett. 1985, 26, 21.) in dichloromethane (15 mL) at −10° C. was added methanesulfonyl chloride (330 µL, 4.23 mmol) followed by the dropwise addition of triethylamine (640 µL, 4.62 mmol). The solution was stirred at −10° C. for 1 h then at 0° C. for 2 h, at which time methanesulfonyl chloride (30 µL), triethylamine (64 µL) was added. After 1 h cold water was added, the organic phase was separated, washed with water, dried ($MgSO_4$), and evaporated. The crude product was chromatographed on silica gel (1/1-hexane/ethyl acetate) to provide mesylate 130 (1.1 g, 93%) as an oil. Mesylate 130 (990 mg, 3.2 mmol) was dissolved in tetrahydrofuran (5 mL) and was treated with 1M HCl (5 mL). The solution was stirred at rt for 19 h, diluted with water (5 mL) and stirred an additional 7 h. Evaporation of the organic solvent precipitated an oily residue which was extracted into ethyl acetate. The combined organic extracts were washed with brine, dried ($MgSO_4$), and evaporated. Addition of $CH_2Cl_2$ to the crude residue precipitated a white solid which was filtered and washed with $CH_2Cl_2$ to afford diol 131 (323 mg, 38%). To a partial suspension of diol 131 (260 mg, 0.98 mmol) in THF (5 mL) at 0° C. was added DBU (154 µL, 1.03 mmol). The solution was stirred at 0° C. for 3 h and then was warmed to rt stirring for 5 h. The solvent was evaporated and the crude residue was partitioned between ethyl acetate (40 mL) and 5% citric acid (20 mL). The organic phase was washed with brine. Aqueous phases were back extracted with ethyl acetate (15 mL) and the combined organic extracts were dried ($MgSO_4$) and evaporated to afford the epoxide (117 mg, 70%) as a white solid which gave an $^1$H NMR spectrum consistent with structure 18 prepared by literature method.

EXAMPLE 38

Alcohol 301: To a solution of protected alcohol (MOM= methoxymethyl) 300 (342 mg, 1.15 mmol) in $CH_2Cl_2$ (10 mL) at 0° C. was added trifluoroacetic acid (8 mL). After 5 min at 0° C., the solution was stirred 1 h at rt and was evaporated. The crude product was purified on silica gel (ethyl acetate) to afford alcohol 301 (237 mg, 82%) as an oil: $^1$H NMR (300 MHz, $CDCl_3$) d 2.11 (s, 3H), 2.45 (m, 1H), 2.97 (dd, 1H, J=3.8, 18.8), 3.66 (m, 2H), 3.78 (s, 3H), 4.40 (br s, 1H), 5.22 (br s, 1H), 6.19 (br s, 1H), 6.82 (m, 1H).

EXAMPLE 39

Methyl ether 302: To a solution of alcohol 301 (46 mg, 0.18 mmol) and methyl iodide (56 mL, 0.90 mmol) in THF (0.7 mL) at 0° C. was added NaH as a 60% mineral oil dispersion (8 mg, 0.20 mmol). The solution was stirred at 0° C. for 2.5 h, and a second portion of NaH (2 mg) was added. After an additional 1 h at 0° C. and 4 h at rt the solution was cooled to 0° C. and 5% citric acid (0.5 mL) was added. The mixture was extracted with ethyl acetate (4×2 mL) and the combined organic extracts were dried ($MgSO_4$), and evaporated. Purification of the crude residue on silica gel (ethyl acetate) gave methyl ether 302 (12 mg, 25%) as a solid: $^1$H NMR (300 MHz, $CDCl_3$) d 2.07 (s, 3H), 2.23–2.34 (m, 1H), 2.89 (app ddd, 1H), 3.43 (s, 3H), 3.58 (m, 1H), 3.78 (s, 3H), 4.13 (m, 1H), 4.40 (m, 1H), 5.73 (d, 1H, J=7.6), 6.89 (m, 1H).

EXAMPLE 40

Amino acid 303: To a solution of methyl ether 302 (12 mg, 0.45 mmol) in THF(1 mL)/water (100 mL) was added polymer support $Ph_3P$ (75 mg, 3 mmol P/g resin). The mixture was stirred at rt for 19 h. The resin was filtered, washed several times with THF and the combined filtrate and washings were evaporated to provide 8 mg of a crude residue. The residue was dissolved in THF (0.5 mL), and 0.5M KOH (132 mL)/water (250 mL) was added. The solution was stirred at rt for 1.25 h and the pH was adjusted to 3–4 with IR120 ion exchange resin. The resin was filtered and was stirred with 1M HCl. After filtration, the resin was subjected to the same treatment with 1M HCl until the acidic washes no longer tested positive for amine with ninhydrin. The combined resin washings were evaporated and the residue was purified on C-18 reverse phase silica eluting with water to afford after lyophilization, amino acid 303 (1.8 mg, 15%) as a white solid: $^1$H NMR (300 MHz, D$_2$O) d 2.09 (s, 3H), 2.48–2.59 (app qt, 1H), 2.94 (dd, 1H, J=5.7, 17.4), 3.61 (m, 1H), 4.14–4.26 (m, 2H), 6.86 (br s, 1H).

EXAMPLE 41

Amino acid allyl ether 306: To a solution of azide 304(16 mg, 0.054 mmol) in THF (0.50 mL) and H$_2$O (35 mL) was added polystyrene supported PPh$_3$ (50 mg). The reaction was stirred at ambient temperature for 24 h, filtered through a sintered glass funnel and washed with hot methanol. Concentration in vacuo gave the crude amino ester which was dissolved in THF (1.0 mL) and treated with aqueous KOH (220 mL of a 0.5M solution). After stirring at ambient temperature for 2 h Amberlite IR-120 (plus) acidic resin was added until the solution attained pH=4.5. The resin was filtered and washed with ethanol and H$_2$O. Concentration in vacuo gave a pale orange solid which was purified by reverse phase C$_{18}$ chromatography using H$_2$O as an eluent. Fractions containing the desired product were pooled and lyophilized to give the amino acid as a white powder.$^1$H NMR (D$_2$O, 300 MHz):d 6.51(br t, 1H); 6.05–5.80 (m, 1H, —CH=, allyl); 5.36–5.24(m, 2H, =CH$_2$, allyl); 4.35–4.25 (m, 1H); 4.25–4.05 (m, 2H, —CH$_2$—, allyl); 4.02–3.95 (m, 1H); 3.81–3.70 (m, 1H); 2.86–2.77(apparent dd, 1H); 2.35–2.24(complex m, 1H); 2.09(s, 3H).

EXAMPLE 42

Enzyme Inhibition: Using the methods of screening in vitro activity described above, the following activities were observed (+10–100 μm, ++1–10 μm, +++<1.0 μm):

| Compound | IC$_{50}$ |
|---|---|
| 102/103 (2:1) | +++ |
| 8 | ++ |
| A.17.a.4.i | ++ |
| 114 | ++ |
| A.1.a.4.i | ++ |
| 79 | + |
| 82/75 (1.2:1) | + |
| 94 | +++ |

What is claimed is:

1. A composition comprising a compound of formula (I) or (II):

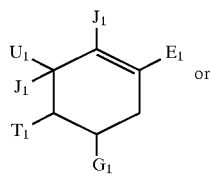

(I)

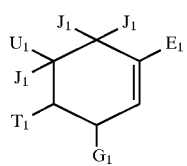

(II)

E$_1$ is —(CR$_1$R$_1$)$_{m1}$W$_1$;

G$_1$ is N$_3$, —CN, —OH, —OR$_{6a}$, —NO$_2$, or —(CR$_1$R$_1$)$_{m1}$W$_2$;

T$_1$ is —NR$_1$W$_3$, a heterocycle, or is taken together with U$_1$ or G$_1$ to form a group having the structure

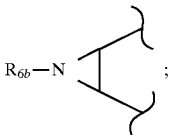

U$_1$ is H or —X$_1$W$_6$;

Each J$_1$ is independently H, F or Cl;

R$_1$ is H or alkyl of 1 to 6 carbon atoms;

R$_2$ is R$_3$ or R$_4$ wherein each R$_4$ is independently substituted with 0 to 3 R$_3$ groups;

R$_3$ is F, Cl, Br, I, —CN, N$_3$, —OR$_{6a}$, —OR$_1$, —N(R$_1$)$_2$, —N(R$_1$)(R$_{6b}$), —N(R$_{6b}$)$_2$, —SR$_1$, —SR$_{6a}$, —C(O)OR$_1$, —C(O)OR$_{6a}$, —OC(O)R$_1$, —NR$_1$C(O)R$_1$, —N(R$_{6b}$)C(O)R$_1$, —C(O)N(R$_1$)$_2$, —C(O)N(R$_{6b}$)(R$_1$), —C(O)N(R$_{6b}$)$_2$, —C(NR$_1$)(N(R$_1$)$_2$), —C(N(R$_{6b}$))(N(R$_{6b}$)$_2$), =O, =S, =N(R$_{6b}$) or =N(R$_1$);

R$_4$ is alkyl of 1 to 6 carbon atoms, alkenyl of 2 to 6 carbon atoms, or alkynyl of 2 to 6 carbon atoms;

R$_5$ is R$_4$ wherein each R$_4$ is substituted with 0 to 3 R$_3$ groups;

R$_{6a}$ is H or a protecting group for hydroxyl or thio;

R$_{6b}$ is H or a protecting group for amino;

W$_1$ is a group comprising an acidic hydrogen or an R$_{6a}$-protected acidic group;

W$_2$ is a group comprising a basic heteroatom or an R$_{6b}$-protected basic heteroatom;

W$_3$ is W$_4$ or W$_5$;

W$_4$ is R$_5$ or —C(O)R$_5$, —C(O)W$_5$, —SO$_2$R$_5$, or —SO$_2$W$_5$;

W$_5$ is carbocycle or heterocycle wherein each W$_5$ is independently substituted with 0 to 3 R$_2$ groups;

W$_6$ is R$_1$, W$_5$, —C(O)OR$_{6a}$, —C(O)NR$_{6b}$R$_{6b}$, —C(NR$_{6b}$)NR$_{6b}$R$_{6b}$, —C(S)NR$_{6b}$R$_{6b}$, —C(O)R$_1$, —CHR$_1$W$_7$, —CH(R$_1$)$_a$W$_7$ or —C(O)W$_7$, where a is 0 or 1, but is 0 when W$_7$ is divalent;

W$_7$ is R$_3$ or an alkyl of 1 to 4 carbons substituted with 1 to 3 R$_3$ groups;

X$_1$ is a bond, —CR$_1$R$_1$—, —(CR$_1$R$_1$)$_2$—, —O—, —NR$_1$—, —N(OR$_1$)—, —N(NR$_1$R$_1$)—, —S—, —SO—, or —SO$_2$—; and each m$_1$ is independently an integer from 0 to 2; with the proviso that when:

(a) E$_1$ is —CO$_2$H, —P(O)(OH)$_2$, —NO$_2$, —SO$_2$H, —SO$_3$H, tetrazolyl, —CH$_2$CHO, —CHO, or —CH(CHO)$_2$;

(b) G$_1$ is —CN, —NHR$_{20}$, —OR$_{20}$, guanidino, —N(R$_{20}$)(OR$_{20}$), —N(H)(R$_{20}$)N(R$_{20}$)$_2$, unsubstituted pyrimidinyl, or unsubstituted (pyrimidinyl) methyl; and (c) T$_1$ is —NHR$_{20}$, —SR$_{20}$, —OR$_{20}$, —CO$_2$R$_{20}$, —NO$_2$, —C(R$_{20}$)$_3$, —CH$_2$CO$_2$R$_{20}$, —CH$_2$NO$_2$, or —CH$_2$NHR$_{20}$; and R$_{20}$ is H; an acyl group having 1 to 4 carbon atoms; a linear or cyclic alkyl group having 1 to 6 carbon atoms, or a halogen-substituted analogue thereof; an allyl group or an unsubstituted aryl group or an aryl substituted by a halogen, an OH group, an NO$_2$ group, an NH$_2$ group or a COOH group;

(d) each J$_1$ is H; and (e) X$_1$ is a bond, —CH$_2$—or —CH$_2$CH$_2$—;

then W$_6$ is not H, W$_7$ or —CH$_2$W$_7$ wherein W$_7$ is H, —OR$_{6a}$, —OR$_1$, —N(R$_1$)$_2$, —N(R$_1$)(R$_{6b}$), —N(R$_{6b}$)

$_2$, —SR$_1$, or —SR$_{6a}$; and the salts, solvates, resolved enantiomers and purified diastereomers thereof.

2. The composition of claim 1 wherein W$_1$ is —CO$_2$R$_1$, —SO$_3$R$_1$, —S(O)OR$_1$, —P(O)(OR$_1$)$_2$, —C(O)—NH—SO$_2$—R$_4$, —SO$_2$—NH—C(O)—R$_4$ or tetrazolyl.

3. The composition of claim 1 wherein E$_1$ is selected from the group consisting of:

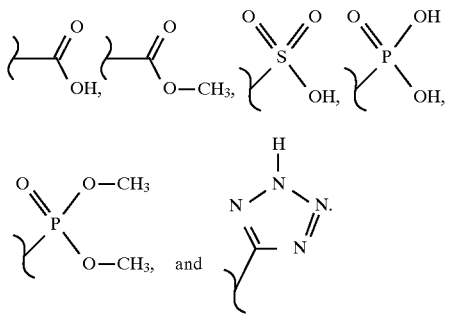

4. The composition of claim 1 wherein W$_2$ is amino, amidino, guanidino, heterocycle or an alkyl of 2 to 3 carbon atoms substituted with an amino and a second group selected from the group consisting of hydroxy and amino.

5. The composition of claim 1 wherein W$_2$ is —NHR$_1$, —C(NH)(NH$_2$), —NR$_1$—C(NR$_1$)(NR$_1$R$_3$), —NH—C(NH)(NHR$_3$), —NH—C(NH)(NHR$_1$), —NH—C(NH)NH$_2$, —CH(CH$_2$NHR$_1$)(CH$_2$OH), —CH(CH$_2$NHR$_1$)(CH$_2$NHR$_1$), —CH(NHR$_1$)—(CR$_1$R$_1$)$_{m2}$—CH(NHR$_1$)R$_1$, —CH(OH)—(CR$_1$R$_1$)$_{m2}$—CH(NHR$_1$)R$_1$, or —CH(NHR$_1$)—(CR$_1$R$_1$)$_{m2}$—CH(OH)R$_1$, —(CR$_1$R$_1$)$_{m2}$—S—C(NH)NH$_2$, —N=C(NHR$_1$)(R$_3$) or —N=C(NHR$_1$)(R$_1$); wherein each m2 is independently an integer from 0 to 1.

6. The composition of claim 1 wherein G$_1$ is selected from the group consisting of:

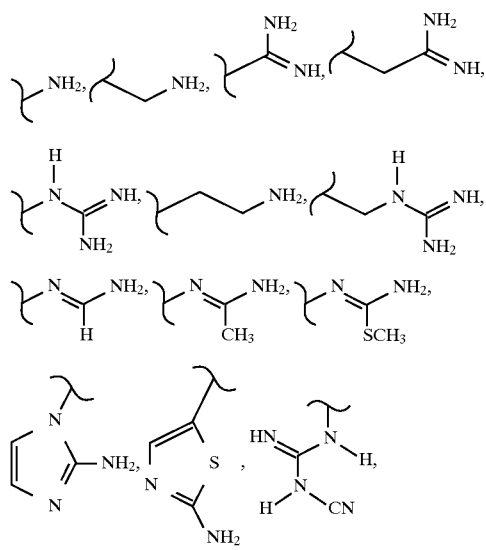

7. The composition of claim 1 wherein W$_3$ is —C(O)—R$_5$ or W$_5$.

8. The composition of claim 7 wherein R$_5$ is an alkyl of 1 to 4 carbon atoms substituted with 0 to 3 fluorine atoms.

9. The composition of claim 1 wherein W$_5$ is selected from the group consisting of:

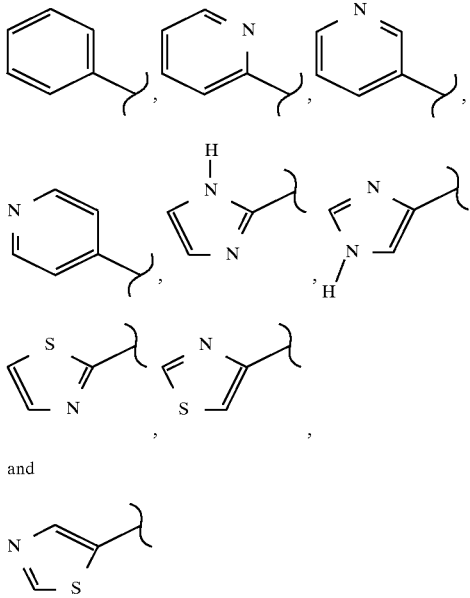

and

10. The composition of claim 1 wherein T$_1$ is selected from the group consisting of:

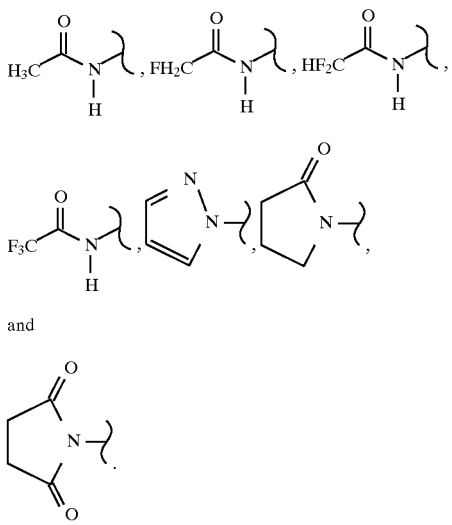

and

11. The composition of claim 1 wherein X$_1$ is —O—, —NH—, —S—, —SO—, or —SO$_2$—.

12. The composition of claim 1 wherein W$_6$ is —CHR$_1$—W$_7$ or —C(O)—W$_7$.

13. The composition of claim 12 wherein W$_7$ is —OR$_1$ or an alkyl of 1 to 3 carbon atoms and is substituted with 1 to 3 hydroxy groups.

14. The composition of claim 1 wherein U$_1$ is —O—CHR$_1$W$_7$.

15. The composition of claim 14 wherein W$_7$ is —OR$_1$, or is an alkyl of 1 to 2 carbon atoms substituted with 1 to 2 hydroxy groups.

16. The composition of claim 1 wherein U$_1$ is selected from the group consisting of:

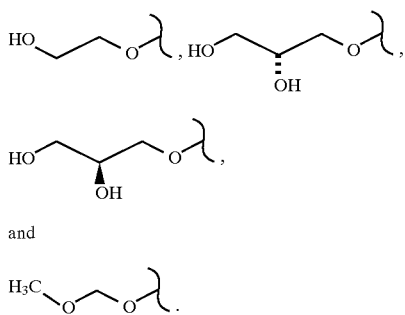

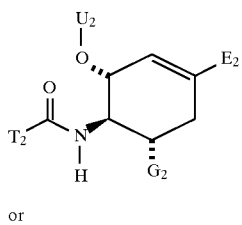

and

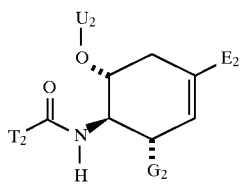

17. The composition of claim 1 comprising a compound of the formula:

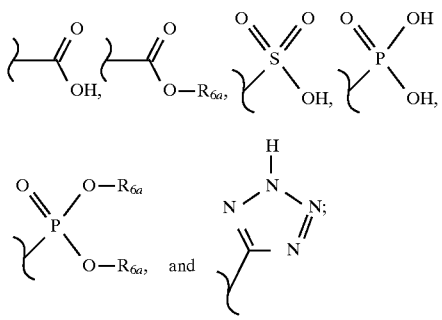

or

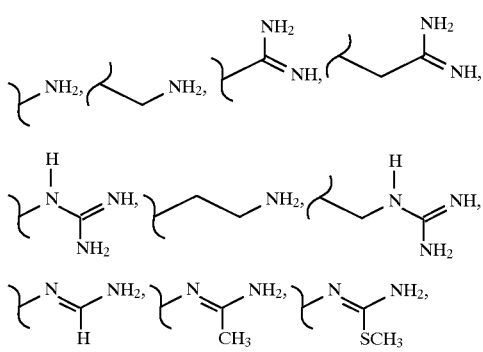

wherein:

E$_2$ is selected from the group consisting of:

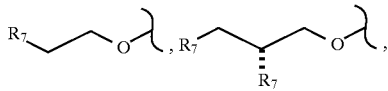

G$_2$ is selected from the group consisting of:

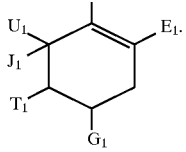

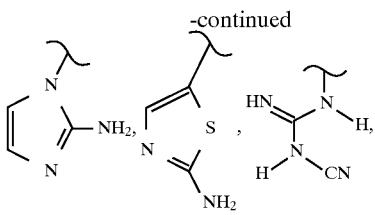

and

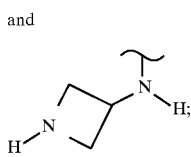

T$_2$ is an alkyl of 1 to 6 carbon atoms, alkenyl of 2 to 6 carbon atoms, or alkynyl of 2 to 6 carbon atom, with the proviso that T$_2$ is substituted with 0 to 3 groups selected from the group consisting of F, Cl, Br, I, —CN, N$_3$, —OR$_{6a}$, —NR$_{6b}$R$_{6b}$, —SR$_{6a}$, —O—C(O)R$_{6a}$, or —NR$_{6b}$—C(O)R$_{6a}$;

U$_2$ is a group selected from the group consisting of:

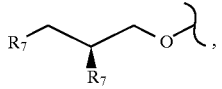

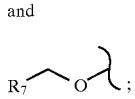

and and

R$_7$ is H, —OH, —OCH3, —OAc, —NH$_2$, or —SH.

18. The composition of claim 1 further comprising a pharmaceuticallyacceptable carrier.

19. The composition of claim 1 which has formula (I).

20. The composition of claim 1 wherein the compound is of the formula:

21. The composition of claim 1 wherein U$_1$ is —X$_1$W$_6$.

22. The composition of claim 1 wherein X$_1$ is —O—.

23. The composition of claim 1 wherein W$_6$ is R$_1$, W$_5$, —CO$_2$R$_{6a}$, —C(O)NR$_{6b}$R$_{6b}$, —C(NR$_{6b}$)NR$_{6b}$R$_{6b}$, —C(S) NR$_{6b}$R$_{6b}$, —C(O)—R$_1$, —CHR$_1$W$_7$, —CH(R$_1$)$_a$W$_7$ (where a is 0 or 1, but is 0 when W$_7$ is divalent) or —C(O)W$_7$, wherein W$_7$ is R$_3$ or an alkyl of 1 to 4 carbons substituted with 1 to 3 R$_3$ groups, typically selected from the group consisting of —NR$_1$(R$_{6b}$), —N(R$_{6b}$)$_2$, —OR$_{6a}$, or SR$_{6a}$.

24. The composition of claim 1 wherein W$_6$ is R$_1$.

25. The composition of claim 24 wherein R$_1$ is a normal, secondary, tertiary or cyclic alkyl containing 1 to 6 carbon atoms.

26. The composition of claim 25 wherein R$_1$ is —CH$_3$, —CH$_2$CH$_3$, —CH$_2$CH$_2$CH$_3$, —CH(CH$_3$)$_2$, —$CH_2CH_2CH_2CH_3$, —$CH_2CH(CH_3)_2$, —$CH(CH_3)CH_2CH_3$, —$C(CH_3)_3$, —$CH_2CH_2CH_2CH_2CH_3$, —$CH(CH_3)CH_2CH_2CH_3$, —$CH(CH_2CH_3)_2$, —$C(CH_3)_2CH_2CH_3$, —$CH(CH_3)CH(CH_3)_2$, —$CH_2CH_2CH(CH_3)_2$, —$CH_2CH(CH_3)CH_2CH_3$, —$CH_2CH_2CH_2CH_2CH_2CH_3$, —$CH(CH_3)CH_2CH_2CH_2CH_3$, —$CH(CH_2CH_3)(CH_2CH_2CH_3)$, —$C(CH_3)_2CH_2CH_2CH_3$, —$CH(CH_3)CH(CH_3)CH_2CH_3$, —$CH(CH_3)CH_2CH(CH_3)_2$, —$C(CH_3)(CH_2CH_3)_2$, —$CH(CH_2CH_3)CH(CH_3)_2$, —$C(CH_3)_2CH(CH_3)_2$, or —$CH(CH_3)C(CH_3)_3$.

27. The composition of claim 26 wherein $W_6$ is $(CH_3CH_2)(CH_3)CH$—.

28. The composition of claim 26 wherein $W_6$ is —$CH(CH_2CH_3)_2$.

29. The composition of claim 1 wherein $E_1$ is —$CO_2R_1$.

30. The composition of claim 1 wherein $G_1$ is —$NH_2$.

31. The composition of claim 1 wherein $T_1$ is $R_5C(O)(H)N$—.

* * * * *